US012767931B2

(12) United States Patent
Si-Tayeb et al.

(10) Patent No.: US 12,767,931 B2
(45) Date of Patent: Oct. 20, 2026

(54) LIVER ORGANOID MANUFACTURING METHODS, LIVER ORGANOIDS OBTAINED WITH THE SAME, AND USES THEREOF

(71) Applicants: INSTITUT NATIONAL DE LA SANTÉ ET DE LA RECHERCHE MÉDICALE, Paris (FR); NANTES UNIVERSITÉ, Nantes (FR); HCS PHARMA, Loos (FR); CNRS (CENTRE NATIONAL DE LA RECHERCHE SCIENTIFIQUE), Paris (FR); CHU DE NANTES, Nantes (FR)

(72) Inventors: Karim Si-Tayeb, Nantes Cedex (FR); Amandine Caillaud, Nantes Cedex (FR); Nathalie Maubon, Loos (FR); Zied Souguir, Loos (FR); Meryl Roudaut, Loos (FR)

(73) Assignees: INSTITUT NATIONAL DE LA SANTÉ ET DE LA RECHERCHE MÉDICALE (INSERM), Paris (FR); NANTES UNIVERSITÉ, Nantes (FR); HCS PHARMA, Loos (FR); CNRS (CENTRE NATIONAL DE LA RECHERCHE SCIENTIFIQUE), Paris (FR); CHU DE NANTES, Nantes (FR)

( * ) Notice: Subject to any disclaimer, the term of this patent is extended or adjusted under 35 U.S.C. 154(b) by 307 days.

(21) Appl. No.: 18/553,316

(22) PCT Filed: Mar. 31, 2022

(86) PCT No.: PCT/EP2022/058724
§ 371 (c)(1),
(2) Date: Sep. 29, 2023

(87) PCT Pub. No.: WO2022/207889
PCT Pub. Date: Oct. 6, 2022

(65) Prior Publication Data

US 2024/0279612 A1 Aug. 22, 2024

(30) Foreign Application Priority Data

Apr. 1, 2021 (EP) .................................... 21305421

(51) Int. Cl.
*C12N 5/071* (2010.01)

(52) U.S. Cl.
CPC ........ *C12N 5/0671* (2013.01); *C12N 2500/02* (2013.01); *C12N 2501/115* (2013.01); *C12N 2501/12* (2013.01); *C12N 2501/15* (2013.01); *C12N 2501/155* (2013.01); *C12N 2501/2306* (2013.01); *C12N 2501/727* (2013.01); *C12N 2501/999* (2013.01); *C12N 2506/45* (2013.01); *C12N 2513/00* (2013.01); *C12N 2533/54* (2013.01); *C12N 2537/10* (2013.01)

(58) Field of Classification Search
None
See application file for complete search history.

(56) References Cited

U.S. PATENT DOCUMENTS

2012/0190059 A1* 7/2012 Deng ..................... C12N 5/067
435/377
2020/0199538 A1* 6/2020 Ng ....................... C12N 5/0671

FOREIGN PATENT DOCUMENTS

WO 2016/166479 A1 10/2016
WO 2020/227711 A1 11/2020

OTHER PUBLICATIONS

Chaker: "Hepatic potential of Reversed-age Mesenchymal Stem Cells and Endodermal Progenitors: Contribution of LGR5 and Cdc42 cell signaling pathways", HAL, Dec. 18, 2017.
Chen et al: "Regulated differentiation of stem cells into an artificial 3D liver as a transplantable source", Clinical and Molecular Hepatology, vol. 26, p. 163-179, Feb. 2, 2020.
Cotovio et al: "Production of Human Pluripotent Stem Cell-Derived Hepatic Cell Lineages and Liver Organoids: Current Status and Potential Applications", Bioengineering, vol. 7, No. 36, Apr. 9, 2020.
Gerbal-Chaloin et al: "Human Induced Pluripotent Stem Cells in Hepatology Beyond the Proof of Concept", The American Journal of Pathology, vol. 184, No. 2, p. 332-347, Feb. 2014.
Harrison et al: "Scalable production of tissue-like vascularised liver organoids from human PSCs", Biorxiv, Dec. 2, 2020.
HCS Pharma: "Applications for 3D in vitro models with Biomimesys Liver", https://www.youtube.com/watch?v=GCWvmR9sXUQ, Mar. 2021.
Kulkeaw et al: "Generation of human liver organoids from pluripotent stem cell-derived hepatic endoderms", PEERJ, Oct. 19, 2020.
Kumar et al: "A fully pluripotent stem cell derived multi-liver-cell model for steatohepatitis and fibrosis", Biorxiv, Sep. 4, 2020.

(Continued)

*Primary Examiner* — Blaine Lankford
(74) *Attorney, Agent, or Firm* — WCF IP

(57) ABSTRACT

The present disclosure relates to methods for preparing a liver organoid, as well as liver organoids obtained with the same and uses thereof. It was observed that, in presence of a set of suitable cell culture media, a use of a 3D porous scaffold and of alternated steps of hypoxic and normoxic conditions was able to drive the differentiation of stems cells in functional liver organoids comprising at least in hepatocytes, cholangiocytes, stellate cells, and sinusoidal endothelial cells. The obtained liver organoids expressed liver-specific genes, responded to LDL internalization, showed lipid accumulation and presented a strong activity of CYP enzymes.

25 Claims, 26 Drawing Sheets

(56) References Cited

OTHER PUBLICATIONS

Nagaoka et al: "Immobolized E-cadherin model can enhance cell attachment and differentiation of primary hepatocytes but not proliferation", Biotechnology Letters, vol. 24, p. 1857-1862, 2002.
Olgasi et al: "iPSC-Derived Liver Organoids: A Journey from Drug Screening, to Disease Modeling, Arrived to Regenerative Medicine", International Journal of Molecular Sciences, vol. 21, No. 6215, Aug. 27, 2020.
Ouchi et al: "Modeling Steatohepatitis in Humans with Pluripotent Stem Cell-Derived Organoids", Cell Metabolism, vol. 30, p. 374-384, Aug. 6, 2019.
Si-Tayeb et al: "Highly Efficient Generation of Human Hepatocyte-like Cells from Induced Pluripotent Stem Cells", Hepatology, vol. 51, No. 1, p. 297-305, Jan. 2010.
Takebe et al: "Vascularized and functional human liver from an iPSC-derived organ bud transplant", Research Letter, vol. 0, 2013.
Takebe et al: "Generation of a vascularized and functional human liver from an iPSC-derived organ bud transplant", Nature Protocols, vol. 9, No. 2, p. 396-409, 2014.
Takebe et al: "Massive and Reproducible Production of Liver Buds Entirely from Human Pluripotent Stem Cells", Cell Reports, vol. 21, p. 2661-2670, Dec. 5, 2017.
Zhang et al: "Urine Derived Cells are a Potential Source for Urological Tissue Reconstruction", The Journal of Urology, vol. 180, p. 2226-2233, Nov. 2008.

* cited by examiner

LIVER ORGANOID MANUFACTURING METHODS, LIVER ORGANOIDS OBTAINED WITH THE SAME, AND USES THEREOF

TECHNICAL FIELD

The present disclosure relates to methods for preparing a liver organoid, as well as liver organoids obtained with the same and uses thereof. Further, the present disclosure relates to a method for preparing liver organoids comprising differentiating a single pluripotent stem cells line in multiple different liver somatic cells by means of alternated hypoxic and normoxic conditions and use of different growth cell culture media.

BACKGROUND

The liver is a vital organ that provides many essential metabolic functions for life such as the detoxification of exogenous compounds and coagulation as well as producing lipids, proteins, ammonium, and bile. In vitro reconstitution of a liver, such as liver organoids or liver models, may provide applications including regenerative therapies and hepatocyte transplantation therapies, as well as models for study of molecular and genetic aspects of human hepatic disease, for drug discovery and for drug toxicity studies. In particular, the development of such models could be used to better understand the involvement of PCSK9 in the development of some liver diseases, but also could be used in the modeling of complex pathologies such as NASH (Non-Alcoholic SteatoHepatitis) or ASH (Alcoholic SteatoHepatitis).

The basic architectural unit of the liver is the liver lobule. Each lobule consists of plates of hepatocytes lined by sinusoidal capillaries that radiate toward a central efferent vein. Liver lobules are roughly hexagonal with each of six corners demarcated by the presence of a portal triad (portal vein, bile duct, and hepatic artery). Although hepatocytes are the major parenchymal cell type of the liver, they function in concert with cholangiocytes (biliary epithelial cells), endothelial cells, sinusoidal endothelial cells, Kupffer cells, natural killer cells and hepatic stellate cells. This complex architecture is crucial for hepatic function.

Existing methodologies to develop liver organoid using liver cells exhibit extremely poor functionality, largely due to a lack of essential anatomical structures, which limits their practical use for the pharmaceutical industry.

The generation of hepatocytes from induced pluripotent stem cells (iPSC) is particularly appealing because this parenchymal cell of the liver is associated with several congenital diseases, is the site of xenobiotic control, and is the target of many pathogens that cause severe liver dysfunction including hepatitis B and C viruses. Nonetheless, the process of obtaining hepatocytes from human somatic cells requires several steps: isolation and reprogramming toward human induced pluripotent stem cells (hiPSCs), followed by differentiation and maturation of hiPSCs into hepatocyte-like cells (HLCs) (Gerbal-Chaloin et al., *Am J Pathol.* 2014 February; 184(2):332-47).

Different liver models were developed using human iPSC (hiPSC) such as 2-dimensions models (Si-Tayeb et al., *Hepatology.* 2010 January; 51(1):297-305; Gerbal-Chaloin et al., *Am J Pathol.* 2014 February; 184(2):332-47; Si-Tayeb et al., *Dis Model Mech.* 2016 January; 9(1):81-90) or 3-dimensions (3D) models (Takebe et al., *Cell Rep.* 2017 Dec. 5; 21(10):2661-2670; Ouchi et al., *Cell Metab.* 2019 Aug. 6; 30(2):374-384.e6.). Those models were to study hepatic metabolism and hepatic diseases such as steatohepatitis or PCSK9-mediated autosomal dominant hypercholesterolemia.

Liver 2-dimension models obtained with the differentiation protocols described in Ouchi et al., (*Cell Metab.* 2019 Aug. 6; 30(2):374-384.e6) or Kumar et al. (*bioRxiv,* 2020 Sep. 4) are performed with a Matrigel™ as scaffold. Matrigel™ is a reconstituted basement membrane derived from extracts of Engelbreth-Holm-Swarm mouse tumors. Since the Matrigel™ is derived from a tumor cell model, the exact composition of Matrigel™ may not be consistent or precisely defined. Additionally, the use of liver organoid obtained by a process implemented a scaffold of Matrigel™ for therapeutic applications in human may not be biocompatible due to its tumor cell origins.

Recently, liver organoids produced in suspension were described by Harrison et al. (*bioRxiv* 2020.12.02.406835) as presenting a liver-like cellular repertoire including stellate cells, endothelial cells, hepatocytes and Kupffer cells, a high order cellular complexity, and vascular luminal structures. The organoids exhibited liver functions such as drug metabolism, serum protein production, coagulation factor production, bilirubin uptake and urea synthesis. However, growth in suspension may entail further operations for separating the liver organoids from the growth medium which may be time consuming and may be deleterious for the liver organoids.

However, some models may have an immature liver phenotype that is closer to a perinatal liver. Furthermore, most of them do not take into account the complexity of the tissues and the extracellular environment to which the cells are exposed.

The liver organoid model developed by Takebe (Takebe et al., *Cell Rep.* 2017 Dec. 5; 21(10):2661-2670) was shown to acquire good hepatic functionalities after the end of differentiation with improved albumin production and the production of a number of key proteins in liver serum, notably complement factor H, coagulation factor VIII, transferrin and AAT. However, the developed procedure requires separate differentiation of three different cell types from hiPSCs (endothelial progenitor cells, hepatocyte progenitor cells and mesenchymal cells) (Takebe et al., *Nature,* 2013, 499, 481-484; Takebe et al., *Nat Protoc.* 2014 February; 9(2):396-409; Takebe et al., *Cell Rep.* 2017 Dec. 5; 21(10):2661-2670). This type of procedure appears to be time-consuming and quite expensive. Therefore, there is a need to develop a liver organoid presenting a cell diversity and organization resembling the in vivo organization of a liver lobule.

There is a need to develop a liver organoid in a 3D scaffold.

There is a need to have a liver organoid mimicking in vivo hepatic metabolism and functions.

There is a need to have a liver organoid which can stably maintain hepatic function and metabolism over time.

There is a need to have a simple and reliable method for growing and manufacturing liver organoids.

There is a need to have a simple and reliable method for manufacturing liver organoids in a 3D scaffold.

There is a need to have a method for manufacturing liver organoids which may be used for human therapy.

There is a need to have a method for manufacturing liver organoids which may be easily implemented with iPSC derived from various patients.

There is a need to have a method for manufacturing liver organoids resembling the in vivo organization of a liver lobule.

There is a need to have a method for manufacturing liver organoids mimicking in vivo hepatic metabolism and functions.

There is a need to have a method for manufacturing liver organoids which can stably maintain hepatic function and metabolism over time.

There is need to have a method for manufacturing liver organoids which can be easily scaled up. There is need to have a method for manufacturing liver organoids which can be easily implemented at industrial level.

There is a need to have liver organoids grown in 3D-scaffold which therefore may be easily manipulated for various uses.

The present disclosure has for goal to satisfy all or part of those needs.

SUMMARY

In one embodiment, the disclosure relates to a method for preparing a liver organoid, the method using at least:

i) a three-dimensional porous scaffold seeded with isolated stem cells, ii) a set of cell-culture media for mammal cells suitable for growing and differentiating the isolated stem cells into a liver organoid, the method comprising at least a step of:

a) contacting the seeded stem cells with a first set of cell culture media, under normoxic condition, to differentiate the stem cells in definitive mesendoderm cells;

b) contacting the definitive mesendoderm cells obtained at step a) with a second set of cell culture media, under hypoxic condition, to differentiate the definitive mesendoderm cells in hepatic endoderm cells;

c) contacting the hepatic endoderm cells obtained at step b) with a third set of cell culture media, under hypoxic condition, to differentiate the hepatic endoderm cells in hepatic progenitor cells; and d) contacting the hepatic progenitor cells obtained at step c) with a fourth set of cell culture media, under normoxic condition, to differentiate the hepatic progenitor cells in a liver organoid.

The differentiation of stem cells into definitive endoderm cells goes through a set of intermediate differentiated stages including early endoderm cells and definitive mesendoderm cells. Those stages are transitional and may not be readily isolated in cell cultures.

In one embodiment, the disclosure relates to a method for preparing a liver organoid, the method using at least:

i) a three-dimensional porous scaffold seeded with isolated stem cells, ii) a set of cell-culture media for mammal cells suitable for growing and differentiating the isolated stem cells into a liver organoid, the method comprising at least a step of:

a) contacting the seeded stem cells with a first set of cell culture media, under normoxic condition, to differentiate the stem cells in definitive endoderm cells;

b) contacting the definitive endoderm cells obtained at step a) with a second set of cell culture media, under hypoxic condition, to differentiate the definitive endoderm cells in hepatic endoderm cells;

c) contacting the hepatic endoderm cells obtained at step b) with a third set of cell culture media, under hypoxic condition, to differentiate the hepatic endoderm cells in hepatic progenitor cells; and d) contacting the hepatic progenitor cells obtained at step c) with a fourth set of cell culture media, under normoxic condition, to differentiate the hepatic progenitor cells in a liver organoid.

As detailed in the Examples section, the inventors have surprisingly observed that by using a simple procedure of alternating hypoxic and normoxic cell culture conditions maturation of stem cells, such as hiPSC, into hepatocyte-like cells (HLCs) was greatly improved. Furthermore, they have surprisingly observed that maturation of stem cells, such as hiPSC, into hepatocyte-like cells (HLCs) was greatly improved by using a 3D-porous scaffold, as for example a 3D-porous hydroscaffold. Furthermore, the inventors have surprisingly observed that by using a simple procedure of alternating hypoxic and normoxic cell culture conditions, in particular with cells seeded in a 3D-scaffold, it was possible to develop a complex, organized, liver organoid including different liver somatic cell types starting from a single stem cells line.

Furthermore, the inventors have observed that using a 3D-porous scaffold made of hyaluronic acid matrix, for example a cross-linked hyaluronic acid, for example as disclosed in WO 2016/166479 A1, it was possible to seed and differentiate the stem cells, such as hiPSCs, simply and directly inside the matrix to mimic the different stages of hepatocytes and liver development, in particular with an alternate sequence of hypoxic and normoxic cell culture conditions.

As shown in the Examples section, the inventors have developed an improved method for manufacturing liver organoid using a set of cells culture media supplemented with different cytokines or molecules, including Activin A, Bone Morphogenetic Protein 4 (BMP4), Fibroblast Growth Factor 2 (FGF2), Hepatocyte Growth Factor (HGF), and Oncostatin M (OSM), Vascular Endothelial Growth Factor (VEGF), an inhibitor of the TGF-β/Activin/NODAL pathway (SB431542), and dexamethasone.

The inventors have observed that a combination of a specific alternate sequence of hypoxic and normoxic cell culture conditions, with specific sets of cytokines and a 3D-porous scaffold, for example made of functionalized cross-linked hyaluronic acid, was able to different a single type of stem cells in functional liver organoids with 4 different types of cells: hepatocytes, stellate cells, cholangiocytes and sinusoidal endothelial cells.

As detailed in the Examples section, the liver organoids obtained according to the procedure developed by the inventors were characterized by the upregulation of many hepatic genes, such as the genes associated with the liver and liver functions (metabolism of bile, fatty acids, cholesterol, lipoproteins, glucose, insulin, cytochromes and xenobiotics). Further, the liver organoids were also characterized by a cellular organization of different cell types in addition to hepatocytes, such as stellate cells, cholangiocytes and sinusoidal endothelial cells, and by an LDL internalizing capacity that was increased by statins, by a capacity for lipid accumulation and by an improvement in CYP activity compared to HLC developed in a 2D matrix.

The methods disclosed herein may advantageously use at step a) a single type of stem cells.

Within the disclosure, a "single type" of stem cells intends to mean that the stem cells are all fully and similarly dedifferentiated. Otherwise said, the used stem cells are not comprised of variously dedifferentiated stem cells, or partially differentiated cells, that is primed or conditioned to differentiate in various somatic cells.

In one embodiment, a method as disclosed herein may comprise:

a) within the step of differentiating the seeded stem cells in definitive mesendoderm cells:
   a1) a first phase of contacting the cells with a first cell-culture medium supplemented with a SMAD2/3 pathway activator, a fibroblast growth factor, and a bone morphogenetic protein, and
   a2) a second phase of contacting the cells with a second cell-culture medium supplemented with a SMAD2/3 pathway activator, thereby obtaining the definitive mesendoderm cells;

b) within the step of differentiating the definitive mesendoderm cells obtained at step a) in hepatic endoderm cells, contacting the cells with a third cell-culture medium supplemented with a fibroblast growth factor, a vascular endothelial growth factor, and a bone morphogenetic protein, thereby obtaining the hepatic endoderm cells;

c) within the step of differentiating the hepatic endoderm cells obtained at step b) in hepatic progenitor cells:
   c1) a first phase of contacting the cells with a fourth cell-culture medium supplemented with a hepatocyte growth factor, and an inhibitor of the TGF-β/Activin/NODAL pathway,
   c2) a second phase of contacting the cells with a fifth cell-culture medium supplemented with a hepatocyte growth factor, and
   c3) a third phase of contacting the cells with a sixth cell-culture medium supplemented with a hepatocyte growth factor and an interleukin (IL)-6 cytokine family activator, thereby obtaining the hepatic progenitor cells; and d) within the step of differentiating the hepatic progenitor cells obtained at step c) in the liver organoid:
   d1) a first phase of contacting the cells with a seventh cell-culture medium, said cell-culture medium being a hepatocyte-culture medium supplemented with a hepatocyte growth factor, an interleukin (IL)-6 cytokine family activator, and a steroid,
   d2) a second phase of contacting the cells with an eighth cell-culture medium, said cell-culture medium being a hepatocyte-culture medium supplemented with an interleukin (IL)-6 cytokine family activator, and a steroid, and
   d3) a third phase of contacting the cells with a ninth cell-culture medium, said cell-culture medium being a hepatocyte-culture medium, and thereby obtaining the liver organoid in the three-dimensional porous cell culture scaffold.

In one embodiment, a method as disclosed herein may comprise:

a) within the step of differentiating the seeded stem cells in definitive endoderm cells:
   a1) a first phase of contacting the cells with a first cell-culture medium supplemented with a SMAD2/3 pathway activator, a fibroblast growth factor, and a bone morphogenetic protein, and
   a2) a second phase of contacting the cells with a second cell-culture medium supplemented with a SMAD2/3 pathway activator, thereby obtaining the definitive endoderm cells;

b) within the step of differentiating the definitive endoderm cells obtained at step a) in hepatic endoderm cells, contacting the cells with a third cell-culture medium supplemented with a fibroblast growth factor, a vascular endothelial growth factor, and a bone morphogenetic protein, thereby obtaining the hepatic endoderm cells;

c) within the step of differentiating the hepatic endoderm cells obtained at step b) in hepatic progenitor cells:
   c1) a first phase of contacting the cells with a fourth cell-culture medium supplemented with a hepatocyte growth factor, and an inhibitor of the TGF-β/Activin/NODAL pathway,
   c2) a second phase of contacting the cells with a fifth cell-culture medium supplemented with a hepatocyte growth factor, and
   c3) a third phase of contacting the cells with a sixth cell-culture medium supplemented with a hepatocyte growth factor and an interleukin (IL)-6 cytokine family activator, thereby obtaining the hepatic progenitor cells; and d) within the step of differentiating the hepatic progenitor cells obtained at step c) in the liver organoid:
   d1) a first phase of contacting the cells with a seventh cell-culture medium, said cell-culture medium being a hepatocyte-culture medium supplemented with a hepatocyte growth factor, an interleukin (IL)-6 cytokine family activator, and a steroid,
   d2) a second phase of contacting the cells with an eighth cell-culture medium, said cell-culture medium being a hepatocyte-culture medium supplemented with an interleukin (IL)-6 cytokine family activator, and a steroid, and
   d3) a third phase of contacting the cells with a ninth cell-culture medium, said cell-culture medium being a hepatocyte-culture medium, and thereby obtaining the liver organoid in the three-dimensional porous cell culture scaffold.

In one embodiment, a method as disclosed herein may comprise a first step before step a), said first step comprising contacting the stem cells seeded in the scaffold in a tenth cell-culture medium supplemented with a ROCK family pathway inhibitor, said step being under hypoxic condition.

In one embodiment, a scaffold may be a cross-linked hydrogel. A cross-linked hydrogel may be comprised of cross-linked glycosaminoglycans, for example a cross-linked hyaluronic acid, or cross-linked anionic biopolymers, and of collagen, fibronectin, or laminin.

In one embodiment, a scaffold may be a cross-linked hydrogel comprised of cross-linked glycosaminoglycans, in particular of cross-linked hyaluronic acids, and of collagen, fibronectin or laminin, and for example of collagen.

The glycosaminoglycan or the anionic biopolymer may be functionalized.

In another embodiment, a scaffold may be a cross-linked hydrogel comprised of cross-linked glycosaminoglycan and of collagen. In another embodiment, a scaffold may be a cross-linked hydrogel comprised of cross-linked hyaluronic acid and of collagen. The glycosaminoglycan, for example the hyaluronic acid, may be functionalized.

In one embodiment, a scaffold may have pores having an average pore size ranging from about 50 μm to about 500 μm, in particular from about 80 μm to about 400 μm, in particular from about 100 μm to about 350 μm, in particular from about 100 μm to about 300 μm, in particular from about 100 μm to about 200 μm.

In some preferred embodiments, a scaffold may have pores having an average pore size from about 100 μm to about 200 μm, in particular of about 100 μm, 105 μm, 110 μm, 115 μm, 120 μm, 125 μm, 130 μm, 135 μm, 140 μm, 145

μm, 150 μm, 155 μm, 160 μm, 165 μm, 170 μm, 175 μm, 180 μm, 185 μm, 190 μm, 195 μm or 200 μm.

In some embodiments, a scaffold may have pores having an average pore size of about 100 μm, for example of 100 μm+/−20 μm.

In some embodiments, a scaffold may have pores having an average pore size of about 150 μm, for example of 150 μm+/−20 μm.

In some embodiments, a scaffold may have pores having an average pore size of about 200 μm, for example of 200 μm+/−20 μm.

In one embodiment, a SMAD2/3 pathway activator may be Activin A, NODAL, TGFβ1, TGFβ2 or TGFβ. A fibroblast growth factor may be FGF2. A bone morphogenetic protein may be BMP4. A TGF-β/Activin/NODAL pathway inhibitor may be SB431542. An interleukin (IL)-6 cytokine family activator may be Oncostatin M. A steroid may be dexamethasone.

In one embodiment, the cell culture media of steps a) to c) may be a DMEM, a MEM, a K-DMEM, a G-MEM, a BME, an Advanced DMEM/Ham's F12, an IMDM, a Ham's F-10, a Ham's F-12, a Medium 199, a RPMI 1640 or a DMEM/Ham's F12 media.

In one embodiment, the cell culture media of steps a) to c) may be a DMEM, a MEM, a K-DMEM, a G-MEM, a BME, an Advanced DMEM/Ham's F12, an IMDM, a Ham's F-10, a Ham's F-12, a Medium 199, a DMEM/Ham's F12, or a RPMI 1640, optionally supplemented with growth and maintenance medium supplements, cytokines, inhibitory and/or activating molecules, or a RPMI 1640 or a DMEM/Ham's F12 media supplemented with growth and maintenance medium supplements, cytokines, inhibitory and/or activating molecules.

In one embodiment, the cell culture media of steps a) to c) may be a DMEM, a MEM, a K-DMEM, a G-MEM, a BME, an Advanced DMEM/Ham's F12, an IMDM, a Ham's F-10, a Ham's F-12, a Medium 199, a DMEM/Ham's F12, or a RPMI 1640, optionally supplemented with a B27 or a N-2 supplement, or a RPMI 1640 or a DMEM/Ham's F12 media supplemented with a B27 or a N-2 supplement, in particular with a B27 supplement.

In one embodiment, a cell culture medium of steps a) to c) may be RPMI 1640 or DMEM/Ham's F12, optionally supplemented with a B27 or a N-2 supplement, in particular may be RPMI 1640, supplemented with B27 or N-2 supplement, in particular with a B27 supplement.

In one embodiment, a cell culture medium of step d) may be a hepatocyte cell culture medium without endothelial growth factor.

In one embodiment, the stems cells may be differentiated, at least, in hepatocytes, cholangiocytes, stellate cells, and sinusoidal endothelial cells.

In one embodiment, a method for preparing a liver organoid as disclosed herein may comprise at least:

i) a three-dimensional porous scaffold seeded with isolated stem cells, the three-dimensional porous scaffold being comprised of cross-linked hyaluronic acid grafted with RGDS (Arg-Gly-Asp-Ser) peptides and of collagen, ii) a set of cell-culture media for mammal cells suitable for growing and differentiating the isolated stem cells into a liver organoid, the method comprising at least a step of:

a) contacting the seeded stem cells with a first set of cell culture media, under normoxic condition, to differentiate the stem cells in definitive endoderm cells, said step comprising:

a1) a first phase lasting for about 2 days of contacting the stem cells with a first cell-culture medium, for example RPMI 1640, supplemented with B27 comprising insulin, and comprising a SMAD2/3 pathway activator, a fibroblast growth factor, and a bone morphogenetic protein, thereby differentiating the stem cells in mesendoderm cells; and a2) a second phase lasting for about 3 days of contacting the mesendoderm cells with a second cell-culture medium, for example RPMI 1640, supplemented with B27 comprising insulin, and comprising a SMAD2/3 pathway activator, thereby differentiating the mesendoderm cells in definitive endoderm cells, b) contacting the definitive endoderm cells obtained at step a) with a second set of cell culture media, under hypoxic condition, to differentiate the definitive endoderm cells in hepatic endoderm cells, said step comprising a single phase lasting about 5 days of contacting the definitive endoderm cells with a third cell-culture medium, for example RPMI 1640, supplemented with B27 comprising insulin, and comprising a fibroblast growth factor, a vascular endothelial growth factor, and a bone morphogenetic protein, thereby differentiating the definitive endoderm cells in hepatic endoderm cells, and c) contacting the hepatic endoderm cells obtained at step b) with a third set of cell culture media, under hypoxic condition, to differentiate the hepatic endoderm cells in hepatic progenitor cells, said step comprising:

c1) a first phase lasting about 3 days of contacting the cells with a fourth cell-culture medium, for example RPMI 1640, supplemented with B27 comprising insulin, and comprising a hepatocyte growth factor, and an inhibitor of the TGF-β/Activin/NODAL pathway, c2) a second phase lasting about 3 days of contacting the cells with a fifth cell-culture medium, for example RPMI 1640, supplemented with B27 comprising insulin, and comprising a hepatocyte growth factor, and c3) a third phase lasting about 3 days of contacting the cells with a sixth cell-culture medium, for example RPMI 1640, supplemented with B27 comprising insulin, and comprising a hepatocyte growth factor, and an interleukin (IL)-6 cytokine family activator, thereby differentiating the hepatic endoderm cells in hepatic progenitor cells, and d) contacting the hepatic progenitor cells obtained at step c) with a further set of cell culture media, under normoxic condition, to differentiate the hepatic progenitor cells in a liver organoid, said step comprising:

d1) a first phase lasting about 6 days of contacting the hepatic progenitor cells with a seventh cell culture medium, for example a hepatocyte culture medium, comprising a hepatocyte growth factor, an interleukin (IL)-6 cytokine family activator, and a steroid, d2) a second phase lasting about 3 days of contacting the early hepatocyte cells with an eighth cell culture medium, for example a hepatocyte culture medium, comprising an interleukin (IL)-6 cytokine family activator, and a steroid, and d3) a third phase lasting about 1 day of contacting the hepatocyte cells with a ninth cell culture medium, for example a hepatocyte culture medium, thereby obtaining a liver organoid.

Methods disclosed herein may further comprise, before the step a) as above indicated, a step of contacting, for about 3 days, under hypoxic condition, the stem cells with a cell-culture medium, for example StemMACS iPS-Brew, comprising a ROCK family pathway inhibitor.

In one embodiment, a method for preparing a liver organoid as disclosed herein may comprise at least:

i) a three-dimensional porous scaffold seeded with isolated stem cells, the three-dimensional porous scaffold being comprised of cross-linked hyaluronic acid grafted with RGDS (Arg-Gly-Asp-Ser) peptides and of collagen, ii) a set of cell-culture media for mammal cells suitable for growing and differentiating the isolated stem cells into a liver organoid, the method comprising at least a step of:

a) contacting the seeded stem cells with a first set of cell culture media, under normoxic condition, to differentiate the stem cells into definitive endoderm cells, said step comprising:

a1) a first phase lasting for about 2 days of contacting the stem cells with a first cell-culture medium, for example RPMI 1640, supplemented with B27 comprising insulin, and comprising Activin A, Fibroblast Growth Factor 2, and Bone Morphogenetic Protein 4, thereby differentiating the stem cells into mesendoderm cells; and a2) a second phase lasting for about 3 days of contacting the mesendoderm cells with a second cell-culture medium, for example RPMI 1640, supplemented with B27 comprising insulin, and comprising Activin A, thereby differentiating the mesendoderm cells into definitive endoderm cells, b) contacting the definitive endoderm cells obtained at step a) with a second set of cell culture media, under hypoxic condition, to differentiate the definitive endoderm cells in hepatic endoderm cells, said step comprising a single phase lasting about 5 days of contacting the definitive endoderm cells with a third cell-culture medium, for example RPMI 1640, supplemented with B27 comprising insulin, and comprising Fibroblast Growth Factor 2, a Vascular Endothelial Growth Factor, Bone Morphogenetic Protein 4, thereby differentiating the definitive endoderm cells into hepatic endoderm cells, and c) contacting the hepatic endoderm cells obtained at step b) with a third set of cell culture media, under hypoxic condition, to differentiate the hepatic endoderm cells into hepatic progenitor cells, said step comprising:

c1) a first phase lasting about 3 days of contacting the cells with a fourth cell-culture medium, for example RPMI 1640, supplemented with B27 comprising insulin, and comprising hepatocyte growth factor and SB431542, c2) a second phase lasting about 3 days of contacting the cells with a fifth cell-culture medium, for example RPMI 1640, supplemented with B27 comprising insulin, and comprising a hepatocyte growth factor, and c3) a third phase lasting about 3 days of contacting the cells with a sixth cell-culture medium, for example RPMI 1640, supplemented with B27 comprising insulin, and comprising a hepatocyte growth factor, and Oncostatin M, thereby differentiating the hepatic endoderm cells into hepatic progenitor cells, and d) contacting the hepatic progenitor cells obtained at step c) with a further set of cell culture media, under normoxic condition, to differentiate the hepatic progenitor cells into a liver organoid, said step comprising:

d1) a first phase lasting about 6 days of contacting the hepatic progenitor cells with a seventh cell culture medium, for example a hepatocyte culture medium, comprising a hepatocyte growth factor, Oncostatin M, and dexamethasone, d2) a second phase lasting about 3 days of contacting the early hepatocyte cells with an eighth cell culture medium, for example a hepatocyte culture medium, comprising Oncostatin M, and dexamethasone, and d3) a third phase lasting about 1 day of contacting the hepatocyte cells with a ninth cell culture medium, for example a hepatocyte culture medium, thereby obtaining a liver organoid.

Methods disclosed herein may further comprise, before the step a) as above indicated, a step of contacting, for about 3 days, under hypoxic condition, the stem cells with a cell-culture medium, for example StemMACS iPS-Brew, comprising a ROCK family pathway inhibitor, such as Y27632.

In one embodiment, the present disclosure relates to a liver organoid comprising at least hepatocytes, cholangiocytes, stellate cells, and sinusoidal endothelial cells, and being obtained according to a method as disclosed herein.

In one embodiment, the present disclosure relates to a liver organoid in a three-dimensional porous scaffold, the liver organoid comprising at least hepatocytes, cholangiocytes, stellate cells, and sinusoidal endothelial cells, and the three-dimensional porous scaffold is comprised of cross-linked hyaluronic acid and of collagen.

In one embodiment, a liver organoid as disclosed herein may be in a three-dimensional (3D) porous scaffold. The 3D porous scaffold may be a cross-linked hydrogel. A cross-linked hydrogel may be comprised of cross-linked glycosaminoglycan. Further, a cross-linked hydrogel may be comprised of cross-linked hyaluronic acid and of collagen. In one embodiment, the hyaluronic acid may be grafted with RGDS (Arg-Gly-Asp-Ser) peptides.

In one embodiment, a 3D-porous scaffold may be comprised of cross-linked hyaluronic acid and of collagen, the hyaluronic acid being grafted with RGDS (Arg-Gly-Asp-Ser) peptides.

In one embodiment, a liver organoid as disclosed herein may express at least one of proteins chosen among Zonulas-Occludens 1 (ZO-1), E-cadherin, and OATP1B1.

In one embodiment, a liver organoid as disclosed herein may be comprised of:

hepatocytes expressing albumin; and/or stellate cells expressing LHX2 and/or desmine; and/or cholangiocytes expressing CFTR and/or SOX9; and/or sinusoidal endothelial cells expressing CD31 and/or LYVE1.

In one embodiment, a liver organoid as disclosed herein may express at least one of the genes selected from CYP3A4, CYP1A2, CYP2C9, CYP2D6, CYP2B6, LIPC, UGT2B7, and PLG.

In one embodiment, the present disclosure relates to a use of a liver organoid prepared by the method as disclosed herein, or a liver organoid as disclosed herein for drug discovery screens, drug developments, toxicity assays, serious adverse event (SAE) detection, regenerative medicine, or for the treatment of hepatic disorders.

A liver organoid prepared by a method as disclosed herein, or a liver organoid as disclosed herein may be for use in a method of treatment of a hepatic disorder or in regenerative medicine.

In one embodiment, the present disclosure relates to a method of treating an individual having a liver disorder, comprising at least a step implanting a liver organoid prepared by a method as disclosed herein, or a liver organoid as disclosed herein into said individual.

In one embodiment, the present disclosure relates to a kit-of-parts for preparing a liver organoid, the kit-of-parts comprising:

i) isolated stem cells, ii) a three-dimensional porous scaffold comprised of cross-linked hyaluronic acid and of collagen, iii) a set of cell-culture media for mammal cells suitable for differentiating the stem cells into a liver organoid, iv) a set of additives comprising a SMAD2/3 pathway activator, a fibroblast growth factor, a bone morphogenetic protein, a vascular endothelial growth factor, a hepatocyte growth factor, an inhibitor of the TGF-β/Activin/NODAL pathway, an interleukin (IL)-6 cytokine family activator, a steroid, and optionally B27, v) a set of instructions for preparing said liver organoid according to a method as disclosed herein.

DESCRIPTION OF THE FIGURES

FIG. 1**B: Ordinate: Fluorescence signal (A.U.) of lipids into LO. Abscissa: (i) Control (DMSO 0.1%) and (ii) ethanol 100 nM. *p-value <0.05.

FIG. 3 Abscissa (from left to right): (i) CYP3A4 basal for HLC; (ii) CYP3A4 basal for LO; (iii) CYP3A4 basal for PHH. FIG. 4 Abscissa (from left to right): (i) CYP1A2 basal for HLC; (ii) CYP1A2 basal for LO; (iii) CYP1A2 basal for PHH. FIG. 5 Abscissa (from left to right): (i) CYP2C9 basal for HLC; (ii) CYP2C9 basal for LO; (iii) CYP2C9 basal for PHH. FIG. 6 Abscissa (from left to right): (i) CYP2D6 basal for HLC; (ii) CYP2D6 basal for LO; (iii) CYP2D6 basal for PHH. FIG. 7** Abscissa (from left to right): (i) CYP2B6 basal for HLC; (ii) CYP2B6 basal for LO; (iii) CYP2B6 basal for PHH.

FIGS. 8 to 12 show the expression of CYP3A4 (FIGS. 8A & 8B), CYP1A2 (FIGS. 9A & 9B), CYP2C9 (FIGS. 10A & 10B), CYP2D6 (FIGS. 11A & 11B) and CYP2B6 (FIGS. 12A & 12B) activities by mass spectrometry on liver organoids (LO—black bar), hepatocyte cells (PHH—white bar) and primary human hepatocytes (HLC—grey bar). LO, PHH and HLC, after short-term (3 days) or long-term (2 weeks) cell maintenance, were incubated with different types of inducers at different concentrations for 3 days: Omeprazole (50 μM), Rifampicin (10 μM), Imidazole (500 μM), Phenobarbital (500 μM), CITCO (1 μM) and DMSO 0.1% (without induction—Basal condition). Data represent mean±SD (n=3-4 per condition); * p-value <0.05, ** p-value <0.01.

FIG. 13 shows a comparison of the basal and induced activities of the CYP3A4 on LO. Ordinate: Activity of CYP3A4 induced by Rifampicin (Induced condition—10 μM). Normalized value to 1 μg of RNA. Abscissa (from left to right): (i) Basal condition on short-term cell maintenance; (ii) Induced condition on short-term cell maintenance; (iii) Basal condition on long-term cell maintenance; (iv) Induced condition on long-term cell maintenance.

FIG. 14 shows a comparison of the basal and induced activities of the CYP1A2 on LO. Ordinate: Activity of CYP1A2 induced by Omeprazole (Induced condition—50 μM). Normalized value to 1 μg of RNA. Abscissa (from left to right): (i) Basal condition on short-term cell maintenance; (ii) Induced condition on short-term cell maintenance; (iii) Basal condition on long-term cell maintenance; (iv) Induced condition on long-term cell maintenance.

FIG. 15 shows a comparison of the basal and induced activities of the CYP2C9 on LO. Ordinate: Activity of CYP2C9 induced by Rifampicin (Induced condition—10 μM). Normalized value to 1 μg of RNA. Abscissa (from left to right): (i) Basal condition on short-term cell maintenance; (ii) Induced condition on short-term cell maintenance; (iii) Basal condition on long-term cell maintenance; (iv) Induced condition on long-term cell maintenance.

FIG. 16 shows a comparison of the basal and induced activities of the CYP2D6 on LO. Ordinate: Activity of CYP2D6 induced by a mix of Omeprazole (Induced condition—50 μM), Rifampicin (Induced condition—10 μM) and Imidazole (Induced condition—500 μM). Normalized value to 1 μg of RNA. Abscissa (from left to right): (i) Basal condition on short-term cell maintenance; (ii) Induced condition on short-term cell maintenance; (iii) Basal condition on long-term cell maintenance; (iv) Induced condition on long-term cell maintenance.

FIG. 17 shows a comparison of the basal and induced activities of the CYP2B6 on LO. Ordinate: Activity of CYP2B6 induced by Phenobarbital (Induced condition—500 μM) or CITCO (Induced condition—1 μM). Normalized value to 1 μg of RNA. Abscissa (from left to right): (i) Basal condition on short-term cell maintenance; (ii) Induced condition with Phenobarbital on short-term cell maintenance; (iii) Induced condition with CITCO on short-term cell maintenance; (iv) Basal condition on long-term cell maintenance; (v) Induced condition with Phenobarbital on long-term cell maintenance; (vi) Induced condition with CITCO on long-term cell maintenance.

DETAILED DESCRIPTION

Definitions

Figure 1A:
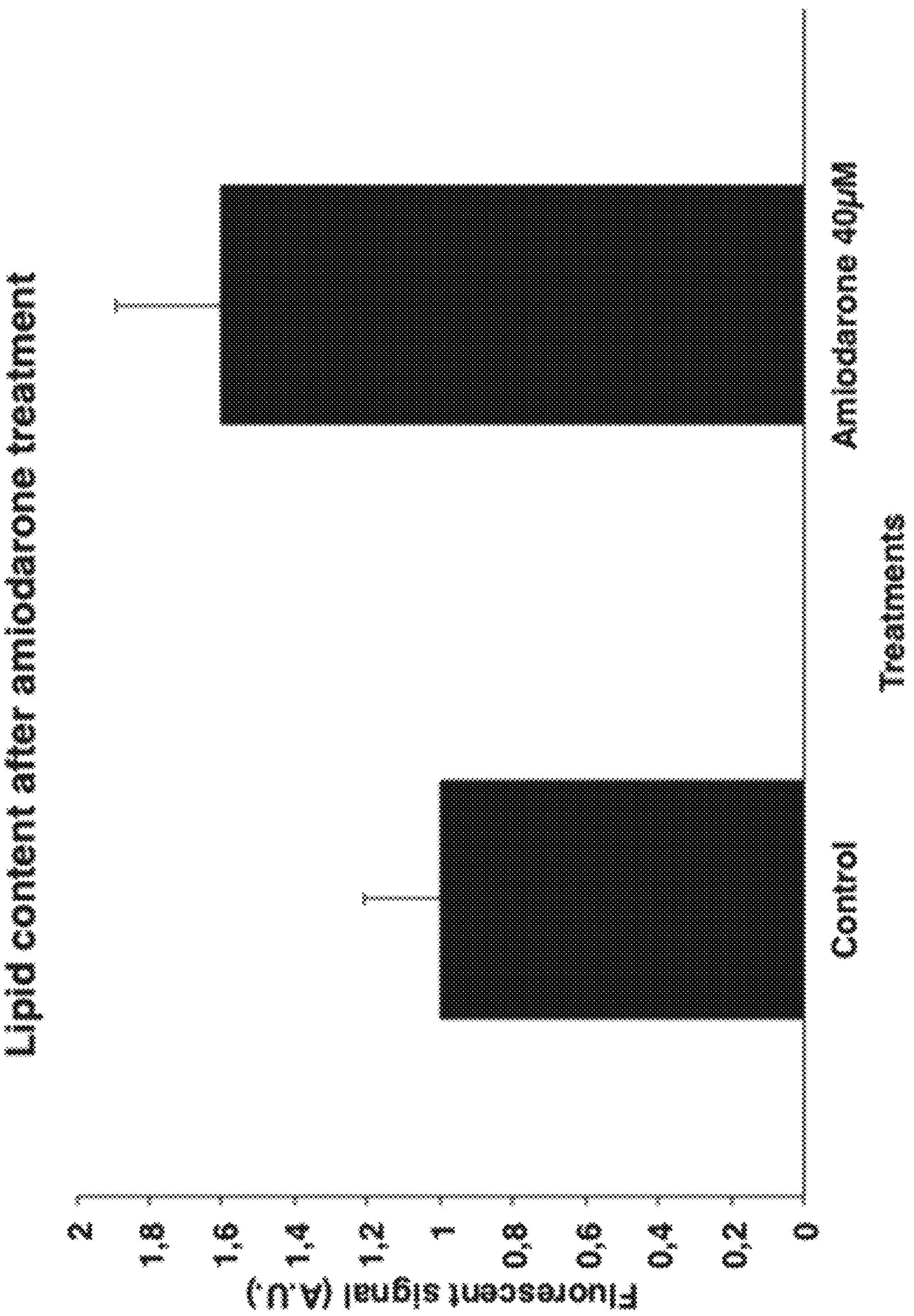
FIG. 1A: Ordinate: Fluorescence signal (A.U.) of lipids into LO. Abscissa: (i) Control (DMSO 0.1%); (ii) Amiodarone 40 μM. * p-value <0.001.

The terms used in this specification generally have their ordinary meanings in the art. Certain terms are discussed below, or elsewhere in the present disclosure, to provide additional guidance in describing the products and methods of the presently disclosed subject matter.

The following definitions apply in the context of the present disclosure.

As used herein, “3D-porous scaffold” intends to refer a matrix made of biomaterials, such as polymeric biomaterials, and providing a structural support for cell attachment and tissue development. Scaffolds allow recapitulation of the extracellular environment of cells, the ECM (Extracellular Matrix), by providing attachment sites and the ability for cells to grow in 3D shape. 3D-porous scaffolds may be made of various natural and synthetic polymers, recombinant proteins, ceramics, and metal-composite materials.

As used in this specification and the appended claims, the singular forms “a”, “an” and “the” include plural referents unless the content clearly dictates otherwise.

The term “about” or “approximately” means within an acceptable error range for the particular value as determined by one of ordinary skill in the art, which will depend in part on how the value is measured or determined, e.g., the limitations of the measurement system. For example, “about” can mean within 1 or more than 1 standard deviation, per the practice in the art. Alternatively, “about” can mean a range of up to 20%, or up to 10%, or up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term “about” meaning within an acceptable error range for the particular value should be assumed.

It is understood that aspects and embodiments of the present disclosure described herein include "comprising," "having," "consisting of," and "consisting essentially of" aspects and embodiments. The words "have" and "comprise," or variations such as "has," "having," "comprises," or "comprising," will be understood to imply the inclusion of the stated element(s) (such as a composition of matter or a method step) but not the exclusion of any other elements. The term "consisting of" implies the inclusion of the stated element(s), to the exclusion of any additional elements. The term "consisting essentially of" implies the inclusion of the stated elements, and possibly other element(s) where the other element(s) do not materially affect the characteristic(s) of the stated elements. It is understood that the different embodiments of the disclosure using the term "comprising" or equivalent cover the embodiments where this term is replaced with "consisting of" or "consisting essentially of".

As used herein the term "days" consists of a space of time that elapses over a period of 24 hours, i.e., from 0:00 in the morning. to 12:00 in the evening.

As used herein the term "drug development" refers to a process for identifying and selecting a drug candidate for development of novel drug for use in the treatment of a given disease. Specifically, a drug candidate is tested with different experiments to gather information on i) the absorption, distribution, metabolization, and excretion profile of the tested drug candidate; ii) the potential benefits and mechanisms of action of the tested drug candidate; iii) the most effective dosage to achieve an effect of the tested drug candidate; iv) the potential level of toxicity of the tested drug candidate; v) the interaction of the tested drug candidate with other drug compounds and treatments; and vi) the effectiveness of the tested drug candidate as compared with similar drug compounds on the given disease.

As used herein the term "drug discovery screen" refers to a process of selecting, within a library of potential drug candidates, a drug candidate able to bind with a biological target involved in the outcome of a given disease, the binding of the drug candidate with the biological target being able to result in an improvement of the outcome of the given disease in a patient in need thereof.

As used herein, the term "embryonic stem cells (ESCs)" also commonly abbreviated as ES cells, refers to cells that are pluripotent and derived from the inner cell mass of the blastocyst, an early-stage embryo. For purpose of the present invention, the term "ESCs" is used broadly sometimes to encompass the embryonic germ cells as well.

As used herein, the term "induced pluripotent stem cells (iPSCs)" also commonly abbreviated as iPS cells, refers to a type of pluripotent stem cells artificially derived from a normally non-pluripotent cell, such as an adult somatic cell, by inducing a "forced" expression of certain genes. hiPSC refers to human iPSCs.

As used herein, the term "hypoxic" used with respect to cell culture conditions refers to a cell culture condition in which the amount of oxygen provided to the cultured cells is below an amount of oxygen that would be required to ensure a consumption of oxygen adapted to a normal metabolism of the cells. Hypoxic culture conditions may be obtained by culturing the cells under a reduced oxygen saturation pressure, or cells may be treated with compounds that mimic hypoxia, for instance such as cobalt chloride. Determining oxygen levels that define a hypoxic condition in cell culture is well within the skill person in the art. For instance, Zeitouni et al. (*Hypoxia* (*Auckl*). 2015; 3:53-66) disclosed a suitable method of real-time oxygen measurements. As example of hypoxic conditions for cell culture, one may cite conditions where the atmosphere may contain about 5% $CO_2$ and from about 2% to about 10% of $O_2$, for example from about 3% to about 5% of $O_2$, and for example of about 4% of $O_2$.

As used herein, the term "liver organoid" (LO) refers independently to a liver organoid obtained by the method for preparing a liver organoid as described herein and to a liver organoid in a three-dimensional porous scaffold as described herein.

As used herein the term "normoxic" used with respect to cell culture conditions refers to a cell culture condition in which the amount of oxygen provided to the cultured cells is within the range of amounts of oxygen required to ensure a consumption of oxygen adapted to a normal metabolism of the cells. Normoxic culture conditions may be obtained by culturing the cells under an oxygen saturation pressure ensuring appropriate oxygen consumption by the cultured cells. As example of normoxic conditions in cell culture one may cite conditions where the atmosphere may contain about 5% $CO_2$ and from about 15% to about 25% of $O_2$, for example from about 18% to about 22% of $O_2$, and for example of about 20% of $O_2$.

The term "organoids" refers to an in vitro 3-dimensional population of cells which resemble the vertebrate, mammalian, or human organ. An organoid satisfies the following criteria: 1) contains multiple cell types of the organ, 2) different cell types are spatially organized into structures that resemble the organ tissue, 3) organoids should perform organ specific functions in vitro.

As used herein, the term "pluripotent stem cells (PSCs)" encompasses any cells that can differentiate into nearly all cell types of the body, i.e., cells derived from any of the three germ layers (germinal epithelium), including endoderm (interior stomach lining, gastrointestinal tract, the lungs), mesoderm (muscle, bone, blood, urogenital), and ectoderm (epidermal tissues and nervous system). PSCs can be the descendants of inner cell mass cells of the preimplantation blastocyst or obtained through induction of a non-pluripotent cell, such as an adult somatic cell, by forcing the expression of certain genes. Pluripotent stem cells can be derived from any suitable source. Examples of sources of pluripotent stem cells include mammalian sources, including human, rodent, porcine, and bovine.

As used herein the term "regenerative medicine" refers to the technologies aiming to repair or replace damaged, diseased, or metabolically deficient organs, tissues, and cells via tissue engineering; cell transplantation; and artificial organs and bioartificial organs and tissues.

Within the disclosure, the term "significantly" used with respect to a change intends to mean that the observed change is noticeable and/or it has a statistic meaning.

As used herein, the term "totipotent stem cells" (also known as omnipotent stem cells) are stem cells that can differentiate into embryonic and extra-embryonic cell types. Such cells can construct a complete, viable organism. These cells are produced from the fusion of an egg and sperm cell. Cells produced by the first few divisions of the fertilized egg are also totipotent.

As used herein, in the context of an immune response elicitation, the terms "treat", "treatment", "therapy" and the like refer to the implantation of a liver organoid or a composition comprising a liver organoid as disclosed herein with the purpose to cure, heal, alleviate, relieve, alter, remedy, ameliorate, improve, or affect a disease or a disorder, the symptoms of the condition, or to prevent or delay the onset of the symptoms, complications, or otherwise arrest or inhibit further development of the disorder in a statistically significant manner. In exemplary embodiments, the diseases, disorders or conditions considered herein are liver or hepatic diseases, disorders or conditions, such as non-alcoholic steatohepatitis or alcoholic steatohepatitis.

As used herein the term "toxicity assay" refers to the toxicological prescreening phase of the development of chemicals (biotransformation, mechanistic) used to determine the toxicity of a substance to living systems. These include tests on clinical drugs, food supplements, and environmental pollutants.

Cell Culture Media, Media Supplements and Cytokines

A method as disclosed herein implements a set of cell culture media suitable for growing and differentiating the isolated stem cells into a liver organoid.

The cell culture media useable may be completed with different medium supplements, growth factors, cytokines, inhibitory and/or activating molecules intended to stimulate the growth and the viability of the cells, as well as the differentiation of the stem cells into somatic cells of the liver organoids.

Cell culture media typically contain a large number of ingredients, which are necessary to support maintenance of the cultured cells. Suitable combinations of ingredients can readily be formulated by the skilled person. A culture medium to be used herein will generally be a nutrient solution comprising standard cell culture ingredients, such as amino acids, vitamins, inorganic salts, a carbon energy source, and a buffer, as described in the art.

A cell culture medium useable in the methods disclosed herein may be formulated in deionized, distilled water. A culture medium may be sterilized prior to use to prevent contamination, e.g., by ultraviolet light, heating, gamma-irradiation, or filtration. A cell culture medium may be frozen (e.g., at −20° C. or −80° C.) for storage or transport. The medium may contain one or more antibiotics to prevent contamination. The medium may have an endotoxin content of less than 0.1 endotoxin units per ml, or may have an endotoxin content less than 0.05 endotoxin units per ml. Methods for determining the endotoxin content of culture media are known in the art.

In one exemplary embodiment, a cell culture medium may be a defined synthetic medium that is buffered at a pH of 7.4 (preferably with a pH 7.2-7.6 or at least 7.2 and not higher than 7.6) with a carbonate-based buffer, while the cells are cultured in an atmosphere comprising between 5% and 10% $CO_2$, or at least 5% and not more than 10% $CO_2$, for example 5% $CO_2$.

A skilled person will understand from common general knowledge the types of culture media that might be used for as the basal medium in the cell culture mediums to be used in the methods disclosed herein.

The cell culture media to be used in the different steps of the methods disclosed may be identical or different. Identical cell culture media may have the same basic components but may be supplemented with different supplements such as nutrients, cytokines, growth factors, hormones. Different cell culture media have different basic components. They may be supplemented with different or identical supplements.

As example, cell culture media used in the different stages of steps a) to c) may be identical. They may be supplemented differently. The cell culture media used in the different stages of step d) may identical. They also may be supplemented differently. The cell culture media implemented in steps a) to c) may be different from the cell culture media implemented in step d).

Potentially suitable cell culture media are available commercially, and include, but are not limited to, Dulbecco's Modified Eagle Media (DMEM), Minimal Essential Medium (MEM), Knockout-DMEM (KO-DMEM), Glasgow Minimal Essential Medium (G-MEM), Basal Medium Eagle (BME), DMEM/Ham's F12, Advanced DMEM/Ham's F12, Iscove's Modified Dulbecco's Media (IMDM), Ham's F-10, Ham's F-12, Medium 199, RPMI 1640 Media, and Hepatocyte cell culture media.

An exemplary cell culture medium may be RPMI 1640 supplemented with glutamine, insulin, Penicillin/streptomycin, and transferrin. In another embodiment, Advanced RPMI 1640 may be used, which is optimized for serum free culture and already includes insulin. In this case, Advanced RPMI medium may be supplemented with glutamine and Penicillin/streptomycin.

As cell culture media useable in the methods disclosed herein one may refer to RPM1640, Hepatocyte cell culture media or DMEM/Ham's F12.

A cell culture medium of steps a) to c) may be RPMI 1640 or DMEM/Ham's F12, in particular may be RPMI 1640, optionally supplemented with B27 or N-2 supplement, and/or a cell culture medium of step d) may be a hepatocyte cell culture medium without endothelial growth factor.

A cell culture medium of steps a) to c) may be RPMI 1640 or DMEM/Ham's F12, optionally supplemented with B27 or N-2 supplement.

A cell culture medium of steps a) to c) may be RPMI 1640, optionally supplemented with B27 or N-2 supplement. In one exemplary embodiment, a cell culture medium of steps a) to c) may be RPMI 1640, optionally supplemented with B27.

A cell culture medium of steps a) to c) may be RPMI 1640 supplemented with B27.

A cell culture medium of step d) may be a hepatocyte cell culture medium without endothelial growth factor.

The cell culture media useable in the methods disclosed herein may be supplemented with growth and maintenance medium supplements, cytokines, inhibitory and/or activating molecules.

In some embodiments, a cell culture medium may be supplemented with a purified, natural, semi-synthetic and/or synthetic growth factor and does not comprise an undefined component such as fetal bovine serum or fetal calf serum. Various different serum replacement formulations are commercially available and are known to the skilled person. Where a serum replacement is used, it may be used at between about 1% and about 30% by volume of the medium, according to conventional techniques.

It is understood herein that, except otherwise explicated, the amounts of supplements, cytokines or other molecules indicated herein as supplement of the cell culture media are the amount in the cell medium culture when added to the cultured cells. The amount may decrease in the cell culture over time as the cytokines, molecules or supplements are metabolized by the cells. When the cell culture medium is renewed in the cell culture, the renewed cell culture medium may comprise a renewed amount of cytokines, supplements, or molecules.

As supplement for growth and viability of the cells useable in the cell culture media disclosed herein may be a serum-free supplement. As example of cell culture media supplement useable in the methods disclosed herein one may cite B27 or N-2 supplement.

B27 is a well-known in the art cell culture medium supplement which is used to stimulate the growth and maintain the viability of cultured cells, such as stem cells or somatic cells. B27 contains vitamins, such as biotin, DL-alpha-tocopherol acetate, DL-alpha-tocopherol, and vitamin A (acetate), proteins, such as BSA, fatty acid free fraction V, catalase, human recombinant insulin, human transferrin, and superoxide dismutase, and other components, such as corticosterone, D-galactose, ethanolamine HLC, glutathione (reduced), L-carnitine HLC, linoleic acid, linolenic acid, progesterone, putrescine 2HLC, sodium selenite, and T3 (triodo-L-thyronine).

'B27 Supplement' is described in Brewer et al. (J Neurosci Res., 35(5):567-76, 1993) and may be available from Invitrogen, Carlsbad, CA; www.invitrogen.com; currently catalog no. 17504-044; and from PAA Laboratories GmbH, Pasching, Austria; www.paa.com; catalog no. F01-002.

N-2 supplement is a chemically-defined, serum-free supplement based on Bottenstein's N-1 formulation (Bottentstein, 1985, Cell culture in the Neuroscience). N-2 supplement contains human transferrin (holo), insulin recombinant full chain, progesterone, putrescine, and selenite. It may be available from various commercial source, for example from Fisher Scientific under the reference Gibco™ 17502048.

As examples of growth factors which may be used to complemented cell culture media or media supplements, one may mention insulin and the related insulin-like growth factors, such as the insulin-like growth factors I and II, the relaxins, and the insulin-like proteins (INSL3, 4, 5 and 6).

In one embodiment, insulin may be used to complement a cell culture media, such as RPMI 1640, or a supplement such as previously indicated, such as B27.

Insulin may be used in an amount ranging from about 10 nM to about 100 nM, for example from about 30 nM to about 130 nM, for example from about 50 nM to about 160 nM, or for example at about 60 nM.

In one embodiment, a cell culture medium useable in a method disclosed herein may comprise a SMAD2/3 pathway activator.

As example of SMAD2/3 pathway activator one may mention Activin A, NODAL, TGFβ1, TGFβ2 or TGFβ3.

In one embodiment, a SMAD2/3 pathway activator may be Activin A.

The SMAD2/3 pathway is solicited by the TGF-β/Activin/Nodal signaling. The Activin/Nodal signaling, through the TGF-β receptors and its effector SMAD2/3, initiates mesendoderm differentiation. Highly activated Activin/Nodal signal results in definitive endoderm differentiation.

Activin A is a member of the transforming growth factor beta (TGF-β) family of proteins produced by different cell types throughout development (Kaneko, Handbook of Hormones, Academic Press, 2016, Pages 295-e33B-2). It is a disulfide-linked homodimer (two beta-A chains) that binds to heteromeric complexes of a type I (Act RI-A and Act RI-B) and a type II (Act RII-A and Act RII-B) serine-threonine kinase receptor. Activins signal through SMAD2/3 proteins to regulate a variety of functions, including cell proliferation, differentiation, wound healing, apoptosis, and metabolism. Activin A facilitates differentiation of human embryonic stem cells into definitive endoderm. Activin A may maintain self-renewal capacity and pluripotency of stem cells. However, high concentrations of Activin A may induce efficient differentiation of stem cells towards definitive endoderm, such as 50-100 ng/ml, whereas 5 ng/ml Activin A may be supportive of maintenance of stem cells pluripotency.

Transforming growth factor-β (TGF-β) is a multifunctional cytokine (Sporn and Roberts, *Nature* (London), 332: 217-219, 1988), and plays a regulatory role in cellular growth, differentiation, and extracellular matrix protein synthesis (Madri et al., *J Cell Biology,* 106: 1375-1384, 1988). TGF-β receptors are single pass serine/threonine kinase receptors and belong to the transforming growth factor beta family of proteins. TGF-β also plays a crucial role in stem cell differentiation (Massagué J, Xi Q. *FEBS Lett.* 2012; 586(14):1953-1958). TGF-β exists in three known subtypes in humans, TGFβ1, TGFβ2, and TGFβ3. High concentrations of TGF-β, in particular TGFβ1, TGFβ2, or TGFβ3, may induce efficient differentiation of stem cells towards definitive endoderm, such as 50-100 ng/ml, whereas 5 ng/ml TGF-β may be supportive of maintenance of stem cells pluripotency.

In some embodiments TGF-β is selected from the group comprising TGFβ1, TGFβ2, and TGFβ3.

NODAL is a secretory protein that is a member of the transforming growth factor beta (TGF-β) superfamily of proteins. NODAL is involved in cell differentiation in early embryogenesis, playing a key role in signal transfer from the node, in the anterior primitive streak, to lateral plate mesoderm (LPM). NODAL plays a role in differentiation of human embryonic stem cells into definitive mesoderm and endoderm. NODAL also has functions in neural patterning and may maintain pluripotency of stem cells (Shen, 2007. *Development.* 134 (6): 1023-34). Specifically, high concentrations of NODAL may induce efficient differentiation of stem cells towards definitive endoderm, such as 50-100 ng/ml, whereas 5 ng/ml of NODAL may be supportive of maintenance of stem cells pluripotency.

When present in a cell culture medium, a SMAD2/3 pathway activator, such as Activin A, may be used in an amount ranging from 50 ng/ml to about 2 000 ng/ml, for example from about 60 ng/ml to about 1 500 ng/ml, for example from about 70 ng/ml to about 1 200 ng/ml, for example from about 80 ng/ml to about 1 100 ng/ml, for example from about 100 ng/ml to about 1 000 ng/ml. For example, a SMAD2/3 pathway activator, such as Activin A, may be used in an amount of about 100 ng/ml. For example, a SMAD2/3 pathway activator, such as Activin A, may be used in an amount of about 1 000 ng/ml.

In one embodiment, a cell culture medium useable in a method disclosed herein may comprise a fibroblast growth factor (FGF).

Fibroblast growth factors (FGFs) are a family of growth factors involved in angiogenesis, wound healing, and embryonic development. The FGFs are heparin-binding proteins and interactions with cell-surface associated heparan sulfate proteoglycans have been shown to be essential for FGF signal transduction. Suitable FGF pathway activators will be readily understood by one of ordinary skill in the art. Exemplary FGF pathway activators include but are not limited to: one or more molecules selected from the group consisting of FGF1, FGF2, FGF3, FGF4, FGF10, FGF11, FGF12, FGF13, FGF14, FGF15, FGF16, FGF17, FGF18, FGF19, FGF20, FGF21, FGF22, and FGF23. In some embodiments, siRNA and/or shRNA targeting cellular constituents associated with the FGF signaling pathway may be used to activate these pathways.

In one embodiment a fibroblast growth factor which may be used in a method as disclosed herein may be the FGF2 (fibroblast growth factor 2). FGF-2 is a basic heparin binding growth factor. It is also referred to as BFGF (basic fibroblast growth factor). It interacts with FGFR1 (fibroblast growth factor receptor 1), FGFR2 and FGFR3. FGF2 stimulates the proliferation of a wide variety of cells including mesenchymal, neuroectodermal and endothelial cells. FGF2 may induce the formation of the hepatic endoderm. Recombinant human FGF-2 may be a 17.2 kDa protein containing 154 amino acid residues.

When present in a cell culture medium, a FGF, as for example FGF2, may be used at a concentration ranging from about 10 ng/ml to about 500 ng/ml, for example from about 20 ng/ml to about 200 ng/ml, for example from about 30 ng/ml to about 80 ng/ml, or for example from about 40 ng/ml to about 50 ng/ml.

In one embodiment, a cellule culture medium used herein may comprise a bone morphogenetic protein (BMP).

Bone morphogenetic proteins (BMPs) are secreted signaling molecules belonging to the transforming growth factor-β (TGF-β) superfamily of growth factors and playing a fundamental role in the regulation of bone organogenesis through the activation of receptor serine/threonine kinases. BMPs have been shown to be key regulators of embryogenesis and are known to play a role in the growth and differentiation of various cell types, including embryonic stem (ES) cells, induced pluripotent stem (iPS) cells, mesenchymal cells, epithelial cells, hematopoietic cells, and neuronal cells. As examples of BMPs one may cite BMP4, BMP2, BMP3, BMP5, BMP6, and BMP7. BMPs are disulfide-linked homodimer or heterodimer proteins. As exemplary of BMP one may cite BMP-4. BMP4 consisting of two 116-amino-acid residue subunits. BMP-4 binds to type I and type II receptors resulting in phosphorylation of receptor 1, which in turn results in the phosphorylation of Smad proteins, which then go on to act as transcription factors.

When present in a cell culture medium, a BMP, as for example BM4, may be used at a concentration ranging from about 5 ng/ml to about 300 ng/ml, for example from about 10 ng/ml to about 200 ng/ml, for example from about 15 ng/ml to about 150 ng/ml, or for example from about 20 ng/ml to about 100 ng/ml.

In one embodiment, a cell culture medium useable in a method disclosed herein may comprise a vascular endothelial growth factor (VEGF) or a VEGF-like factor.

The vascular endothelial growth factor, also known as vasculotropin, is an angiogenic growth factor, which is heat and acid stable. Vascular endothelial growth factors (VEGFs) are a family of secreted polypeptides with a highly conserved receptor-binding cystine-knot structure similar to that of the platelet-derived growth factors. VEGFs stimulate endothelial cell growth, angiogenesis, and capillary permeability. VEGF is a secreted homodimer, heparin-binding glycoprotein,1 which has an isoelectric point of 8.5. VEGF promotes the growth of vascular endothelial cells. VEGF-A, the founding member of the family, is highly conserved between animals and is the prototypical member of a family of related growth factors that includes placental growth factor (PLGF), VEGF-B, VEGF-C, and VEGF-D (also known as c-Fos-induced growth factor, FIGF), and the viral VEGF-Es encoded by strains D1701, NZ2 and NZ7 of the parapoxvirus Orf.

When present in a cell culture medium, a VEGF may be used at a concentration ranging from about 100 ng/ml to about 400 ng/ml, for example from about 120 ng/ml to about 360 ng/ml, for example from about 140 ng/ml to about 320 ng/ml, for example from about 160 ng/ml to about 280 ng/ml, for example from about 180 ng/ml to about 240 ng/ml, or for example at about 200 ng/ml.

In one embodiment, a cell culture medium useable in a method disclosed herein may comprise a hepatocyte growth factor (HGF) or a HGF-like factor.

The hepatocyte growth factor is a pleiotropic growth factor that promotes proliferation, motility, survival, and differentiation. HGF binds and promotes the dimerization and activation of the receptor tyrosine kinase c-MET, and stimulates PI3K/AKT, FAK, JNK, and ERK1/2 signaling. HGF stimulates migration of cells during embryogenesis, induces cell motility and scattering of epithelial cells, and regulates epithelial-mesenchymal transition.

When present in a cell culture medium, HGF may be used at a concentration ranging from about 50 ng/ml to about 200 ng/ml, for example from about 60 ng/ml to about 180 ng/ml, for example from about 70 ng/ml to about 160 ng/ml, for example from about 80 ng/ml to about 140 ng/ml, for example from about 90 ng/ml to about 120 ng/ml, or for example at about 100 ng/ml.

In one embodiment, a cell culture medium useable in a method disclosed herein may comprise an inhibitor of the TGF-β/Activin/NODAL pathway.

As examples of inhibitors of the TGF-β/Activin/NODAL pathway one may cite SB431542.

SB431542 is a selective and potent inhibitor of the TGF-β/Activin/NODAL pathway that inhibits ALK5, ALK4, and ALK7 by competing for the ATP binding site. It inhibits the self-renewal and causes differentiation of human pluripotent stem cells (PSCs).

When present in a cell culture medium, a TGF-β/Activin/NODAL pathway inhibitor, such as SB431542, may be used at a concentration ranging from about 1 μg/ml to about 20 μg/ml, for example from about 3 μg/ml to about 18 μg/ml, for example from about 5 μg/ml to about 16 μg/ml, for example from about 7 μg/ml to about 14 μg/ml, for example from about 8 μg/ml to about 12 μg/ml, or for example at about 10 μg/ml.

In one embodiment, a cell culture medium useable in a method disclosed herein may comprise an interleukin (IL)-6 cytokine family activator.

As examples of interleukin (IL)-6 cytokine family activators one may cite Oncostatin M (OSM), Leukemia inhibitory factor (LIF), Granulocyte-Colony Stimulating Factor (G-CSF), IL-6, and (Ciliary neurotrophic factor) CNTF.

Oncostatin M (OSM), LIF, G-CSF, IL-6, and CNTF are structurally related members of the same cytokine family sharing similarities in their primary amino acid sequences, predicted secondary structure, and receptor components. OSM is a growth-regulating cytokine, affecting a number of tumor and normal cells. It induces an increase in LDL receptor expression and LDL uptake by hepatoma cells.

When present in a cell culture medium, a TGF-β/Activin/NODAL pathway inhibitor, such as Oncostatin M, may be used at a concentration ranging from about 100 ng/ml to about 400 ng/ml, for example from about 120 ng/ml to about 360 ng/ml, for example from about 140 ng/ml to about 320 ng/ml, for example from about 160 ng/ml to about 280 ng/ml, for example from about 180 ng/ml to about 240 ng/ml, or for example at about 200 ng/ml.

In one embodiment, a cell culture medium useable in a method disclosed herein may comprise a steroid.

As examples of steroids useable herein one may cite the corticosteroids. As corticosteroids useable herein, one may cite the glucocorticoids, such as dexamethasone, betamethasone, fludrocortisone acetate, methylprednisolone, prednisone, or prednisolone or triamcinolone.

Dexamethasone is a synthetic glucocorticoid, similar to the natural glucocorticoid hydrocortisone, but has an increased affinity for glucocorticoid receptors when compared to the natural hydrocortisone ligand. Dexamethasone is known as promoting the differentiation of stem cells in hepatocytes.

When present in a cell culture medium, a steroid, such as dexamethasone, may be used at a concentration ranging from about 0.1 μM to about 10 μM, for example from about 0.2 μM to about 8 μM, for example from about 0.4 μM to about 5 μM, for example from about 0.6 μM to about 3 μM, for example from about 0.8 μM to about 2 μM, or for example at about 1 μM.

In one exemplary embodiment, the SMAD2/3 pathway activator may be Activin A, the fibroblast growth factor may be FGF2, the bone morphogenetic protein may be BMP4, the TGF-β/Activin/NODAL pathway inhibitor may be SB431542, the interleukin (IL)-6 cytokine family activator may be Oncostatin M, and the steroid may be dexamethasone.

In a first step of the methods disclosed herein, the stem cells are cultured with a first set of cell culture media, comprising for example at least a first and a second cell culture medium, and under normoxic condition suitable for differentiating the cells in definitive endoderm cells. This step may comprise a first phase of culturing the cells in a first cell culture medium comprising a SMAD2/3 pathway activator, a fibroblast growth factor, and a bone morphogenetic protein. This step may comprise a second phase following the first phase. The second phase of culturing the cells may comprise contacting the cells with a second cell culture medium comprising a SMAD2/3 pathway activator. The second cell culture medium may be devoid of fibroblast growth factor and/or of bone morphogenetic protein. In one exemplary embodiment, the second cell culture medium is devoid of fibroblast growth factor and/or of bone morphogenetic protein. This first step is carried out under normoxic conditions, for example 20% $O_2$ and 5% $CO_2$.

In one exemplary embodiment, a cell culture medium useable as first and/or second cell culture media may be RPM1640 or DMEM/Ham's F12.

In one embodiment, a cell culture medium useable as a first and/or second cell culture media may be supplemented with a serum-free supplement for growth and viability of the cells. In one exemplary embodiment, a supplement useable in a first and/or second cell culture media may be B27.

In one embodiment, a cell culture medium useable as a first and/or second cell culture media may be supplemented with a growth factor, for example from the insulin growth factor family, such as the insulin.

In one exemplary embodiment, a first and/or second cell culture media may be RPM1640 supplemented with B27 and insulin.

In one exemplary embodiment, a first and/or second cell culture media may comprise a SMAD2/3 pathway activator, as for example Activin A.

In one embodiment, a first cell culture medium may comprise a SMAD2/3 pathway activator, as for example Activin A, in an amount ranging at about 90 to 110 ng/ml, for example at about 100 ng/ml.

In one embodiment, a second cell culture medium may comprise a SMAD2/3 pathway activator, as for example Activin A, in an amount ranging at about 900 to 1 100 ng/ml, for example at about 1 000 ng/ml.

In one exemplary embodiment, a first cell culture medium may comprise a FGF, as for example a FGF2, in an amount ranging at about 30 to 50 ng/ml, for example at about 40 ng/ml.

In one exemplary embodiment, a first cell culture medium may comprise a BMP, as for example a BMP4, in an amount ranging at about 10 to 30 ng/ml, for example at about 20 ng/ml.

In a second step of the methods disclosed herein, the cells are cultured with a second set of cell culture media, comprising for example at least a third cell culture medium, and under hypoxic condition suitable for differentiating the cells in hepatic endoderm cells. This step comprises a phase of culturing the cells in a third cell culture medium comprising a fibroblast growth factor, a vascular endothelial growth factor, and a bone morphogenetic protein. This second step is carried out under hypoxic conditions, for example 4% $O_2$ and 5% $CO_2$.

In one exemplary embodiment, a cell culture medium useable as third cell culture media may be RPMI 1640 or DMEM/Ham's F12.

In one embodiment, a cell culture medium useable as a third cell culture media may be supplemented with a serum-free supplement for growth and viability of the cells. In one exemplary embodiment, a supplement useable in a third cell culture media may be B27.

In one embodiment, a cell culture medium useable as a third cell culture media may be supplemented with a growth factor, for example from the insulin growth factor family, such as the insulin.

In one exemplary embodiment, a third cell culture media may be RPM1640 supplemented with B27 and insulin.

In one exemplary embodiment, a third cell culture medium may comprise a FGF, as for example a FGF2, in an amount ranging at about 40 to 60 ng/ml, for example at about 50 ng/ml.

In one exemplary embodiment, a third cell culture medium may comprise a VEGF, in an amount ranging at about 190 to 210 ng/ml, for example at about 200 ng/ml.

In one exemplary embodiment, a third cell culture medium may comprise a BMP, as for example a BMP4, in an amount ranging at about 90 to 110 ng/ml, for example at about 110 ng/ml.

In a third step of the methods disclosed herein, the cells are cultured with a third set of cell culture media, comprising for example at least a fourth, a fifth, and/or a sixth cell culture medium, and under hypoxic condition suitable for differentiating the cells in hepatic progenitor cells. This step comprises a first phase of culturing the cells in a fourth cell culture medium comprising a hepatocyte growth factor, and an inhibitor of the TGF-β/Activin/NODAL pathway. This step may comprise a second phase following the first phase. The second phase of culturing the cells may comprise contacting the cells with a fifth cell culture medium comprising a hepatocyte growth factor. The fifth cell culture medium may be devoid of inhibitor of the TGF-β/Activin/NODAL pathway. This step may comprise a third phase following the second phase. The third phase of culturing the cells may comprise contacting the cells with a sixth cell culture medium comprising a hepatocyte growth factor and an interleukin (IL)-6 cytokine family activator. The sixth cell culture medium may be devoid of inhibitor of the TGF-β/Activin/NODAL pathway. This third step is carried out under hypoxic conditions, for example 4% $O_2$ and 5% $CO_2$.

In one exemplary embodiment, a cell culture medium useable as a fourth, a fifth, and/or a sixth cell culture medium may be RPMI 1640 or DMEM/Ham's F12.

In one embodiment, a cell culture medium useable as a fourth, a fifth, and/or a sixth cell culture medium may be supplemented with a serum-free supplement for growth and viability of the cells. In one exemplary embodiment, a supplement useable in a third cell culture media may be B27.

In one embodiment, a cell culture medium useable as a fourth, a fifth, and/or a sixth cell culture medium may be supplemented with a growth factor, for example from the insulin growth factor family, such as the insulin.

In one exemplary embodiment, the fourth, fifth, and sixth cell culture media may be RPMI 1640 supplemented with B27 and insulin.

In one exemplary embodiment, a fourth, a fifth, and/or a sixth cell culture medium may comprise a HGF in an amount ranging at about 90 to 110 ng/ml, for example at about 100 ng/ml.

In one exemplary embodiment, a fourth cell culture medium may comprise a TGF-β/Activin/NODAL pathway inhibitor, such as SB431542, in an amount ranging at about 9 to 11 μg/ml, for example at about 10 μg/ml. Advantageously, it has been observed that the combination of an inhibitor of the TGFβ pathway, SB431542 with an activator of the Wnt pathway, HGF was promoting a better differentiation of the cells into hepatoblasts.

A fifth cell culture medium may be supplemented with HGF in an amount ranging at about 90 to 110 ng/ml, for example at about 100 ng/ml.

In one exemplary embodiment, a sixth cell culture medium may comprise an interleukin (IL)-6 cytokine family activator, such as Oncostatin M (OSM), in an amount ranging at about 15 to 25 ng/ml, for example at about 20 ng/ml.

In one embodiment, a fourth cell culture medium is devoid of interleukin (IL)-6 cytokine family activator. In one embodiment, a fifth cell culture medium is devoid of TGF-β/Activin/NODAL pathway inhibitor and/or interleukin (IL)-6 cytokine family activator. In one embodiment, a sixth cell culture medium is devoid of TGF-β/Activin/NODAL pathway inhibitor.

In a fourth step of the methods disclosed herein, the cells are cultured with a fourth set of cell culture media, comprising for example at least a seventh, an eighth, and a ninth cell culture medium, and under normoxic condition suitable for differentiating the cells in liver organoids. This step comprises a first phase of culturing the cells in a seventh cell culture medium comprising a hepatocyte growth factor, an interleukin (IL)-6 cytokine family activator, and a steroid. This step may comprise a second phase following the first phase. The second phase of culturing the cells may comprise contacting the cells with an eighth cell culture medium comprising a hepatocyte growth factor, and a steroid. The eighth cell culture medium may be devoid of an interleukin (IL)-6 cytokine family activator. This step may comprise a third phase following the second phase. The third phase of culturing the cells may comprise contacting the cells with a ninth cell culture medium. The ninth cell culture medium may be devoid of hepatocyte growth factor, interleukin (IL)-6 cytokine family activator, and/or steroid. In exemplary embodiment, the ninth cell culture medium may be devoid of hepatocyte growth factor, interleukin (IL)-6 cytokine family activator, and steroid.

The fourth step is carried out under normoxic conditions, for example 20% $O_2$ and 5% $CO_2$.

In one exemplary embodiment, the seventh, the eighth, and/or the ninth cell culture media are a hepatocyte cell culture medium.

In one embodiment, the hepatocyte cell culture medium is devoid of endothelial growth factor. In one embodiment, the hepatocyte cell culture medium is devoid of B27.

In one embodiment, a seventh cell culture medium may comprise a HGF in an amount ranging at about 90 to 110 ng/ml, for example at about 100 ng/ml. In one exemplary embodiment, a seventh cell culture medium is a hepatocyte cell culture medium comprising HGF.

In one embodiment, a seventh and/or an eighth cell culture medium may comprise an interleukin (IL)-6 cytokine family activator, such as Oncostatin M (OSM), in an amount ranging at about 190 to 210 ng/ml, for example at about 200 ng/ml. In one exemplary embodiment, the seventh and the eighth cell culture media are a hepatocyte cell culture medium comprising Oncostatin M (OSM).

In one embodiment, a seventh and/or an eighth cell culture medium may comprise a steroid, such as dexamethasone, in an amount ranging at about 0.5 μM to 1.5 μM, for example at about 1 μM. In one exemplary embodiment, the seventh and the eighth cell culture media are a hepatocyte cell culture medium comprising dexamethasone.

Advantageously, dexamethasone improves hepatocyte maturation by stopping hepatocyte proliferation. Furthermore, it has been observed that it acts in combination with OSM to improve the expression of hepatocyte genes such as albumin, Apo B, Apo (a), PCSK9 and CYP3A4.

In one embodiment, an eighth cell culture medium may be devoid of HGF.

In one embodiment, a ninth cell culture medium may be devoid of HGF and/or interleukin (IL)-6 cytokine family activator and/or steroid. In one exemplary embodiment, the ninth cell culture medium is a hepatocyte cell culture medium devoid of HGF and interleukin (IL)-6 cytokine family activator and steroid.

In one embodiment, methods disclosed herein may comprise a preliminary step, before the above indicated first step, of contacting the isolated stem cells in the scaffold with a tenth cell culture medium supplemented with a ROCK family pathway inhibitor.

This step may comprise a first phase of contacting the isolated stem cells in the scaffold with a tenth cell culture medium supplemented with a ROCK family pathway inhibitor followed by a second phase of contacting the isolated stem cells in the scaffold with a tenth cell culture medium not supplemented with a ROCK family pathway inhibitor.

This step may be carried out under hypoxic condition, for example 4% $O_2$ and 5% $CO_2$.

This step may be carried out after seeding the stem cells in the 3D-porous scaffold, and before any of the steps disclosed previously.

This step advantageously allows to trigger the differentiation of the stem cells in different hepatic cell lines.

In one exemplary embodiment, a tenth cell culture medium useable in such step may be RPM1640, DMEM/Ham's F12 or StemMACS iPS-Brew medium.

In one embodiment, such a tenth cell culture medium useable may be supplemented with a serum-free supplement for growth and viability of the cells. In one exemplary embodiment, a supplement useable in a tenth cell culture media may be B27.

In one embodiment, such a tenth cell culture medium may be supplemented with a growth factor, for example from the insulin growth factor family, such as the insulin.

In one exemplary embodiment, such a tenth cell culture media may be StemMACS iPS-Brew medium.

In one embodiment, the ROCK signaling pathway inhibitor may be selected from one or more of Y27632, HA1077, and H1152, in particular Y27632. A ROCK signaling pathway inhibitor may be used in a final concentration in the range of about 0.001 mM to about 0.1 mM, for example in the range of about 0.002 mM to about 0.08 mM, for example in the range of about 0.004 mM to about 0.06 mM, for example in the range of about 0.006 mM to about 0.04 mM, for example in the range of about 0.008 mM to about 0.02 mM, for example at about 0.01 mM.

3D-Porous Scaffolds

The methods disclosed herein are using three-dimensional porous scaffolds. A 3D cell culture allows cells in vitro to grow in all directions, similar to how they would in vivo.

Three-dimensional porous scaffolds are seeded with the stem cells. The stem cells may adhere on the inner parts of the scaffolds, growth, proliferate, migrate, and differentiate in the different somatic cell types which compose the liver organoids.

Three-dimensional (3D) porous scaffolds are known in the art. One may mention, for example, the 3D-Hydrogels produced by Sigma/Merck, the 3D-scaffold described in WO 2016/166479 A1, or the 3D-porous scaffold BIOMIMESYS® Liver sold by HCS Pharma.

A 3D-porous scaffold may be a hydrogel matrix mimicking natural ECM structure. Hydrogels are composed of interconnected pores with high water retention, which enables efficient transport of e.g., nutrients and gases. Several different types of hydrogels from natural and synthetic materials may be available for 3D cell culture, including e.g., animal ECM extract hydrogels, protein hydrogels, peptide hydrogels, polymer hydrogels, and wood-based nanocellulose hydrogel.

A 3D-porous scaffold which may be used to seed and differentiate stem cells in liver organoids may be comprised of hydrophilic polysaccharides, of proteins, and/or of synthetic polymers. As examples of hydrophilic polysaccharides which may be used in 3D-porous scaffolds one may cite alginate salts, glycosaminoglycans, such as hyaluronic acid, dextran, or chitin/chitosan-based scaffolds, anionic biopolymers, such as carboxymethylcellulose (CMC), carboxymethylpullulan (CMP), carboxymethyldextran (CMD), carrageenan, or xanthan. As examples of synthetic polymers, one may cite polystyrene, poly-lactic acid (PLLA), polyglycolic acid (PGA) or poly-dl-lactic-co-glycolic acid (PLGA). As examples of proteins, one may cite collagens, laminin, fibronectin, tenascin, elastin, proteoglycans, or cross-linked peptides.

In some embodiments, a 3D-porous scaffold may be comprised of alginate salts, glycosaminoglycans, chitin/chitosan, or anionic biopolymers. A 3D-porous scaffold may be comprised of polystyrene, poly-lactic acid (PLLA), polyglycolic acid (PGA) or poly-dl-lactic-co-glycolic acid (PLGA).

In some embodiments, 3D-porous scaffold may be comprised of alginate salts, hyaluronic acid, chitin/chitosan, carboxymethylcellulose (CMC), carboxymethylpullulan (CMP), carboxymethyldextran (CMD), carrageenan, or xanthan.

3D-porous scaffolds may be obtained with hydrophilic polysaccharides cross-linked in presence of proteins, such as, for example, cross-linked glycosaminoglycan in presence of collagen or cross-linked alginate in presence of gelatin.

In one embodiment, a 3D-porous scaffold may be a cross-linked hydrogel. A cross-linked hydrogel may be comprised of cross-linked glycosaminoglycan, such as cross-linked hyaluronic acid, or cross-linked anionic biopolymers, such as alginate, carboxymethylcellulose (CMC), carboxymethylpullulan (CMP), carboxymethyldextran (CMD), carrageenan, or xanthan, and of collagen, fibronectin or laminin.

The use of cross-linked anionic biopolymers or cross-linked glycosaminoglycan, such as cross-linked hyaluronic acid, in 3D-porous scaffold is particularly advantageous in that they allow biological interactions between the cells of the liver organoid and the scaffold. The physicochemical properties of the 3D-porous scaffold allow keeping the stem cells in the matrix. In particular, the resistance to degradation of the matrix, for example made of cross-linked hyaluronic acid and collagen, allows cell proliferation and differentiation within the matrix.

The liver organoids disclosed herein may be, for example, frozen and/or lyophilized without loss of functions.

In some embodiments, a 3D-porous scaffold may be a cross-linked hydrogel, such as a cross-linked hydrogel comprised of cross-linked glycosaminoglycan, such as cross-linked hyaluronic acid, and of collagen, fibronectin or laminin. A scaffold may be a cross-linked hydrogel comprised of cross-linked hyaluronic acid and of collagen.

In one embodiment, the hydrophilic polysaccharides, such as the glycosaminoglycans, for example the hyaluronic acids, may be functionalized. The functionalization may be made with peptides promoting adhesion of the cultured cells or with galactosamine. As peptides useful for functionalization (or grafting), one may mention the ARG-GLY-ASP peptide (RGD) or ARG-GLY-ASP-SER peptide (RGDS) or CYS-ARG-GLY-ASP-SER peptide (CRGDS) or ARG-GLY-ASP-VAL peptide (RGDV). In some embodiments, a peptide used to functionalize a hydrophilic polysaccharide may be a ARG-GLY-ASP-SER peptide (RGDS). In one embodiment, a three-dimensional porous scaffold may be comprised of cross-linked hyaluronic acid and of collagen, the hyaluronic acid being grafted with RGDS (Arg-Gly-Asp-Ser) peptides.

For example, the degree of grafting of a hydrophilic polysaccharide, such as a glycosaminoglycan, for example a hyaluronic acid, with peptides may range from about 0.5 mol % to about 25 mol %, preferably from about 7 to about 18 mol %.

The hydrophilic polysaccharides, such as the glycosaminoglycans, may be cross-linked. Agents and parameters for cross-linking glycosaminoglycans are known in the art. For example, the cross-linking agent may be adipic acid dihydrazide (ADH), sebacic acid dihydrazide, dodecanediohydrazide, isophthalic acid dihydrazide, succinic acid dihydrazide or a diamine compound having two terminal primary amino functions ($H_2NR—NH_2$ where R represents any grouping between the 2 terminal amine functions).

For cross-linked hydrogel comprised of cross-linked glycosaminoglycan, such as hyaluronic acid, and of collagen, the cross-linking of the glycosaminoglycan may be carried out in presence of collagen, so that the 3D-porous scaffold is made of cross-linked glycosaminoglycan, such as hyaluronic acid, and of collagens. Suitable collagens may be collagen of type I and/or IV.

3D-porous scaffolds to be used in the methods as disclosed herein have pores the size of which allows migration of the cells inside the 3D matrix. If pores are too small cells cannot migrate in towards the center of the matrix limiting the diffusion of nutrients and removal of waste products. Conversely, if pores are too large there is a decrease in specific surface area available limiting cell attachment. In one embodiment, a 3D-porous scaffold may have pores having an average pore size ranging from about 50 to about 500 μm, in particular from about 80 μm to about 400 μm, in particular from about 100 μm to about 350 μm, in particular from about 100 μm to about 300 μm, in particular from about 100 μm to about 200 μm. In some preferred embodiments, a scaffold may have pores having an average pore size from about 100 μm to about 200 μm, in particular of about 100 μm, 105 μm, 110 μm, 115 μm, 120 μm, 125 μm, 130 μm, 135 μm, 140 μm, 145 μm, 150 μm, 155 μm, 160 μm, 165 μm, 170 μm, 175 μm, 180 μm, 185 μm, 190 μm, 195 μm or 200 μm.

In some embodiments, a 3D-porous scaffold may have pores having an average pore size of about 100 μm, for example of 100 μm+/−20 μm. In some embodiments, a 3D-porous scaffold may have pores having an average pore size of about 150 μm, for example of 150 μm+/−20 μm. In some embodiments, a 3D-porous scaffold may have pores having an average pore size of about 200 μm, for example of 200 μm+/−20 μm. The average pore size may be measured by any known methods in the art. As example of suitable method, one may mention the scanning electronic microscopy (SEM) as described in Louis et al. (*Biotechnol. Bioeng.,* 2017, 114: 1813-1824).

In some embodiments, a 3D-porous scaffold may be comprised of, or may consist in, cross-linked hyaluronic acid and of collagen, the hyaluronic acid being grafted with RGDS (Arg-Gly-Asp-Ser) peptides and may have pores having an average size of about 100 μm or of about 200 μm, for example of 100 μm+/−20 μm.

In some embodiments, a 3D-porous scaffold may be comprised of, or may consist in, cross-linked hyaluronic acid and of collagen, the hyaluronic acid being grafted with RGDS (Arg-Gly-Asp-Ser) peptides and may have pores having an average size of about 100 μm or of about 200 μm, for example of 200 μm+/−20 μm.

In some embodiments, a 3D-porous scaffold to be used in the methods as disclosed herein may have an elasticity from about 0.05 kPa to about 0.5 kPa.

The elasticity of the 3D-porous scaffold may be measured on a Discovery HR-2 rheometer. For instance, the elasticity may be measured following the method of rheological measurements disclosed in Louis et al. *Biotechnol Bioeng.* 2017 August; 114(8):1813-1824. For instance, the elasticity of a scaffold may be measured on a Discovery HR-2 rheometer equipped with an 8 mm parallel plate geometry on a stage heated to 37° C. Scaffold were tested at a frequency of 1 Hz and a logarithmic sweep from 1 to 500 Pa with five points per decade. The shear storage modulus may be determined by averaging at least five points in the linear viscoelastic region (LVR). The shear modulus measurements are converted to an elastic modulus E (KPa) value using the following equation $E=3G$.

In some particular embodiments, a 3D-porous scaffold may have an elasticity of about 0.05 kPa, 0.06 kPa, 0.07 kPa, 0.08 kPa, 0.09 kPa, 0.1 kPa, 0.15 kPa, 0.2 kPa, 0.25 kPa, 0.3 kPa, 0.35 kPa, 0.4 kPa, 0.45 kPa or 0.5 kPa. In some particular embodiments, a 3D-porous scaffold may have an elasticity from about 0.07 kPa to about 0.3 kPa, in particular from about 0.08 kPa to about 0.2 kPa.

In some preferred embodiments, a 3D-porous scaffold may have an elasticity of about 0.1 kPa.

In some embodiments, a 3D-porous scaffold may have pores having an average pore size ranging from about 50 to about 500 μm and an elasticity from about 0.05 kPa to about 0.5 kPa.

In some embodiments, a 3D-porous scaffold may have pores having an average pore size of about 100 μm and an elasticity of about 0.1 kPa.

In some embodiments, a 3D-porous scaffold may be comprised of, or may consist in, cross-linked hyaluronic acid and of collagen, the hyaluronic acid being grafted with RGDS (Arg-Gly-Asp-Ser) peptides and may have an elasticity of about 0.1 kPa.

In some embodiments, a 3D-porous scaffold may be comprised of, or may consist in, cross-linked hyaluronic acid and of collagen, the hyaluronic acid being grafted with RGDS (Arg-Gly-Asp-Ser) peptides and may have pores having an average pore size of about 100 μm or 200 μm and an elasticity of about 0.1 kPa.

In one embodiment, 3D-porous scaffolds may be provided under a lyophilized or dry form and may be rehydrated before use with the cell culture media to be subsequently used with the cells to be cultured into liver organoids. The rehydration of a dried or lyophilized 3D-porous scaffold allows to convert the scaffold in a hydrogel to be used as a 3D cell matrix.

In one exemplary embodiment, a 3D-porous scaffold suitable for the methods as disclosed herein may be obtained as disclosed in WO 2016/166479 A1.

In another exemplary embodiment, a 3D-porous scaffold suitable for the methods as disclosed herein may be a scaffold as obtained according to example 2 of WO 2016/166479 A1 entitled "Hydrogel for 3D Cell Culture of Hepatocytes". Such 3D-porous scaffold is composed of hyaluronic acid grafted with the RGDS peptide and of hyaluronic acid grafted with galactosamine, and the grafted hyaluronic acids are co-cross-linked in presence collagen I and IV. Such 3D-porous scaffold is commercially available from HCS Pharma under the reference Biomimesys® Liver.

Isolated Stem Cells

The method for preparing a liver organoid according to the present disclosure comprises the use of isolated stem cells. A liver organoid as disclosed herein may be obtained from the differentiation of at least one isolated stem cell.

In some embodiments, an isolated stem cell may be a pluripotent stem cell, for example an embryonic stem cell or an induced pluripotent stem cell.

The method is demonstrated in the examples by using iPSCs to generate the liver organoids. The use of isolated stem cells expressing pluripotency genes, shows that the current method could be applied to other pluripotent stem cells that have the ability to form liver cell types, i.e., embryonic stem cells, endoderm progenitors, hepatic endoderm progenitors.

The cells and liver organoids according to the present disclosure may be non-human animals or human.

As used herein, the term "pluripotent" refers to cells with the ability to give rise to progeny that can undergo differentiation, under appropriate conditions, into all cell types derived from the three germ layers (endoderm, mesoderm, and ectoderm) with specific cell lineages characteristics. The term "pluripotent" includes normal embryonic stem cells (ESCs), or very small embryonic-like stem cells (VSELs) or engineered induced pluripotent stem cells (iPSCs), reprogrammed from all sources and cell origins of adult somatic cells (ASCs). Pluripotent stem cells contribute to tissues of a prenatal, postnatal, or adult organism. Standard art-accepted tests may be used to establish the pluripotency of a cell population such as the ability to form a teratoma in 8-12 weeks old SCID mice. Human pluripotent stem cells express at least some (at least three, more generally at least four or five), and optionally all, of the markers from the following non-limiting list: SSEA-3, SSEA-4, TRA-1-60, TRA-1-81, TRA-2-49/6E, Alkaline phosphatase (ALP), Sox2, E-cadherin, UTF-I, Oct4, Lin28, Rex1, Nanog, TERC, TERT.

In certain embodiments, an isolated stem cell may be an embryonic stem cell. In certain other embodiments, an isolated stem cell may be a human embryonic stem cell. The hESCs may be isolated from a pre-blastocyst stage embryo. In some embodiments, the hESCs are not from an embryo. In another embodiment, the hES cells may be prepared by dedifferentiation of at least partially differentiated cells (e.g., multipotent cells) and are totipotent in practice. Methods of preparing hESC are well known in the art and taught, for example, in U.S. Pat. Nos. 5,843,780, 6,200,806, 7,029,913, 5,453,357, 5,690,926, 6,642,048, 6,800,480, 5,166,065, 6,090,622, 6,562,619, 6,921,632, and 5,914,268, U.S. Published Application No. 2005/0176707, International Application No. WO2001085917. In the context of the present disclosure, the human embryonic stem cells (hESC) are generated without embryo destruction according to the technology as described in Chung et al (*Cell Stem Cell.* 2008 Feb. 7; 2(2):113-7). Various animal (including human) ESC lines, such as, for example, NIH approved cell line WAO9 human ESCs can be obtained commercially from WiCell Research Institute, Madison, Wis. Human ESC lines, such as Cecol-14, can be obtained commercially for example from Cecolfes, Bogota, Colombia. Of course, other embryonic stem cell lines may be used, if desired.

As used herein, the term "induced pluripotent stem cell" refers to a pluripotent stem cell artificially derived from a non-pluripotent cell by a reprogramming procedure, using methods known in the art as disclosed in WO 2012/060473, WO 2007/069666, U.S. Pat. Nos. 9,499,797, 9,637,732, 8,158,766, 8,129,187, 8,058,065, or U.S. Pat. No. 8,278,104. In short, somatic cells are reprogrammed to induced pluripotent stem cells (iPSCs) by ectopic expression of defined factors such as Oct4, Sox2, Klf4 and c-My, or Oct4, Sox2, Lin28 and Nanog. In a particular embodiment, the induced pluripotent stem cells are derived from mammal's adult tissues in particular rodents, pigs, cats, dogs, and non-human primates, and human. In a preferred embodiment, the induced pluripotent stem cells are derived from human adult cells, in particular urine cells.

iPSCs may be generated from somatic cells of various origins, such as fibroblast, blood cells, keratinocytes, or cells from urines, and by using various technologies, such as integrative lentivirus/retrovirus and non-integrative vectors, such as Sendai of virus, episomal vectors, synthetic mRNA, Adenovirus, rAAV, recombinant proteins, with or without small chemical compounds.

Small molecules can be used to enhance induction and quality of iPSCs by acting as epigenetic modifiers, i.e., modifying expression of some genes. As an illustration, one can cite BIX01294 (BIX, a G9a histone methyltransferase inhibitor), sodium butyrate (NaBut, a histone deacetylase HDAC inhibitor) or S-adenosylhomocysteine (SAH, a DNA demethylation agent), 5-azacytidine (5-AZA, a DNA methyltransferase inhibitor), valproic acid (VPA, another histone deacetylase inhibitors) also improves reprogramming and quality of normal iPSCs.

ESC and iPSC can be amplified iteratively during multiple and illimited passages allowing scalable stem cells resources. Pluripotency potential is actively maintained in permissive culture conditions, by preserving high level expression of pluripotency genes. These methods are known in the art.

In some embodiments, liver organoids as disclosed herein may be generated from isolated pluripotent stem cells. For instance, iPSCs may be derived from somatic cell selected from urine cells, skin cells, blood cells, keratinocytes, fibroblasts, neural stem cells, liver cells, amniotic cells, adipocyte cells, 3 cells or melanocytes. In particular, iPSCs may be derived from urine cells.

In one exemplary embodiment, isolated stem cells to be used in methods as disclosed herein may be induced pluripotent stem cells derived from urine cells. For instance, induced pluripotent stem cells may be reprogrammed from patient urine cells as described in Si-Tayeb et al. (*Disease Models & Mechanisms* (2016) 9, 81-90).

The cells used for obtaining iPSCs may be isolated and distinguished from other cell types using any one of a number of physical separation methods known in the art. Such physical methods may involve FACS and various immunoaffinity methods based on markers specifically expressed by the desired cells.

In one embodiment, cells of the invention can be isolated by FACS using an antibody, e.g., an antibody directed to one of these markers. This may be accomplished by a fluorescently labeled antibody or by a fluorescently labeled secondary antibody with binding specificity for the primary antibody. Examples of suitable fluorescent labels include FITC, Alexa Fluor® 488, GFP, CFSE, CFDA-SE, DyLight 488, PE, PerCP, PE-Alexa Fluor® 700, PE-Cy5 (TRI-COLOR (Registered trademark), PE-Cy5.5, PI, PE-Alexa Fluor (registered trademark) 750, and PE-Cy7 are included, but not limited thereto. This list is shown as an example only and is not intended to be limiting.

In another embodiment, cells for induction of iPSCs may be isolated by immunoaffinity purification, which is a separation method well known in the art. By way of example only, cells for induction of iPSCs may be isolated by immunoaffinity purification for c-kit. This method relies on the immobilization of antibodies on a purification column.

In some embodiments, a cell population may be purified by performing several rounds of immunoaffinity purification using one or more of the other identifiable markers to isolate isolated clones.

In embodiments, sequential purification steps with different physical separation methods may be carried out. For example, cells may be purified by an immunoaffinity purification step using an SSEA-1 affinity column after a FACS step using an anti-marker cell of interest antibody. Isolated cells may be then cultured and expanded for some periods in culture to improve cell phenotype uniformity in the cell population.

In some embodiments, urine cells for induction of iPSCs may be isolated according to the method disclosed in Zhang et al., (*J Urol.* 2008 November; 180(5):2226-33) or in Si-Tayeb et al., (*Dis Model Mech.* 2016 January; 9(1):81-90).

In some embodiments, liver organoids may also be generated from early endoderm progenitors. Such cells reflect early endoderm lineage development.

In some embodiments, liver organoids may also be generated from mesendoderm progenitors. Such cells reflect mesendoderm lineage development.

In some embodiments, the isolated stem cells, in particular pluripotent stem cells, may be genetically modified by genome editing tools such as the Clustered regularly interspaced short palindromic repeats (CRISPR)/Cas system. These pluripotent stem cells maintain their pluripotential capacity and liver organoids may be generated from these genetically modified pluripotent stem cells.

In some embodiments, the isolated stem cells may be induced pluripotent stem cells (iPSCs) obtained a from patient suffering from a genetic disease. The disease-specific human iPSCs maintains their pluripotential capacity to give rise to endoderm lineage tissues. LO can be generated from these disease-specific iPSCs.

In some embodiments, the method of the present disclosure may use urines cells or isolated liver fragments from patients for obtaining the iPSCs. This may be advantageous for use of the liver organoids as disclosed herein in regenerative medicine. The cells or liver fragments may be autologous or allogeneic. An "autologous" cell is a cell derived from the same individual into which the cell is reintroduced, for example, to allow tissue regeneration for cell therapy. Autologous cells in principle do not require matching with the patient to overcome the problem of immune rejection and/or to reduce the need for immunosuppressive interventions during transplantation. An "allogeneic" cell is a cell that differs from the individual into which the cell is introduced. Some degree of patient matching may be required to prevent rejection problems. Techniques for minimizing tissue rejection are known in the art.

Liver Organoids (LOs) and Manufacturing Methods

Liver Organoids (LOs)

According to the disclosure, isolated stem cells, as described above may be placed in conditions suitable for proliferating in a 3D-porous scaffold to obtain a liver organoid (LO). Thus, liver organoids obtainable by the methods as disclosed herein are a further aspect of the disclosure. The functionality of the obtained LO may be characterized by the observation of the presence of liver markers as defined herein and/or by the metabolism of the organoid. A liver organoid as disclosed herein is an isolated liver organoid.

The present disclosure provides a liver organoid obtained by the method described herein. In particular, a liver organoid in a three-dimensional porous scaffold, more particularly a liver organoid in a cross-linked hyaluronic acid and of collagen.

As used herein, the term "organoid" refers to a range of 3D cell culture which resemble the modelled organ to varying extents. An organoid defines an in vitro 3D cellular cluster derived from tissue-resident stem/progenitor cells, embryonic stem cells (ESCs) or induced pluripotent stem cells (iPSCs) capable of self-renewal and self-organization that recapitulates the functionality of the tissue of origin.

The liver organoid described herein thereby fulfills the criteria of an organoid which mimics the in vivo organ. A liver organoid described herein contains at least four major cells types of the liver: the hepatocytes, the cholangiocytes, the stellate cells and the sinusoidal endothelial cells. A liver organoid described herein also included a structured cellular organization.

The organoid disclosed herein may comprise at least $1\times10^3$ cells, at least $1\times10^4$ cells, at least $1\times10^5$ cells, at least $1\times10^6$ cells, at least $1\times10^7$ cells. In some embodiments, each organoid may comprise about $1\times10^3$ cells to $5\times10^3$ cells. Generally, 10-20 organoids may be grown together in one well of a 24 well plate.

In one exemplary embodiment, a liver organoid as disclosed here expresses at least one of proteins chosen among Zonulas-Occludens 1 (ZO-1), E-cadherin, and OATP1B1.

Liver organoids disclosed herein may exhibit multiple liver specific functions including the liver specific metabolic activities (CYPs), accumulation of lipids, internalization of LDL, and secretion of testosterone. Liver organoids may exhibit hepatocyte genes expression such as albumin, Apo B, Apo (a), PCSK9 and CYP3A4.

In some embodiments, liver organoids disclosed herein may secrete Apolipoprotein (a). Apolipoprotein (a) is a liver protein involved in the transport of lipids (cholesterol, triglycerides, phospholipids) in the blood. Depending on the iPS cell line used during the differentiation process, liver organoids may secrete Apolipoprotein (a) which is one of the constituents of the lipoprotein Lp(a). This was the first report of a human in vitro model secreting Apo (a). Apo (a) was only found secreted in vitro in human PHH cells (Villard et al., *JACC Basic Transl Sci.* 2016 October; 1(6):419-427).

Illustrative examples of liver organoids according with the present disclosure are shown in the accompanying examples. As shown in Example 3, a liver organoid disclosed here is closest to the primary human hepatocyte than the hepatic liver cells obtained with a 2D cell culture method. For example, the liver organoids present a stronger activity of CYP enzymes (3A4 and 1A2) compared to hepatic liver cells, even if the liver organoids remained below slightly primary human hepatocyte with respect to CYPs 1A2, 2C9 and 2B6 activities. Advantageously, contrary to hepatic liver cells and primary human hepatocyte, the liver organoids present a stability after 3 days. Further, LO of the present disclosure secretes Apo (a) whereas HLC from the same individual do not secrete Apo(a) after 24 h secretion.

In some embodiments, the liver organoids disclosed here may present mature hepatocyte functions, featured by expression of different biomarkers including albumin, B-1 integrin, CK-8, CK-18, transthyretin (TTR), Glucose 6P, Met, glutamine synthase (Glul), transferrin, Fahd1, Fahd2a, K7, K19, and cytochrome P450 isoform CYP3A4, CYP2A2, CYP2C9, CYP2D6 and CYP2B6 expression or positive staining.

Liver organoids disclosed here comprise hepatocytes and cholangiocytes. Hepatocytes of LO disclosed herein may express at least one of the following hepatocytes biomarkers: albumin, transthyretrin, B-1 integrin, and glutamine synthetase, and/or CYP3A11, FAH, tbx3, TAT, or Gck. Cholangiocytes of the LO may expression at least one of the following cholangiocytes biomarkers: CFTR, SOX 9, keratin 7 or 19. Methods to detect and measure those biomarkers belong to the state of art. Suitable methods may be RT-PCR or immunohistochemistry methods. Expression of these biomarkers may be assessed as indicated in the Examples. These biomarkers may be expressed for at least two weeks, three weeks, or one month after obtaining the LOs.

Liver organoids disclosed herein further comprise stellate cells and sinusoidal endothelial cells. Biomarkers of stellate cells include at least one of LHX and desmine. Biomarkers of sinusoidal endothelial cells include at least one of CD31 and LYVE1.

In an exemplary embodiment, a liver organoid as described here, and obtained according to a method disclosed herein, may comprise at least hepatocytes, cholangiocytes, stellate cells, and sinusoidal endothelial cells.

In an exemplary embodiment, a liver organoid in a three-dimensional porous scaffold as described here may comprise at least hepatocytes, cholangiocytes, stellate cells, and sinusoidal endothelial cells. In one exemplary embodiment, the three-dimensional porous scaffold may be comprised of cross-linked hyaluronic acid and of collagen. In some examples, the three-dimensional porous scaffold may comprise cross-linked hyaluronic acid grafted with RGDS (Arg-Gly-Asp-Ser) peptides.

A liver organoid may comprise:

hepatocytes expressing albumin; and/or stellate cells expressing LHX2 and/or desmine; and/or cholangiocytes expressing CFTR and/or SOX9; and/or sinusoidal endothelial cells expressing CD31 and/or LYVE1.

In certain embodiments, liver organoids may further comprise Kupffer cells and innervation.

In some embodiments, the liver organoid may express at least one of the genes selected from CYP3A4, CYP1A2, CYP2C9, CYP2D6, CYP2B6, LIPC, UGT2B7, and/or PLG.

In one exemplary embodiment, LOs disclosed herein present a basal and/or an induced expression of at least one of the following CYPs: CYP3A4, CYP1A2, CYP2C9, CYP2D6 and/or CYP2B6.

LOs Manufacturing Methods

The present disclosure provides methods for preparing a liver organoid.

Methods of preparing LOs comprises seeding and culturing isolated stem cell in a three-dimensional porous scaffold to obtain a definitive endoderm cell. In some cases, the isolated stem cells may be early endoderm cells, mesendoderm cells, progenitor cells, pluripotent stem cells, induced pluripotent stem cells, or embryonic stem cells.

Therefore, a method disclosed here successfully produces a liver organoid in a three-dimensional porous scaffold that is metabolically and structurally similar to a liver, in particular a human liver.

The method for preparing a liver organoid described herein may use isolated stem cells, a set of cell-culture media for mammal cells suitable for growing and differentiating the isolated stem cells into a liver organoid, a three-dimensional porous scaffold and an alternate sequence of normoxic and hypoxic conditions.

The methods may comprise seeding and culturing isolated stem cells in a three-dimensional porous scaffold and submitting the isolated stem cell seeded in the scaffold to an alternate sequence of normoxic and hypoxic conditions.

Hypoxic conditions define a set of conditions where the amount of oxygen in the atmosphere contacting the cell culture media into which are cultured the cells is below the level required to ensure a normal level of oxygenation of the cells. As example of hypoxic conditions in cell culture one may cite conditions where the atmosphere may contain about 5% $CO_2$ and from about 2% to about 10% of $O_2$, for example from about 3% to about 5% of $O_2$, and for example of about 4% of $O_2$.

Normoxic conditions define a set of conditions where the amount of oxygen in the atmosphere contacting the cell culture media into which are cultured the cells is such that it allows to ensure a normal level of oxygenation of the cells. As example of normoxic conditions in cell culture one may cite conditions where the atmosphere may contain about 5% $CO_2$ and from about 15% to about 25% of $O_2$, for example from about 18% to about 22% of $O_2$, and for example of about 20% of $O_2$.

Whatever the hypoxic/normoxic conditions, the remaining gases in the atmosphere contacting the cell culture medium may the gases usually present in the earth atmosphere, such as $N_2$, Ar, etc. Those gases are usually in similar amounts than the ones present in earth atmosphere.

For instance, a means useable to switch from a condition of hypoxia to normoxia and conversely may be to switch the culture cells from an incubator to another.

The methods disclosed herein may comprise at least the steps of: (a) differentiating stem cells in definitive endoderm cells, (b) differentiating the definitive endoderm cells in hepatic endoderm cells, (c) differentiating the hepatic endoderm cells in hepatic progenitor cells and differentiating the hepatic progenitor cells in a liver organoid.

In some embodiments, the step of differentiating stem cells in definitive endoderm cells may further comprise a step of differentiating the stem cells in mesendoderm cells and differentiating the mesendoderm cells in definitive endoderm cells.

In some embodiments, the step of differentiating stem cells in definitive mesendoderm cells may further comprise a step of differentiating the stem cells in early endoderm cells, and differentiating the early endoderm cells in mesendoderm cells.

In one embodiment, a method for preparing a liver organoid may comprise the use of at least:

- i) a three-dimensional porous scaffold seeded with isolated stem cells,
- ii) a set of cell-culture media for mammal cells suitable for growing and differentiating the isolated stem cells into a liver organoid, the method may comprise at least a step of:

- a) contacting the seeded stem cells with a first set of cell culture media, under normoxic condition, to differentiate the stem cells in definitive endoderm cells;
- b) contacting the definitive endoderm cells obtained at step a) with a second set of cell culture media, under hypoxic condition, to differentiate the definitive endoderm cells in hepatic endoderm cells;
- c) contacting the hepatic endoderm cells obtained at step b) with a third set of cell culture media, under hypoxic condition, to differentiate the hepatic endoderm cells in hepatic progenitor cells; and
- d) contacting the hepatic progenitor cells obtained at step c) with a fourth set of cell culture media, under normoxic condition, to differentiate the hepatic progenitor cells in a liver organoid.

In further embodiments, a method disclosed herein may comprise:

- a) within the step of differentiating the seeded stem cells in definitive endoderm cells:
  - a1) a first phase of contacting the cells with a first cell-culture medium supplemented with a SMAD2/3 pathway activator, a fibroblast growth factor, and a bone morphogenetic protein, and
  - a2) a second phase of contacting the cells with a second cell-culture medium supplemented with a SMAD2/3 pathway activator, thereby obtaining the definitive endoderm cells;
- b) within the step of differentiating the definitive endoderm cells obtained at step a) in hepatic endoderm cells, contacting the cells with a third cell-culture medium supplemented with a fibroblast growth factor, a vascular endothelial growth factor, and a bone morphogenetic protein, thereby obtaining the hepatic endoderm cells;
- c) within the step of differentiating the hepatic endoderm cells obtained at step b) in hepatic progenitor cells:
  - c1) a first phase of contacting the cells with a fourth cell-culture medium supplemented with a hepatocyte growth factor, and an inhibitor of the TGF-β/Activin/NODAL pathway,
  - c2) a second phase of contacting the cells with a fifth cell-culture medium supplemented with a hepatocyte growth factor, and
  - c3) a third phase of contacting the cells with a sixth cell-culture medium supplemented with a hepatocyte growth factor and an interleukin (IL)-6 cytokine family activator, thereby obtaining the hepatic progenitor cells; and
- d) within the step of differentiating the hepatic progenitor cells obtained at step c) in the liver organoid:
  - d1) a first phase of contacting the cells with a seventh cell-culture medium, said cell-culture medium being a hepatocyte-culture medium supplemented with a hepatocyte growth factor, an interleukin (IL)-6 cytokine family activator, and a steroid,
  - d2) a second phase of contacting the cells with an eighth cell-culture medium, said cell-culture medium being a hepatocyte-culture medium supplemented with an interleukin (IL)-6 cytokine family activator, and a steroid, and d3) a third phase of contacting the cells with a ninth cell-culture medium, said cell-culture medium being a hepatocyte-culture medium, and thereby obtaining the liver organoid in the three-dimensional porous cell culture scaffold.

In some embodiments, the methods may optionally comprise as first step before step a). Such a step may comprise contacting the stem cells seeded in the scaffold in a tenth cell-culture medium supplemented with a ROCK family pathway inhibitor, said step being under hypoxic condition.

A move from one step of the methods to another, or from one phase to another, may be carried out by replacing a cell culture medium with a subsequent one. Replacement of cell culture medium may be carried by any known techniques in the art. For example, a cell culture medium to be replaced may be aspirated, while the 3D-porous scaffold bearing the cells remains in place, and the new cell culture medium is added to the vessel, e.g., plates, 24- or 96-wells plates, etc., containing the 3D-porous scaffolds.

Further to a change of cell culture media, the cells cultured in the porous scaffold may also be changed from oxygenation conditions, e.g., hypoxic to normoxic or reciprocally, by change of incubator.

Seeding and Growing Isolated Stem Cells

The stem cells are seeded in a 3D-porous scaffold.

Before being seeded with the stem cells, the 3D-porous scaffold may be contacted with the cell culture medium which will be subsequently used for the cell culture.

Further to the seeding, the cells may be contacted with a cell-culture medium supplemented with a ROCK family pathway inhibitor. Such a culture step may be carried under hypoxic condition.

This culture step is optional and may or not be carried out.

In one exemplary, methods disclosed herein comprise this culture step.

The set of culture media to be used in this step may be as above disclosed.

ROCK family pathway inhibitor suitable for this step may be Y27632, HA1077, or H1152, in particular Y27632.

This step may last for a period of time ranging from at least about 2 day to about 5 days and may last about 3 days.

This step is carried out under hypoxic conditions, for example 4% $O_2$ and 5% $CO_2$.

Differentiating Stem Cells in Definitive Endoderm Cells

The methods disclosed here may comprise a step of differentiating the seeded stem cells in definitive endoderm cells. This step may be carried under normoxic conditions. The cell culture media used for this step may be supplemented with a plurality of additives, such as at least a SMAD2/3 pathway activator, a fibroblast growth factor, and/or a bone morphogenetic protein. Such additives provide culture conditions suitable for differentiation of isolated stem cells to endoderm cells.

The set of culture media to be used in this step may be as above disclosed.

This step comprises two phases, a first and a second phase, each phase being defined by a cell culture medium, each cell culture medium comprising a specific set of additives.

The passage from the previous step to the present step is carried by the replacement of the cell culture medium of the previous step with the cell culture medium of the first phase of the present step.

Within the step, the passage from the first phase to the second phase is carried by the replacement of the cell culture medium of the first phase with the cell culture medium of the second phase.

In some embodiments, the step of differentiating stem cells in definitive endoderm cells under normoxic conditions may comprise a first phase of contacting the cells with a first cell-culture medium supplemented with a SMAD2/3 pathway activator, a fibroblast growth factor, and a bone morphogenetic protein, thereby obtaining mesendoderm cells. The cell-culture medium may be supplemented with Activin A, Fibroblast growth factor 2, and Bone morphogenetic protein 4.

In some embodiments, the step of differentiating the mesendoderm cells in definitive endoderm cells under normoxic conditions may comprise a second phase of contacting the cells with a second cell-culture medium supplemented with a SMAD2/3 pathway activator. The cell-culture medium may be supplemented with Activin A.

The cell-culture medium of the first and/or second phases may be supplemented with B27 and insulin.

This step is carried out under normoxic conditions, for example 20% $O_2$ and 5% $CO_2$.

This step may last for a period of time ranging from at least about 2 days to about 8 days and may last about 5 days.

In one embodiment, the first phase of this step may last for a period of time ranging from at least about 1 day to about 3 days and may last about 2 days.

In one embodiment, the second phase of this step may last for a period of time ranging from at least about 2 days to about 5 days and may last about 3 days.

Differentiating Definitive Endoderm Cells in Hepatic Endoderm Cells

The methods disclosed here may comprise a step of differentiating the definitive endoderm cells in hepatic endoderm cells. This step may be carried under hypoxic conditions, for example 4% $O_2$ and 5% $CO_2$. The cell culture media used for this step may be supplemented with a plurality of additives, such as at least a fibroblast growth factor, a vascular endothelial growth factor, and/or a bone morphogenetic protein. Such additives provide culture conditions suitable for differentiation of endoderm cells to hepatic endoderm cells.

The set of culture media to be used in this step may be as above disclosed.

This step may comprise a single phase.

The passage from the previous step to the present step is carried by the replacement of the cell culture medium of the previous step with the cell culture medium of the present step.

In some embodiments, the step of differentiating definitive endoderm cells in hepatic endoderm cells under hypoxic conditions may comprise contacting the cells with a third cell-culture medium supplemented with a fibroblast growth factor, a vascular endothelial growth factor, and a bone morphogenetic protein 4.

In one embodiment, the cell culture medium may be supplemented with fibroblast growth factor 2, vascular endothelial growth factor, and bone morphogenetic protein 4. The cell culture medium may further comprise B27 and insulin. The cell culture medium may be RPMI 1640.

This step may last for a period of time ranging from at least from about 2 days to about 10 days, from about 3 days to about 8 days, and may last about 5 days.

Differentiating Hepatic Endoderm Cells in Hepatic Progenitor Cells

The methods disclosed here may comprise a step of differentiating the hepatic endoderm cells in hepatic progenitor cells. The cell culture media used for this step supplemented with a plurality of additives, such as at least a hepatocyte growth factor, an inhibitor of the TGF-β/

Activin/NODAL pathway, and/or an interleukin (IL)-6 cytokine family activator. Such additives provide culture conditions suitable for differentiation of hepatic endoderm cells to hepatic progenitor cells.

This step may be carried under hypoxic conditions, for example 4% $O_2$ and 5% $CO_2$.

The set of culture media to be used in this step may be as above disclosed.

This step comprises three phases, a first, a second and a third phase, each phase being defined by a cell culture medium, each cell culture medium comprising a specific set of additives.

The passage from the previous step to the present step is carried by the replacement of the cell culture medium of the last phase of the previous step with the cell culture medium of the first phase of the present step.

Within the step, the passage from the first phase to the second phase is carried by the replacement of the cell culture medium of the first phase with the cell culture medium of the second phase.

In some embodiments, the step of differentiating the hepatic endoderm cells in hepatic progenitor cells under hypoxic conditions may comprise a first phase of contacting the cells with a fourth cell-culture medium supplemented with a hepatocyte growth factor, and an inhibitor of the TGF-β/Activin/NODAL pathway, a second phase of contacting the cells with a fifth cell-culture medium supplemented with a hepatocyte growth factor, and a third phase of contacting the cells with a sixth cell-culture medium supplemented with a hepatocyte growth factor and an interleukin (IL)-6 cytokine family activator.

In some other embodiments, the step of differentiating the hepatic endoderm cells in hepatic progenitor cells under hypoxic conditions may comprise a first phase of contacting the cells with a fourth cell-culture medium supplemented with Hepatocyte growth factor, and SB431542, a second phase of contacting the cells with a fifth cell-culture medium supplemented with Hepatocyte growth factor, and a third phase of contacting the cells with sixth a cell-culture medium supplemented with Hepatocyte growth factor and Oncostatin M.

In one embodiment, the cell culture medium of the three phases may be RPMI 1640. In some embodiments, the cell culture medium may be supplemented with B27, and for example with B27 and insulin.

This step may last for a period of time ranging from at least about 3 days to about 18 days, from about 6 days to about 15 days, and may last about 9 days.

In one embodiment, the first phase of this step may last for a period of time ranging from at least about 1 day to about 6 days, from about 2 days to about 5, and may last about 3 days.

In one embodiment, the second phase of this step may last for a period of time ranging from at least about 1 day to about 6 days, from about 2 days to about 5 days, and may last about 3 days.

In one embodiment, the third phase of this step may last for a period of time ranging from at least about 1 day to about 6 days, from about 2 days to about 5 days, and may last about 3 days.

Differentiating Hepatic Progenitor Cells in Liver Organoids

The methods disclosed here may comprise a step of differentiating the hepatic progenitor cells in a liver organoid. The cell culture media used for this step supplemented with a plurality of additives, such as at least a hepatocyte growth factor, an interleukin (IL)-6 cytokine family activator, and/or a steroid. Such additives provide culture conditions suitable for differentiation of hepatic progenitor cells to a liver organoid.

This step may be carried under normoxic conditions, for example 20% $O_2$ and 5% $CO_2$.

The set of culture media to be used in this step may be as above disclosed.

The culture medium to be used in this step may be a hepatocyte-culture medium.

This step comprises three phases, a first, a second and a third phase, each phase being defined by a cell culture medium, each cell culture medium comprising a specific set of additives.

The passage from the previous step to the present step is carried by the replacement of the cell culture medium of the last phase of the previous step with the cell culture medium of the first phase of the present step.

Within the step, the passage from the first phase to the second phase is carried by the replacement of the cell culture medium of the first phase with the cell culture medium of the second phase.

In some embodiments, the step of differentiating hepatic progenitor cells in a liver organoid under normoxic conditions may comprise a first phase of contacting the hepatic progenitor cells with a seventh cell culture medium supplemented with a hepatocyte growth factor, an interleukin (IL)-6 cytokine family activator, and a steroid, a second phase of contacting the early hepatocyte cells with a eighth cell culture medium supplemented with an interleukin (IL)-6 cytokine family activator, and a steroid, and a third phase of contacting the hepatocyte cells with a ninth cell culture medium without further additives.

In some other embodiments, the step of differentiating hepatic progenitor cells in a liver organoid under normoxic conditions may comprise a first phase of contacting the cells with a seventh cell culture medium supplemented with a hepatocyte growth factor, Oncostatin M, and dexamethasone, a second phase of contacting the cells with a eighth cell culture medium supplemented with Oncostatin M, and dexamethasone, and a third phase of contacting the cells with a ninth cell culture medium without further additives.

In one embodiment, the cell culture medium of the three phases may hepatocyte-culture medium, in particular without endothelial growth factor.

This step may last for a period of time ranging from at least about 5.5 day to about 17 days, from about 7 days to about 15 days, and may last about 9 days.

In one embodiment, the first phase of this step may last for a period of time ranging from at least about 3 days to about 9 days, from about 4 days to about 8, and may last about 6 days.

In one embodiment, the second phase of this step may last for a period of time ranging from at least about 2 days to about 5 days and may last about 3 days.

In one embodiment, the third phase of this step may last for a period of time ranging from at least about 12 hours to about 3 days, from about 1 day to about 2 days, and may last about 1 day.

The liver organoids obtained according to the disclosed methods may comprise at least hepatocytes, cholangiocytes, stellate cells, and sinusoidal endothelial cells.

In one embodiment, a method for preparing a liver organoid as disclosed herein may comprise at least:

i) a three-dimensional porous scaffold seeded with isolated stem cells, the three-dimensional porous scaffold being comprised of cross-linked hyaluronic acid grafted with RGDS (Arg-Gly-Asp-Ser) peptides and of collagen, ii) a set of cell-culture media for mammal cells suitable for growing and differentiating the isolated stem cells into a liver organoid, the method comprising at least a step of:

a) contacting the seeded stem cells with a first set of cell culture media, under normoxic condition, to differentiate the stem cells in definitive endoderm cells, said step comprising:

a1) a first phase lasting for about 2 days of contacting the stem cells with a first cell-culture medium, for example RPMI 1640, supplemented with B27 comprising insulin, and comprising a SMAD2/3 pathway activator, a fibroblast growth factor, and a bone morphogenetic protein, thereby differentiating the stem cells in mesendoderm cells; and a2) a second phase lasting for about 3 days of contacting the mesendoderm cells with a second cell-culture medium, for example RPMI 1640, supplemented with B27 comprising insulin, and comprising a SMAD2/3 pathway activator, thereby differentiating the mesendoderm cells in definitive endoderm cells, b) contacting the definitive endoderm cells obtained at step a) with a second set of cell culture media, under hypoxic condition, to differentiate the definitive endoderm cells in hepatic endoderm cells, said step comprising a single phase lasting about 5 days of contacting the definitive endoderm cells with a third cell-culture medium, for example RPMI 1640, supplemented with B27 comprising insulin, and comprising a fibroblast growth factor, a vascular endothelial growth factor, and a bone morphogenetic protein, thereby differentiating the definitive endoderm cells in hepatic endoderm cells, and c) contacting the hepatic endoderm cells obtained at step b) with a third set of cell culture media, under hypoxic condition, to differentiate the hepatic endoderm cells in hepatic progenitor cells, said step comprising:

c1) a first phase lasting about 3 days of contacting the cells with a fourth cell-culture medium, for example RPMI 1640, supplemented with B27 comprising insulin, and comprising a hepatocyte growth factor, and an inhibitor of the TGF-β/Activin/NODAL pathway, c2) a second phase lasting about 3 days of contacting the cells with a fifth cell-culture medium, for example RPMI 1640, supplemented with B27 comprising insulin, and comprising a hepatocyte growth factor, and c3) a third phase lasting about 3 days of contacting the cells with a sixth cell-culture medium, for example RPMI 1640, supplemented with B27 comprising insulin, and comprising a hepatocyte growth factor, and an interleukin (IL)-6 cytokine family activator, thereby differentiating the hepatic endoderm cells in hepatic progenitor cells, and d) contacting the hepatic progenitor cells obtained at step c) with a further set of cell culture media, under normoxic condition, to differentiate the hepatic progenitor cells in a liver organoid, said step comprising:

d1) a first phase lasting about 6 days of contacting the hepatic progenitor cells with a seventh cell culture medium, for example a hepatocyte culture medium, comprising a hepatocyte growth factor, an interleukin (IL)-6 cytokine family activator, and a steroid, d2) a second phase lasting about 3 days of contacting the early hepatocyte cells with an eighth cell culture medium, for example a hepatocyte culture medium, comprising an interleukin (IL)-6 cytokine family activator, and a steroid, and d3) a third phase lasting about 1 day of contacting the hepatocyte cells with a ninth cell culture medium, for example a hepatocyte culture medium, thereby obtaining a liver organoid.

Methods disclosed herein may further comprise, before the step a) as above indicated, a step of contacting, for about 3 days, under hypoxic condition, the stem cells with a cell-culture medium, for example StemMACS iPS-Brew, comprising a ROCK family pathway inhibitor.

In one embodiment, a method for preparing a liver organoid as disclosed herein may comprise at least:

i) a three-dimensional porous scaffold seeded with isolated stem cells, the three-dimensional porous scaffold being comprised of cross-linked hyaluronic acid grafted with RGDS (Arg-Gly-Asp-Ser) peptides and of collagen, ii) a set of cell-culture media for mammal cells suitable for growing and differentiating the isolated stem cells into a liver organoid, the method comprising at least a step of:

a) contacting the seeded stem cells with a first set of cell culture media, under normoxic condition, to differentiate the stem cells in definitive endoderm cells, said step comprising:

a1) a first phase lasting for about 2 days of contacting the stem cells with a first cell-culture medium, for example RPMI 1640, supplemented with B27 comprising insulin, and comprising Activin A, Fibroblast Growth Factor 2, and Bone Morphogenetic Protein 4, thereby differentiating the stem cells in mesendoderm cells; and a2) a second phase lasting for about 3 days of contacting the mesendoderm cells with a second cell-culture medium, for example RPMI 1640, supplemented with B27 comprising insulin, and comprising Activin A, thereby differentiating the mesendoderm cells in definitive endoderm cells, b) contacting the definitive endoderm cells obtained at step a) with a second set of cell culture media, under hypoxic condition, to differentiate the definitive endoderm cells in hepatic endoderm cells, said step comprising a single phase lasting about 5 days of contacting the definitive endoderm cells with a third cell-culture medium, for example RPMI 1640, supplemented with B27 comprising insulin, and comprising Fibroblast Growth Factor 2, a Vascular Endothelial Growth Factor, Bone Morphogenetic Protein 4, thereby differentiating the definitive endoderm cells in hepatic endoderm cells, and c) contacting the hepatic endoderm cells obtained at step b) with a third set of cell culture media, under hypoxic condition, to differentiate the hepatic endoderm cells in hepatic progenitor cells, said step comprising:

c1) a first phase lasting about 3 days of contacting the cells with a fourth cell-culture medium, for example RPMI 1640, supplemented with B27 comprising insulin, and comprising hepatocyte growth factor and SB431542, c2) a second phase lasting about 3 days of contacting the cells with a fifth cell-culture medium, for example RPMI 1640, supplemented with B27 comprising insulin, and comprising a hepatocyte growth factor, and c3) a third phase lasting about 3 days of contacting the cells with a sixth cell-culture medium, for example RPMI 1640, supplemented with B27 comprising insulin, and comprising a hepatocyte growth factor, and Oncostatin M, thereby differentiating the hepatic endoderm cells in hepatic progenitor cells, and d) contacting the hepatic progenitor cells obtained at step c) with a further set of cell culture media, under normoxic condition, to differentiate the hepatic progenitor cells in a liver organoid, said step comprising:

d1) a first phase lasting about 6 days of contacting the hepatic progenitor cells with a seventh cell culture medium, for example a hepatocyte culture medium, comprising a hepatocyte growth factor, Oncostatin M, and dexamethasone, d2) a second phase lasting about 3 days of contacting the early hepatocyte cells with an eighth cell culture medium, for example a hepatocyte culture medium, comprising Oncostatin M, and dexamethasone, and d3) a third phase lasting about 1 day of contacting the hepatocyte cells with a ninth cell culture medium, for example a hepatocyte culture medium, thereby obtaining a liver organoid Methods disclosed herein may further comprise, before the step a) as above indicated, a step of contacting, for about 3 days, under hypoxic condition, the stem cells with a cell-culture medium, for example StemMACS iPS-Brew, comprising a ROCK family pathway inhibitor, such as Y27632.

Uses of the Liver Organoids

The present disclosure also provides uses of and methods implementing liver organoids as disclosed herein or prepared by the methods described herein in drug discovery screens, drug developments, toxicity assays, serious adverse event (SAE) detection, in regenerative medicine, or in the treatment of hepatic disorders.

In some embodiments, it is disclosed the use of liver organoids as described herein or prepared by the methods described herein in toxicity assays, for example for toxicity determination of substances, such as food supplements, environmental pollutants, or drugs, on living systems, or for serious adverse event (SAE) detection.

In one embodiment, a method for evaluating toxicity of a substance, e.g., a drug, an environmental pollutant or a food supplement may comprise a step of contacting a liver organoid as disclosed herein with the substance, and steps of measuring at least one biomarker of the liver organoid before and after contacting the liver organoid with the substance and comparing the measured biomarker. The comparison of the measures of the biomarker obtained before and after contacting the liver organoid with the substance may be indicative of a liver toxicity of the substance.

In some embodiments, a method for evaluating toxicity of a substance, e.g., a drug, an environmental pollutant or a food supplement may comprise a step of preparing a liver organoid according to the method of the present disclosure, a step of contacting the obtained liver organoid with the substance, and steps of measuring at least one biomarker of the liver organoid before and after contacting the liver organoid with the substance and comparing the measured biomarker. The comparison of the measures of the biomarker obtained before and after contacting the liver organoid with the substance may be indicative of a liver toxicity of the substance.

In one embodiment, a method of screening for a serious adverse event (SAE) is disclosed. The SAE may be liver failure and/or drug induced liver injury (DILI). The method may include the step of contacting a drug of interest, of which toxicity is of interest, with a liver organoid as described herein, and steps of measuring at least one biomarker of the liver organoid before and after contacting the liver organoid with the drug. In one aspect, the method may comprise the step of measuring intake and/or efflux of fluorescein diacetate (FD), wherein impaired efflux indicates that said drug is likely to induce a serious adverse event. The toxicity of a drug of interest may be determined by measurement of a biomarker selected from mitochondria membrane potential, measurement of reactive oxygen species (ROS), swelling of liver mitochondria, and combinations thereof, wherein injury to said mitochondria indicates that said drug is likely to induce a serious adverse event. In one embodiment, the method may comprise a step of assaying organoid viability, wherein impaired or decreased organoid viability indicates that said a drug of interest is likely to induce a serious adverse event. In another embodiment, measure of cytochrome P450 enzymes induction in hepatocytes may be a biomarker of the efficacy and toxicity of drugs. In particular, induction of P450 is an important mechanism of troublesome drug-drug interactions, and it is also an important factor that limits drug efficacy and governs drug toxicity.

In some embodiments, a method of screening for a serious adverse event (SAE) may include a step of preparing a liver organoid according to the method of the present disclosure, a step of contacting a drug of interest, of which toxicity is of interest, with the obtained liver organoid, and steps of measuring at least one biomarker of the liver organoid before and after contacting the liver organoid with the drug.

A toxicity assay may be an in vitro assay using liver organoid-derived cells or liver organoid or portions thereof described herein. The toxic results obtained with liver organoids are expected to be very similar to those obtained in patients. Cell-based toxicity tests may be used to confirm organ-specific cytotoxicity. Examples of compounds to be tested include cancer chemotherapeutic agents, pharmaceutical drugs, environmental chemicals, nutraceuticals, and potentially toxic substances.

In some embodiments, liver organoids disclosed herein or prepared by the methods described herein may be used for studies of hepatogenesis, liver cell lines, differentiation pathways; gene expression including recombinant gene expression; mechanisms involved in liver damage and repair, mechanisms involved in liver inflammation and infections; pathogenesis mechanisms; and liver cell transformation mechanisms and liver cancer pathogenesis.

In one embodiment, methods of uses disclosed herein may be for drug discovery screens or drug developments of a therapeutic agent suitable for an individual.

The method for drug development may include the steps of contacting a liver organoid, as described herein, with a drug candidate, measuring of at least one biomarker from the liver organoid before, and comparing the measured biomarker with a reference. A reference may be a measure of the biomarker obtained before contacting the liver organoid with the drug candidate. A comparison of the measured biomarker in presence and in absence (e.g., reference) of the drug candidate may be indicative of or informative about i) an absorption, a distribution, a metabolization, and/or an excretion of the tested drug candidate in a liver; ii) a potential benefit of the tested drug candidate; iii) a mechanisms of action of the tested drug candidate, iv) a dosage effective to achieve an effect of the tested drug candidate; v) a potential level of toxicity of the tested drug candidate; vi) an interaction of the tested drug candidate with other drug compounds and treatments; and/or vii) an effectiveness of the tested drug candidate compared with similar drug compounds on a given disease.

In some embodiments, the method for drug development may include the steps of preparing a liver organoid according to the method of the present disclosure, the step of contacting the obtained liver organoid with a drug candidate, measuring of at least one biomarker from the liver organoid before, and comparing the measured biomarker with a reference.

The method for drug discovery screens may include the steps of contacting a liver organoid, as described herein, with a library of potential drug candidates, identifying of at least one drug candidate able to bind with a biological target involved in the outcome of a given disease, and selecting the at least one drug candidate for a drug development.

In some embodiments, the method for drug discovery screens may include the steps of preparing a liver organoid according to the method of the present disclosure, contacting the obtained liver organoid with a library of potential drug candidates, identifying of at least one drug candidate able to bind with a biological target involved in the outcome of a given disease, and selecting the at least one drug candidate for a drug development.

In some embodiments, liver organoids disclosed herein may be used to culture pathogens and thus can be used as ex vivo infection models. Examples of pathogens that may be cultured using a liver organoid as described herein include viruses, bacteria, prions or fungi that cause disease in a host. Thus, a liver organoid as described herein can be used as a disease model that represents an infected state.

Furthermore, a liver organoid as described herein can be used for culturing of a pathogen, such as a virus, bacteria prion or fungi, which lacks a suitable tissue culture or animal model. The method of culturing may include the step of contacting a liver organoid, as described herein, with a pathogen-containing sample under suitable conditions for the growth of the pathogen.

In some embodiments, the method of culturing of a pathogen may include the step of preparing a liver organoid according to the method of the present disclosure, and contacting the obtained liver organoid with a pathogen-containing sample under suitable conditions for the growth of the pathogen.

The present disclosure also relates to a liver organoid as described herein or prepared by the method described herein for use in a method of treatment of a hepatic disorder. In some embodiments, liver organoids disclosed or prepared by the methods described herein may be used in regenerative medicine.

In some embodiment, it is also disclosed a method of treatment of a hepatic disorder in a subject in need thereof comprising the steps of preparing a liver organoid according to the method of the present disclosure and administering the obtained liver organoid in order to treat the subject.

As used herein, the term "hepatic disorder" refers to a mammalian and preferably a human liver disease or condition associated with hepatocellular injury or a biliary tract disorder.

In some embodiments, hepatic disorders include many diseases and disorders wherein the liver functions improperly or ceases to function.

In some embodiments, a hepatic disorder is selected in the group comprising; chronic liver failure resulting from hereditary metabolic disease or chronic liver failure resulting from hepatocellular infection or others exogenous factors (diet, drug or alcohol).

Liver diseases include hepatocellular carcinoma, Alagille syndrome, alpha-1-antitrypsin deficiency, autoimmune hepatitis, biliary atresia, chronic hepatitis, liver cancer, cirrhosis, liver cyst, fatty liver, galactosemia, Gilbert syndrome, primary bile cirrhosis, hepatitis A, hepatitis B, hepatitis C, primary sclerosing cholangitis, Rye syndrome, sarcoidosis, tyrosinemia, type I glycogen storage disease, Wilson's disease, neonatal hepatitis, alcoholic or non-alcoholic steatohepatitis, porphyria and hemochromatosis.

In some embodiments, a hepatic disorder also refers to hereditary diseases involving dysfunctional hepatocytes. Such diseases may be early onset or late onset. Early-onset disease includes organ failure associated with a metabolite (e.g., α-1-antitrypsin deficiency), glycogenosis (e.g., GSDII, Pompe disease), tyrosinemia, mild DGUOK, CDA type I, Urea cycle defects (e.g., OTC deficiency), organic academia, and fatty acid oxidation disorders are included. Late-onset disease includes primary hyperoxaluria, familial hypercholesterolemia, Wilson's disease, hereditary amyloidosis, and polycystic liver disease. Partial or complete replacement with healthy hepatocytes generated from the liver organoids in a three-dimensional porous scaffold or generated by the method of the disclosure can be used to restore liver function or delay liver failure.

The liver organoids of the disclosure can be used to treat acute liver failure, e.g., acute liver failure as a result of liver poisoning that may result from the use of paracetamol, drugs, or alcohol. In some embodiments, the therapy to restore liver function comprises injecting a hepatocyte suspension from frozen easy-to-use allogeneic hepatocytes obtained from the liver organoid of the present disclosure. Being able to freeze the appropriate organoid means that it can be delivered immediately, so there is no need to wait for blood transfusion.

In some embodiments, liver organoids disclosed or prepared by the methods described herein may be used in regenerative medicine, such as in methods for liver epithelial repair after radiation and/or surgery, or for treatment of patients suffering from chronic or acute liver failure or disease.

The use of liver organoids in a three-dimensional porous scaffold as described herein for treatment of hepatic disorders, regenerative medicine or transplantation purposes is advantageous over the use of primary human hepatocytes for a number of reasons. First, the culture method of the present invention provides unlimited cell expansion, and hence unlimited supply. In particular, it is shown that under appropriate culture conditions (for example, with suitable culture conditions using alternate sequence of normoxic and hypoxic conditions of the present disclosure), hepatocyte progenitor cells divide easily in vitro. Thus, hepatocyte progenitor cells can be extracted from liver organoids and passaged several times to provide a continuous, self-replicating source of transplantable hepatocytes and cholangiocytes developing cells. In contrast, primary human hepatocytes are obtained from donor livers which are only transplanted once. In addition, donor cells can only survive a few days and lose stem cell properties. This means that the graft must be made as soon as the donor appears. On the other hand, the organoid-derived cells divide several times and retain the phenotype for a long time. This means that the organoid-derived cells are ready for transplantation at any stage and can be used for transplantation. To this end, it may be possible to use organoid-derived cells as a temporary liver therapy that prolongs the life of patients enrolled on the liver transplant waiting list.

A further advantage of the liver organoids of the present disclosure may be that they can be frozen and later thawed without loss of function. This allows for cell banking, facilitates storage, and can be used quickly for rapid use. This may be useful, for example, in the preparation of "off-the-shelf" products that can be used to treat acute liver toxicity. Organoids can also grow from cells or tissue fragments taken as small biopsies from living donors, which minimizes the ethical opposition to therapy. The donor may be from the patient to be treated. This may reduce the side effects associated with transplantation of foreign cells and organs and may reduce the need for immunosuppressive drugs.

Thus, methods of treating human or animal patients by cell therapy are included within the scope of the present invention. The term "animal" as used herein refers to all mammals, preferably human patients. Such cell therapy involves the administration to the patient of cells or liver organoids as disclosed herein or made in accordance with the present disclosure by any suitable means. The term "administration" as used herein includes administration such as intravenous administration or injection, as well as transplantation, e.g., administration by surgery, grafting, of liver organoids as disclosed herein or obtained by the methods of the disclosure.

Therefore, in one embodiment it is described a method of treating an individual having a liver disorder, comprising at least a step of implanting a liver organoid prepared by the method according to the disclosure, or a liver organoid in a three-dimensional porous scaffold as described into said individual.

In one aspect, a method of treating an individual having liver damage is disclosed, wherein the method may comprise the step implanting a liver organoid as described herein or obtained according to the methods disclosed herein into an individual in need thereof. In another aspect, a method of treating an individual having liver damage is disclosed, wherein the method may comprise the steps of preparing a liver organoid according to the methods as disclosed herein and implanting a liver organoid obtained accordingly into an individual in need thereof. The liver damage may include, for example, metabolic liver disease, end stage liver disease, or a combination thereof.

In some embodiments, the uses and methods as described herein may also encompass a first step of preparing a liver organoid according to the methods of the present disclosure.

Kit-of-Parts

The present disclosure also provides a kit-of-parts for preparing a liver organoid. Such a kit may be suitable to implement the methods disclosed herein.

A kit-of-parts may comprise:

i) isolated stem cells, for example maintained in frozen or lyophilized conditions, ii) a three-dimensional porous scaffold comprised of cross-linked hyaluronic acid and of collagen, iii) a set of cell-culture media for mammal cells suitable for differentiating the stem cells into a liver organoid, iv) a set of additives comprising a SMAD2/3 pathway activator, a fibroblast growth factor, a bone morphogenetic protein, a vascular endothelial growth factor, a hepatocyte growth factor, an inhibitor of the TGF-β/Activin/NODAL pathway, an interleukin (IL)-6 cytokine family activator, a steroid, and optionally B27, v) a set of instructions for preparing said liver organoid according to a method as described herein.

The parts of the kit, such as isolated stem cells, a three-dimensional porous scaffold, and the set of cell-culture media are packaged in suitable containers allowing their conservation over time. Such containers are known in the art.

The additives may be packaged individually or in combination, depending of their use with different media of the set of cell culture media.

It is to be understood that the disclosure encompasses all variations, combinations, and permutations in which at least one limitation, element, clause, descriptive term, etc., from at least one of the listed claims is introduced into another claim dependent on the same base claim (or, as relevant, on any other claim) unless otherwise indicated or unless it would be evident to one of ordinary skill in the art that a contradiction or inconsistency would arise.

Where elements are presented as lists, e.g., in Markush group or similar format, it is to be understood that each subgroup of the elements is also disclosed, and any element(s) can be removed from the group. It should be understood that, in general, where the disclosure, or aspects of the disclosure, is/are referred to as comprising particular elements, features, etc., they also encompass embodiments consisting, or consisting essentially of, such elements, features, etc. For purposes of conciseness, those embodiments have not, in every case, been specifically set forth in so many words herein. It should also be understood that any embodiment or aspect of the disclosure can be explicitly excluded from the claims, regardless of whether the specific exclusion is recited in the specification.

The publications and other reference materials referenced herein for describing the background of the disclosure and providing additional detail regarding its practice are hereby incorporated by reference.

Without limiting the present disclosure, a number of embodiments of the present disclosure are described below for the purpose of illustration.

EXAMPLES

Example 1: Materials and Methods

Primary Human Hepatocyte (PHH) Cells Culture

The primary human hepatocyte (PHH) cell line was obtained from four different healthy donors. PHH cells culture was performed according to the LONZA protocol (described in Document #BR-CryoHep-1 07/20 www.bioscience.lonza.com © 2020 Lonza Walkersville, Inc) with cell seeding at 70,000 cells/well in collagen I-coated 96-well plates (Corning® BioCoat™ Collagen I 96 Clear Well Plate). One hour after seeding, the PHH cells were cultured by the Sandwich method using Matrigel (Corning® Matrigel® Matrix) according to the protocol described in Gijbels et al. (*Experimental Cholestasis Research,* 2019). PHH cells were used 3 days later (short duration) or 2 weeks later (long duration) for the experiments. PHH cell line was cultivated at 37° C. in a humidified atmosphere with 5% $CO_2$.

Human Induced Pluripotent Stem Cells (hiPSC) Culture

The human induced pluripotent stem cells (hiPSCs) were reprogrammed from patient urine cells (Ucells) and characterized as described in Si-Tayeb et al. (*Disease Models & Mechanisms* (2016) 9, 81-90). The protocol is as follows.

Urine Cell (Ucell) Collection and Culture

Urine samples were collected from healthy patient in a 250 ml bottle previously conditioned with 10% of RE/MC medium (see below) for storage (up to 24 h at 4° C.) and transported as previously described (Lang et al., 2013. *PLoS ONE* 8, e53980). RE/MC (1:1) medium was prepared as described by Zhou et al. (*Nat. Protoc.* 7, 2080-2089 (2012)) by mixing RE medium (Renal epithelial cell growth medium SingleQuot kit supplement and growth factors; Lonza) with MC (mesenchymal cell) medium prepared separately. MC medium is composed of DMEM/high glucose medium (Hyclone) supplemented with 10% (vol/vol) FBS (Hyclone), 1% (vol/vol) GlutaMAX (Life Technologies), 1% (vol/vol) NEAA (Life Technologies), 100 U/ml penicillin (Life Technologies), 100 μg/ml streptomycin (Life Technologies), 5 ng/ml bFGF2 (Miltenyi), 5 ng/ml PDGF-AB (Cell Guidance Systems) and 5 ng/ml EGF (Peprotech). Urine cells (Ucells) were isolated from urine samples and cultured according to the procedure described in Zhou et al. (2012) with slight modifications. Briefly, urine samples were centrifuged 5 min at 1200 g and the pellet was washed with pre-warmed DPBS (Gibco) containing 100 U/ml penicillin and 100 μg/ml streptomycin (Gibco). Pellets were resuspended in 2 ml RE/MC proliferation medium and cultured on 0.1% gelatin-coated six-well plates. Cells were incubated at 37° C. in normoxia (20% $O_2$, 5% $CO_2$) for 4-5 days without any change of medium nor moving. Ucells were further passaged using TrypLE Express (Gibco) and expanded in RE/MC medium with daily change of half of the media. Upon amplification, Ucells were characterized and frozen (Biobanker, Zenoaq). For Ucell characterization, expression of mesenchymal stem cells surface markers SSEA3, SSEA4 and TRA1-60 was measured using flow cytometry and their capacity to differentiate into osteocytic and chondrocytic tissue was evaluated as previously described (Bharadwaj et al., 2013. Stem Cells 31, 1840-1856).

Ucell Reprogramming

Then, Ucells were reprogrammed into UhiPSCs (namely hiPSCs) as follows. $3\times10^5$ to $5\times10^5$ of fresh or frozen Ucells were nucleofected using the basic epithelial cells Nucleofector Kit (Lonza) with episomal vectors coding for OCT4, SOX2, KLF4, MYC, LIN28, NANOG and SV40LT (Addgene Cat #20922, 20923, 20924, 20925 and 20927), and a non-episomal vector coding for miR302/367 (System Biosciences Cat #TDH101PA-GP). Nucleofected Ucells were cultured at 37° C. under hypoxia conditions (4% $O_2$, 5% $CO_2$) for 7 days with RE/MC medium then 14-21 days with TeSR-E7 medium (Stem Cell Technologies). UhiPSC clones were manually picked and transferred onto mitomycin-treated MEFs for further culture and amplification.

hiPSC Culture hiPSCs were cultured on mouse embryonic fibroblasts (MEF), in a hiPSC medium comprised of DMEM/F12 (Life Technologies—31330-038) supplemented with 20% Knock-out Serum Replacer (Life Technologies), 0.5% L-Glutamine (Life Technologies) with 0.14% β-mercaptoethanol (Sigma), 1% NEAA and 5 ng/ml fibroblast growth factor 2 (FGF2, Miltenyi), under conditions of hypoxia (4% $O_2$, 5% $CO_2$) at 37° C. Cells were passed manually once a week. Then, hiPSC colonies were selected and manually removed from the MEF and placed on Matrigel-coated plates (Corning® Matrigel® Matrix; 0.05 mg/ml) in StemMACS iPS-Brew medium (Miltenyi) without MEF. Passages were performed using non-enzymatic cell dissociation buffer (Stem Cell Technologies).

Two-Dimensions (2D) Hepatic Liver Cells (HLC) Differentiation from hiPSC hiPSCs were differentiated into hepatocyte cells (HLC) in two-dimensions gel as described in Si-Tayeb et al. (*Disease Models & Mechanisms* (2016) 9, 81-90). Hepatic differentiation was induced once hiPSCs have reached about 80-90% confluence.

Subsequently, hiPSCs were cultured for 2 days in normoxia (20% $O_2$, 5% $CO_2$) at 37° C. in RPMI 1640 medium (Life Technologies—21875091) supplemented with B27 (with insulin) (Life Technologies-17504044) containing Activin A 100 ng/ml (Miltenyi), FGF2 20 ng/ml (Miltenyi) and BMP4 10 ng/ml (Miltenyi). Then, culture medium was removed and replaced with a RPMI 1640 medium (Life Technologies—21875091) with Activin A 1 000 ng/ml to differentiate the cells into definitive mesendodermic cells and subsequently in definitive endodermic cells.

Definitive endodermic cells were then differentiated into hepatic progenitor cells further to a culture for 5 days in RPMI 1640 medium supplemented with BMP4 20 ng/ml and FGF2 10 ng/ml in hypoxia (4% $O_2$, 5% $CO_2$) at 37° C.

Subsequently, cells were cultured for 5 days in RPMI 1640 medium supplemented with HGF 20 ng/ml (Miltenyi) in hypoxia (4% $O_2$, 5% $CO_2$) at 37° C. to obtain immature hepatocytes.

Then, the cells were differentiated into mature hepatocytes (HCL) further to a culture step in a hepatocyte culture medium (HCM) (Lonza—CC-3198) supplemented with Oncostatin M 20 ng/ml (Miltenyi) for an additional 5-6 days in normoxia (20% $O_2$, 5% $CO_2$) at 37° C.

At the end of the protocol, HLC were used either 3 days later (short term) or 2 weeks later (long term).

3D-Porous Hydroscaffold

For differentiation of the hiPSCs into 3-dimensions (3D) LO, cells were culture in a 3D porous hydroscaffold. The hydroscaffold was prepared according to the procedure disclosed in WO 2016/166479 A1 to HCS Pharma. The 3D-porous scaffold was obtained by cross-linking of hyaluronic acid grafted with RGDS units and galactosamine with adipic acid dihydrazide in presence of type-I and type-IV collagens, two major types of collagens in the liver. Both collagens were introduced in physiological proportions (as disclosed in WO 2016/166479 A1) to better mimic the cellular microenvironment. After purification, the obtained hydrogel is poured into 96-well plates with a volume of 50 μl per well. At the end of the process, the matrix is transformed into a porous hydroscaffold ready for use. A 3D porous scaffold may be commercially obtained under the reference BIOMIMESYS® Liver (HCS Pharma).

The matrix (hydroscaffold) has pores having a pore size of about 200 μm, measured for example as disclosed in Louis et al. (*Biotechnol. Bioeng.,* 2017, 114: 1813-1824).

Differentiation of hiPSCs into Liver Organoids (LO) in 3D-Porous Hydroscaffold 100 000 hiPSCs were seeded per wells, in 10 μl of medium StemMACS iPS-Brew (Miltenyi-130-104-368), and ROCK inhibitor, Y27632, (0.01 mM) in 3D-porous hydroscaffold BIOMIMESYS® coated 96-well plates.

After seeding, the hiPSCs were incubated for 10 min at 37° C. under hypoxic conditions (4% $O_2$, 5% $CO_2$). Then, 190 μl of culture medium StemMACS iPS-Brew (Miltenyi-130-104-368) was added, qs 200 μl. The cells were then incubated under hypoxic conditions (4% $O_2$, 5% $CO_2$) at 37° C. for 3 days before initiating the differentiation protocol on day 0. All media changes were made by removing 100 μl/well of culture medium and then addition of 100 μl/well of fresh medium.

Liver organoids (LO) were used 3 days later (short duration) or 2 weeks later (long duration) after the end of the differentiation process. The differentiation was performed from starting a single hiPSC cell line.

Figure 19:
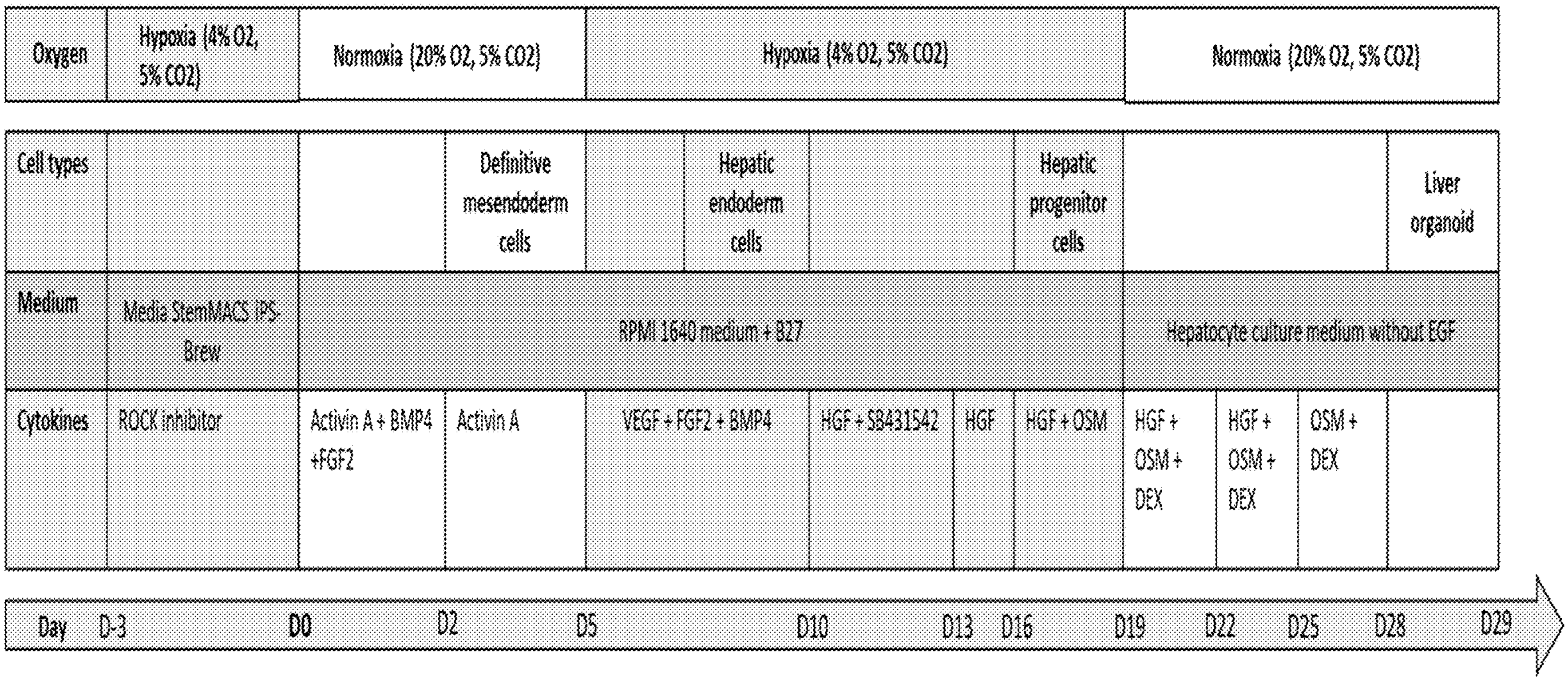
FIG. 19 shows a diagram of the protocol used for the differentiation of hiPSC in liver organoids within a 3D-porous scaffold.

The differentiation protocol was carried out as detailed in TABLE 1 and illustrated in FIG. 19.

TABLE 1

Differentiation of hiPSC in liver organoids in 3D-porous scaffold.

| Day | Oxygen condition | Medium | Cytokines/molecules |
|---|---|---|---|
| D-3 | Hypoxia (4% $O_2$, 5% $CO_2$) | Media StemMACS iPS-Brew (Miltenyi-130-104-368) | ROCK inhibitor (0.01 mM) (Y27632 - TOCRIS-1254/10) |
| D-2 | | Media StemMACS iPS-Brew (Miltenyi-130-104-368) | — |
| D-1 | | — | — |
| D0-D1 | Normoxia (20% $O_2$, 5% $CO_2$) | RPMI 1640 medium (Life Technologies-21875091) supplemented with B27 (with insulin) (Life Technologies-17504044) | Activin A (100 ng/ml) (Miltenyi- 130-115-011)<br>FGF2 (40 ng/ml) (Miltenyi-130-104-922)<br>BMP4 (20 ng/ml) (Miltenyi-130-111-165) |
| D2-D4 | | RPMI 1640 medium (Life Technologies-21875091) supplemented with B27 (with insulin) (Life Technologies-17504044) | Activin A (1 000 ng/ml) (Miltenyi- 130-115-011) |
| D5-D6 | Hypoxia (4% $O_2$, 5% $CO_2$) | RPMI 1640 medium (Life Technologies-21875091) supplemented with B27 (with insulin) (Life Technologies-17504044) | VEGF (200 ng/ml) (Miltenyi-130-109-385)<br>FGF2 (50 ng/ml) (Miltenyi-130-104-922)<br>BMP4 (100 ng/ml) (Miltenyi- 130-111-165) |
| D7-D9 | | RPMI 1640 medium (Life Technologies-21875091) supplemented with B27 (with insulin) (Life Technologies-17504044) | VEGF (200 ng/ml) (Miltenyi-130-109-385)<br>FGF2 (50 ng/ml) (Miltenyi-130-104-922)<br>BMP4 (100 ng/ml) (Miltenyi- 130-111-165) |
| D10-D12 | | RPMI 1640 medium (Life Technologies-21875091) supplemented with B27 (with insulin) (Life Technologies-17504044) | HGF (100 ng/ml) (Miltenyi-130-093-872)<br>SB431542 (10 μg/ml) (Cell Guidance Systems; SM33) |
| D13-D15 | | RPMI 1640 medium (Life Technologies-21875091) supplemented with B27 (with insulin) (Life Technologies-17504044) | HGF (100 ng/ml) (Miltenyi-130-093-872) |
| D16-D18 | | RPMI 1640 medium (Life Technologies-21875091) supplemented with B27 (with insulin) (Life Technologies-17504044) | HGF (100 ng/ml) (Miltenyi-130-093-872)<br>OSM (20 ng/ml) (Miltenyi-130-114-937) |
| D19-D21 | Normoxia (20% $O_2$, 5% $CO_2$) | Hepatocyte culture medium (HCM) (Lonza-CC-3198) without EGF | HGF (100 ng/ml) (Miltenyi-130-093-872)<br>OSM (200 ng/ml) (Miltenyi-130-114-937)<br>DEX (0.5 μM) (SIGMA; D4902) |
| D22-D24 | | Hepatocyte culture medium (HCM) (Lonza-CC-3198) without EGF | HGF (50 ng/ml) (Miltenyi-130-093-872)<br>OSM (200 ng/ml) (Miltenyi-130-114-937)<br>DEX (1 μM) (SIGMA; D4902) |
| D25-D27 | | Hepatocyte culture medium (HCM) (Lonza-CC-3198) without EGF | OSM (200 ng/ml) (Miltenyi-130-114-937)<br>DEX (1 μM) (SIGMA; D4902) |
| D28 | | Hepatocyte culture medium (HCM) (Lonza-CC-3198) without EGF | — |

FGF2: Fibroblast Growth Factor 2
VEGF: Vascular Endothelial Growth Factor
BMP-4: Bone Morphogenetic Protein 4
HGF: Hepatocyte Growth Factor
OSM: Oncostatin M
DEX: Dexamethasone
SB431542: inhibitor of the TGF-β/Activin/NODAL pathway Differentiation of hiPSCs into Liver Organoids (LO) without 3D-Scaffold HiPSCs obtained as previously described were centrifuged for 5 minutes at 300 rpm and resuspended at $0.3 \cdot 10^6$ cells/mL in 10 ml of medium StemMACS iPS-Brew (Miltenyi-130-104-368) supplemented with Y27632 (0.01 mM—TOCRIS-1254/10).

Then, the hiPSCs were transferred in a 20 mL sterile glass bottled fitted with vented cap. After seeding, the hiPSCs were incubated for 24 h at 37° C. under hypoxic conditions (4% $O_2$, 5% $CO_2$) and under stirring using an orbital shaker set at 70 rpm.

The differentiation protocol was started the day after on day 0 and followed the protocol detailed in TABLE 1 and illustrated in FIG. 19.

All media changes were made by removing half of the culture medium and then addition of a fresh medium.

After 28 days of differentiation, the liver organoids prepared in suspension were collected and expression analysis of the AFP, LPA, MYH7 and TNNI3 genes was performed by RT-qPCR.

Example 2: Characterization and Analyses of LO Obtained from hiPSCs (in 2D and 3D Matrices)

3' Sequencing RNA Profiling (3' SRP)

The profiling protocol is carried out as described in Soumillon et al., *bioRxiv* 2014. In short, RNA libraries were prepared using 10 ng of total RNA in 4 μl. The poly(A) tails of the mRNA were labeled with universal adaptors, specific barcoding, and unique molecular identifiers (UMI), during the changing pattern reverse transcriptase (RT) to obtain barcoded cDNAs. Barcoded cDNAs from multiple samples from the LO were then pooled, amplified by PCR and labeled using a transposon-based approach for enriching the 3' region of the cDNA: 100 ng of full-length cDNA were used with the Nextera DNA Sample Preparation Kit (ref FC-121-1030, Illumina) for enriching the 3' region of the cDNA.

The size library was controlled with a 2200 Tape Station System (Agilent Technologies). A 350-800 bp library of barcoded cDNAs was run on an Illumina HiSeq 2500 using a Hiseq Rapid SBS v2-50 cycles kit (ref FC-402-4022) and a Hiseq Rapid PE Cluster v2 kit (ref PE-402-4002) according to the manufacturer's protocol (Denaturation and dilution libraries for HiSeq® and GAIIx protocol, part #15050107 v03, Illumina).

Analysis of the 3' Sequencing RNA Profiling (3' SRP)

The raw fastq pairs were corresponding to the following criteria: the 16 bases of the first reading were corresponding to 6 bases for a barcode designed specifically for the sample and to 10 bases for a unique molecular identifier (UMI). The second reading (58 bases) was corresponding to the captured poly(A) RNA sequence. Demultiplexing of these fastq pairs was warried out to generate a unique fastq for each of the 96 samples. These fastq files were then aligned with bwa on the refseq reference mRNA sequences and the mitochondrial genomic sequence, both available from the UCSC download website.

Gene expression profiles were generated by analyzing the alignment files (.bam) and, for each sample, counting the number of UMIs associated with each gene. Readings aligned on multiple genes, containing more than three mismatches with a reference sequence, or having a poly(A) pattern were rejected. Finally, a matrix containing the counts of all genes on all samples was produced. The expression values, corresponding to the absolute abundance of mRNAs in all samples, were then ready for further analysis of gene expression.

The R deseq2 package (Love, Huber and Anders, 2014) was then used for differential gene expression analysis.

RNAseq

The quality and integrity of the RNA samples were evaluated using the 2100 bioanalyzer and the Nano LabChip RNA 6000 Series II kit (Agilent Technologies). Poly(A) RNA was purified from total RNA using the NEBNExt Poly(A) mRNA magnetic isolation module (Ref E7490, New England BioLabs).

The library was constructed from 400 ng total RNA using NEBNext® Ultra™ II Directional RNA Library Prep Kit for Illumina® (Ref E7760S, New England BioLabs) according to manufacturer recommendations Version 1.0 (New England BioLabs).

Purifications were performed with SPRIselect beads (Ref B23318, Beckmman Coulter). The size of the library fragments was checked on a D1000 ScreenTape with a 2200 TapeStation system (Agilent Technologies). Libraries with P5-P7 adapters were specifically quantified on LightCycler® 480 Instrument II (Roche Life Science) and standardized with DNA standards (1-6) (Ref KK4903, KAPABIOSYSTEMS—CliniSciences).

Each library was pooled and prepared according to the protocol of denaturation and dilution libraries for Hiseq and GAIIx, part no. 15050107 v02 (Illumina). Pair sequencing (2×75 cycles) was performed with two Rapid Runs on the HiSeq® 2500 (Illumina) system in TruSeq v3 chemistry according to the instructions in the HiSeq® 2500 System Guide, part #15035786 v01 (Illumina).

Construction of the Library

The purified poly(A) mRNAs were enzymatically fragmented (fragmentase) at 94° C. for 15 min to the appropriate size for the preparation of the RNA sequencing library (approximately 300 bp). The cDNA was then synthesized and processed for repair of the 5' ends, phosphorylation, and A-joining of the 3' ends. After ligation of the adapters, the cDNA samples were indexed (NEBNext Multiplex Oligos for Illumina, Refs E7335, E7500, NEB) and amplified for 10 PCR (Polymerase Chain Reaction) cycles.

RNAseq Analysis

After demultiplexing and quality control with fastQC_0.11.2 (Version dated Jun. 6, 2014 on the web site Babraham Bioinformatics), the Illumina adapters were cut with cutadapt-1.2.11 and the readings with a Phred quality score below 30 were filtered with prinseq-lite-0.20.32. The readings were aligned to the reference human genome hg19 with tophat2.0.103, the reading count and differential analysis were performed with Gfold.

Gene Expression Analysis (RT qPCR)

RNA samples were isolated using the RNA extraction kit (MACHEREY-NAGEL). RNA reverse transcription of 1 g from RNA to cDNA was performed using the high-capacity cDNA reverse transcription kit (Applied Biosystems). The conditions were as follows: 10 min at 25° C., then 2 hours at 37° C. Quantitative Polymerase Chain Reaction (qPCR) studies were conducted in triplicate using the III Ultra-Fast Master Mix with high ROX (Agilent). Each qPCR study consisted of 2 seconds at 50° C., 10 seconds at 95° C. followed by 40 cycles of 15 seconds at 95° C. and 60 seconds at 60° C. The cycle threshold was calculated using the default settings of the real-time sequence detection software (Applied Biosystems).

Liver Organoid (LO) Labeling Procedure in BIOMIMESYS®

1. Fastening

The BIOMIMESYS® hydroscaffolds containing the LO were grasped with fine tweezers and placed into a 1.5 ml Eppendorf and washed with PBS (1000 μl/sample). The cells were then fixed with paraformaldehyde (PFA 4% in PBS) for 15 minutes at room temperature (200 μl to 1000 μl). Further to the fixation, the cells were washed 3 times with PBS (1000 μl/sample).

2. Permeabilization

The permeabilization step was adapted according to the localization of the protein target.

For membrane proteins labeling: the BIOMIMESYS™ hydroscaffolds containing the LO were incubated in a Triton buffer (0.5% in PBS (phosphate buffered saline), 1000 μl) overnight at 4° C. on a shaking platform under atmospheric conditions. Subsequently, the cells are washed 3 times in PBS (1000 μl/sample).

For cytoplasmic or nuclear labeling: the BIOMIMESYS™ hydroscaffolds containing the LO were incubated in Triton buffer (1% in PBS, 1000 μl) overnight at 4° C. on a shaking platform under atmospheric conditions. Subsequently, the cells were washed 3 times in PBS (1000 μl/sample).

Saturation of non-specific sites: the BIOMIMESYS™ hydroscaffolds containing the LO were incubated in BSA (bovine serum albumin) solution (1% in PBS, 1000 μl) overnight at 4° C. and then subjected to 2 washes with 0.1% PBS-BSA (1000 μl/sample).

3. Labeling

The primary antibody diluted in 150 μl of 0.1% PBS-BSA solution (antibody concentration was adjusted accordingly, as detailed in TABLE 2) was added and incubated for 3 days at 4° C. on a shaking platform. Subsequently, the cells were washed 3 times with 0.1% PBS-BSA (1000 μl/sample).

After primary antibody labeling, the secondary fluorescent antibody at an adjusted concentration (ALEXA-Fluo secondary antibody at a 1/1000 dilution) in 150 μl of 0.1% PBS-BSA solution was added. A DAPI or Hoechst type DNA label (1 μg/ml final concentration) was added further to the secondary antibody. The cells were then incubated for 3 days at 4° C. in 0.1% PBS-BSA solution, protected from light and washed 3 times with PBS (1000 μl/sample).

TABLE 2

Dilution factors according to primary and secondary antibodies

| Antibody | Reference | Species | Dilution |
|---|---|---|---|
| Albumine | CL2513A | Mouse | 1/10 |
| Desmine | ab32362 | Rabbit | 1/100 |
| E-cadherine | ab1416 | Mouse | 1/200 |
| ZO-1 | ab216880 | Rabbit | 1/200 |
| LHX2 | ab219983 | Rabbit | 1/25 |
| CD31 | ab24590 | Mouse | 1/100 |
| LYVE1 | ab14917 | Rabbit | 1/100 |
| OATP1B1 | ab15442 | Mouse | 1/20 |
| SOX9 | 702016 | Rabbit | 1/50 |
| CFTR | MA1-935 | Mouse | 1/250 |
| Alexa 568 | 11004 | Mouse | 1/1000 |
| Alexa 488 | A11034 | Rabbit | 1/1000 |

Imaging

For imaging, two types of apparatus were used: the imageXpress micro confocal system of (Molecular Devices—ImageXpress Micro Confocal High Content Screening System) integrated on the screening platform (HCS Pharma (Loos)) for fluorescence or a bi-photonic microscope of the APEX platform (Nantes—ONIRIS-Microscope Multiphotonique Nikon AIR MP+) for fluorescence and detection of collagen I in liver organoids.

CYPs (Cytochrome Enzymes)

1. Induction of CYPs

PHH and LO grown in 96-well plates were treated by adding 200 μl/well and HLCs in 6-well plates by adding 1 ml/well of CYP's inductors in a hepatocyte culture medium (HCM) without EGF (Lonza—CC-3198).

CYPs were induced by different types of inducers (SIGMA) at different concentrations for 3 days (as detailed in TABLE 3): Omeprazole (50 μM), Rifampicin (10 μM), Imidazole (500 μM), Phenobarbital (500 μM) and CITCO (1 μM). A control condition (namely "basal") is performed with DMSO 0,100 instead of inducer.

TABLE 3

List of CYP's inductors

| CYP450 | Inductors | Reference |
|---|---|---|
| 1A2 | Omeprazole | 19329 |
| 3A4 | Rifampicin | R3501 |
| 2B6 | Phenobarbital | Sanofi (Gardenal) |
| | CITCO | I5513 |
| 2D6 | Omeprazole | 19329 |
| | Rifampicin | R3501 |
| | Imidazole | I5513 |
| 2C9 | Rifampicin | R3501 |

2. Substrates of CYPs

PHH and LO grown in 96-well plates were treated by adding 200 μl/well and HLC grown in 6-well plates by adding 1 ml/well of CYP' substrates in a hepatocyte culture medium (HCM) without EGF (Lonza—CC-3198).

Cells were treated with different substrates (SIGMA) specific to a given CYP for a period of 4 hours (CYP1A2: phenacetin (50 μM); CYP3A4: testosterone (50 μM); CYP2B6: bupropion (100 μM); CYP2C9: diclofenac (20 μM); and CYP2D6: dextromethorphan (20 μM)) in the presence of salycilamide (3 mM), a phase 2 enzyme inhibitor (as detailed in TABLE 4). A control condition (namely "basal") is performed with DMSO 0.1% instead of inducer. Four hours after the change of medium, 400 μl of medium were recovered in acetonitrile (400 μl) and the cells were stored as dry pellet (−80° C.).

TABLE 4

List of products, substrates and internal standards (SI)

| CYP450 | Type | Molecule (SIGMA) | Reference |
|---|---|---|---|
| | | Salicylamide | 860417 |
| 1A2 | Substrat | Phenacetin | 77440 |
| | Produit | Acetaminophen | A7085 |
| | SI | D4-Acetaminophen | P-909 |
| 3A4 | Substrat | Testosterone | T1500 |
| | Produit | 6b-OH-Testosterone | H2898 |
| | SI | D3-testosterone | T-034 |
| 2B6 | Substrat | Bupropion | PHR1730 |
| | Produit | OH-bupropion | H3167 |
| | SI | D3-OH-bupropion | H-062 |
| 2C9 | Substrat | Diclofenac | 93484 |
| | Produit | 4OH-Diclofenac | H-052 |
| | SI | 13C6-OH-Diclofenac | H-053 |
| 2D6 | Substrat | Dextromethorphan | D2531 |
| | Produit | Dextrorphan | D034 |
| | SI | D3-Dextrorphan | D-041 |

Global Metabolomics Analysis

PHH and LO grown in 96-well plates were treated by addition of 200 μl/well and HLC grown in 6-well plates by addition of 1 ml/well of hepatocyte culture medium (HCM) without EGF (Lonza—CC-3198). 48 hours after media change, 400 μl of medium were recovered in acetonitrile (400 μl) and the cells were stored as dry pellet (−80° C.).

Testosterone Metabolism Analysis

PHH and LO grown in 96-well plates were treated by addition of 200 μl/well and HLC in 6-well plates by addition of 1 ml/well of hepatocyte culture medium (HCM) without EGF (Lonza—CC-3198). Prior to testosterone treatment, CYP3A4 was induced or not by rifampicin for 3 days. The medium was renewed each day. Then, PHH, LO and HLC were treated with 50 μM of testosterone. 24 hours after testosterone treatment, 400 μl of medium were recovered in acetonitrile (400 μl) and the cells were stored as dry pellet (−80° C.).

Mass Spectrometry

1. Evaluation of CYP Activity by Mass Spectrometry

The concentrations of CYP-dependent metabolites of interest (CYP1A2: phenacetin→acetaminophen; CYP3A4: testosterone→6-hydroxytestosterone; CYP2B6: bupropion→6-hydroxybupropion; CYP2C9: diclofenac→4'-hydroxydiclofenac; and CYP2D6: dextromethorphan→dextrorphan) were determined by liquid chromatography and tandem mass spectrometry (LC-MS/MS).

All solvents used were LC-MS grade and purchased from Biosolve (Valkenswaard, Netherlands). Standard compounds were obtained from Sigma Aldrich (Saint-Quentin Fallavier, France). A set of reference standard solutions was prepared and diluted serially in acetonitrile to obtain seven standard solutions ranging from 0.01 to 1.0 μmol/L. A pool of exogenous internal standard solutions (D4-acetaminophen, $D_3$-testosterone, $D_6$-6-hydroxybupropion, $^{13}C_6$-4'-hydroxydiclofenac and D3-dextrorphan) was prepared at 0.2 μmol/L in acetonitrile and added (400 μL) to the cell supernatants (400 μL) and standard solutions (400 μL).

The samples were vortex-mixed and dried under a gentle stream of nitrogen. The dried samples were finally reconstituted with 100 μL of 25% acetonitrile. Analyses were performed on a Xevo® TQD mass spectrometer with an electrospray interface and a UPLC™ Acquity H-Class® device (Waters Corporation, Milford, MA, USA). Samples (5 μL) were injected onto a BEH-C18 column (1.7 μm, 2.1×50 mm, Waters Corporation) maintained at 60° C. Compounds were separated using a linear gradient from mobile phase B (100% acetonitrile, 0.1% formic acid) to mobile phase A (5% acetonitrile, 0.1% formic acid) at a flow rate of 600 μL/min. Mobile phase B was kept constant for 0.5 min at 1%, increased linearly from 1% to 100% for 3 min, was kept constant for 0.5 min, returned to the initial state for 0.5 min and was kept constant for 0.5 min before the next injection.

The target compounds were then detected by the mass spectrometer with the electrospray interface operating in positive ion mode (capillary voltage, 3 kV; desolvation gas flow rate and temperature (N2), 900 L/h and 350° C.; source temperature, 150° C.). The multiple reaction monitoring mode was applied for MS/MS detection as detailed in TABLE 5.

The surface ratios of the chromatographic peaks between the unlabeled compounds and their respective internal standards constituted the detector responses. Standard solutions were used to plot calibration curves for quantification. Linearity was expressed by the mean $r^2$ which was greater than 0.998 for all compounds (linear regression, 1/x weighting, excluding origin). Data acquisition and processing were performed using MassLynx® and TargetLynx® version 4.1 software (Waters Corporation).

TABLE 5

Multiple Reaction Mode Transitions (MRM) used for LC-MS/MS analysis of CYP450 activity

| CYP450 | Compounds | MRM transition (m/z) | Cone/ collision (V) |
|---|---|---|---|
| CYP1A2 | Acetaminophen | 152.0 → 110.0 | 30/15 |
| | $D_4$-acetaminophen | 156.0 → 114.0 | 30/15 |
| | Phenacetin | 180.0 → 110.0 | 30/35 |
| CYP2B6 | 6-hydroxybupropion | 256.1 → 238.0 | 30/15 |
| | $D_6$-6-hydroxybupropion | 262.1 → 244.1 | 30/15 |
| | Bupropion | 240.0 → 184.0 | 30/12 |
| CYP2D6 | Dextrorphan | 258.1 → 157.0 | 55/38 |
| | $D_3$-dextrorphan | 261.3 → 157.0 | 55/38 |
| | Dextromethorphan | 272.2 → 147.0 | 50/30 |
| CYP3A4 | 6β-hydroxytestosterone | 305.1 → 269.2 | 45/15 |
| | $D_3$-testosterone | 308.2 → 272.2 | 45/15 |
| | Testosterone | 289.2 → 108.9 | 45/25 |
| CYP2C9 | 4'-hydroxydiclofenac | 312.0 → 230.0 | 30/25 |
| | $^{13}C_6$-4'-hydroxydiclofenac | 318.0 → 236.1 | 30/25 |
| | Diclofenac | 296.0 → 214.0 | 30/25 |

2. Metabolite Profiling by Mass Spectrometry

Cellular supernatants (400 μl) were treated with acetonitrile (400 μl), vortex-mixed and dried under a gentle stream of nitrogen. The dried samples were reconstituted with 100 μl of 25% acetonitrile. The samples were then arbitrarily randomized before being analyzed by liquid chromatography with high-resolution mass spectrometry (LC-HRMS), performed on a SYNAPT G2-Si High-Definition MS Q-TOF mass spectrometer, equipped with an electrospray ionization interface operating in positive mode, and a UPLC™ Acquity H-Class® (Waters Corporation). Samples (10 μL) were injected onto a BEH-C18 column (1.7 pam, 2.1×100 mm, Waters Corporation) maintained at 60° C. Metabolites were separated using a linear gradient from mobile phase B (100% acetonitrile, 0.1% formic acid) to mobile phase A (5% acetonitrile, 0.1% formic acid) at a flow rate of 400 μL/min. The mobile phase B was kept constant for 1 min at 1%, increased linearly from 1% to 100% for 15 min, was kept constant for 1 min and returned to the initial state for 1 min and was kept constant for 2 min before the next injection. The full HRMS mode was applied for the detection of metabolites [mass-to-charge ratio (m/z) between 50 and 1200] at a mass resolution of 25,000 and 20,000 full widths at half the maximum for ESI+ and ESI−, respectively. The ionization parameters were: capillary voltage, +2 kV or −1.5 kV; cone voltage, 30 V; desolvation gas flow rate (N2), 900 L/h; and desolvation/source gas temperatures, 550/120° C. An enkephalin leucine solution (2 μg/mL, 50% acetonitrile) was infused at a constant flow rate of 10 μL/min through the LockSpray channel, which corrected the measured m/z throughout the batch (theoretical m/z 556.2771 and 554.2615 in positive and negative mode, respectively). Data acquisition and processing were performed using MassLynx® and MakerLynx® software (version 4.1, Waters Corporation). Peak detection, integration, alignment and normalization were performed using the following optimized parameters: mass window, 0.01 Da; retention time window, 0.1 min; peak width at 5% height, 12 s; peak-to-peak baseline noise, 500 (positive mode) and 100 (negative mode); smoothing, yes; marker intensity threshold, 500 points (positive mode) and 100 points (negative mode); noise removal level, 6 (positive mode) and 3 (negative mode); deisotopic data function, on; and minimum % replication, 50%. During data processing, each specific signal, corresponding to a putative marker, was normalized to the total intensity of the complete response obtained with the sample. PCA (Principal component analysis) and PLS (partial least squares) were performed using the mixOmics package (Rohart et al., 2017) on the following conditions/groups: HLC_ST; HLC_LT; LO_ST; LO_LT; PHH2D_ST and PHH2D_LT. Variables (metabolites) were included in the analysis if at least two replicates of all four per condition provided a signal. Testosterone metabolites were also specifically studied by a targeted analysis performed using TargetLynx® software (version 4.1, Waters Corporation) with a mass tolerance of ±0.001 Da and a retention tolerance of ±0.1 min as shown in TABLE 6.

TABLE 6

Parameters used for LC-HRMS analysis of testosterone metabolites.

| Compounds | Ionization mode | Theoretical m/z (±0.001 Da) | Retention time (±0.1 min) |
|---|---|---|---|
| Testosterone | Positive | 289.2168 | 5.15 |
| Hydroxy-testosterone (1) | Positive | 305.2117 | 3.88 |
| Hydroxy-testosterone (2) | Positive | 305.2117 | 4.01 |
| Hydroxy-testosterone (3) | Positive | 305.2117 | 4.20 |
| Hydroxy-testosterone (4) | Positive | 305.2117 | 4.40 |
| Hydroxy-testosterone (5) | Positive | 305.2117 | 4.61 |
| Testosterone glucuronide | Positive | 465.2488 | 4.43 |
| Hydroxy-testosterone glucuronide (1) | Positive | 481.2438 | 3.36 |
| Hydroxy-testosterone glucuronide (2) | Positive | 481.2438 | 4.04 |

Lipid Metabolism

1. Internalization of LDL (Low Density Lipoprotein)-Bodipy

Treatment with mevastatin (20, 25 and 30 μg/ml) or DMSO (0.1%) was performed for 20 hours after the end of differentiation (Day 28). After treatment, LOs were incubated with LDL-bodipy (Invitrogen, Ref: L3483) for 3 hours (INVITROGEN). Finally, once the incubation with LDL-bodipy was completed, the scaffolds were washed three times with HCM medium (LONZA) at 37° C. and then the cells were fixed with paraformaldehyde (PFA 4% in PBS) for 15 minutes at room temperature. At this stage, the samples can be stored in PBS at 4° C.

2. Accumulation of Lipids

Steatosis was induced by amiodarone at 20 μM or ethanol at 200 nM for 2 days after the end of differentiation (Day 28). After fixation of the cells with paraformaldehyde (PFA 4% in PBS) for 15 minutes at room temperature, the lipids were labelled with Nile Red (50 ng/ml) for 1 hour at room temperature and then washed three times with PBS (1000 μl). At this step, samples can be stored in PBS at 4° C.

3. Apolipoprotein (a) Secretion

Apo(a) secretion was measured in the cell culture medium of liver organoids cultured for at least 24 hours using the Human Apo(a) ELISA Kit (Cell Biolabs, San Diego, USA).

Image Analysis

After the acquisition of different Z-stacks of the LOs, the images were analyzed and quantified by the image analysis software Metaxpress developed by Molecular Devices.

Statistical Analysis

The data were expressed in average±SD. Significant differences between mean values were determined using the Mann-Whitney U-test for comparison of two groups or the paired Student T-test, where appropriate. For the group approach, genes belonging to the same biological function or cell type were known to exhibit correlated expression. Hierarchical clustering was used to detect groups of correlated genes, supported by a statistical method (limma) to detect differential expression between biological conditions.

Example 3: Results

A New 3D Differentiation Protocol in a 3D Hydroscaffold for the Generation of Liver Organoids (LO)

A new protocol for the differentiation of hiPSC into LO in a 3D hydroscaffold has been developed and described in EXAMPLE 1.

During the differentiation process, cell clusters were randomly forming in the hydroscaffold. The cell clusters, which are called LO at the end of the differentiation process, were preferentially distributed around the periphery of the hydroscaffold. At the level of the LO itself, as observed with phalloidin cytoskeleton labeling, these clusters comprised cavities built upon a cell organization and containing collagen I fibers.

The 3D-Porous Hydroscaffold Improves the Differentiation hiPSC into LOs

The impact of the 3D-porous hydroscaffold in differentiation of hiPSCs into LOs was evaluated by comparing the differentiation protocol of TABLE 1 for preparing 3D LOs in absence and presence of the 3D-porous scaffold.

The gene expression of MYH7 and TNNI3, biomarkers of cardiac mesoderm expression, of AFP, fetal biomarker of hepatic differentiation, and of LPA, biomarker of hepatic differentiation were measured by RT qPCR.

Figure 20:
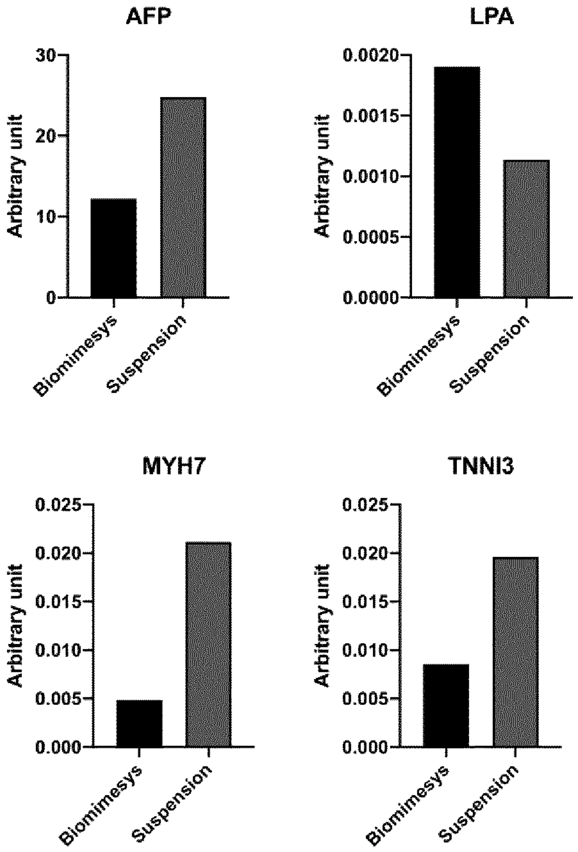
FIG. 20 shows the gene expression level of AFP, LPA, MYH7 and TNNI3 genes in liver organoids (LOs) obtained from the differentiation of hiPSCs within a 3D-porous scaffold (black) or without scaffold, in suspension (grey) following the same protocol in TABLE 1. Ordinate: Change of the mRNA expression level of the AFP, LPA, MYH7 and TNNI3 genes in arbitrary unit analyzed by RT-qPCR. Abscissa: Liver organoids differentiated from hiPSCs within a 3D-porous scaffold (black) or without scaffold (grey).

As shown on FIG. 20, a high-level expression of AFP, MYH7 and TNNI3 genes in the LOs differentiated without 3D-porous scaffold (suspension condition) was observed compared to LOs differentiated in a 3D-porous hydroscaffold.

Further, a low-level expression of LPA was observed in LOs differentiated without 3D-porous hydroscaffold compared to LOs differentiated in the 3D-porous hydroscaffold.

The absence of 3D scaffold results into a defective differentiation, evidenced by a high expression of MYH7 and TNNI3 genes, markers of cardiac mesoderm expression. The high expression of these 2 markers suggests that the absence of the 3D scaffold during the differentiation protocol impacts the differentiation process by driving the cells from the mesendoderm to the cardiac mesoderm.

Also, the absence of 3D scaffold during the differentiation process leads to a higher expression of AFP, a fetal marker of hepatic differentiation. This observation suggests a beneficial effect of the 3D scaffold on hepatocyte maturity.

Finally, a twofold lower expression of the LPA gene in the absence of the 3D scaffold was observed, again suggesting an effect of the 3D scaffold on organoid maturity and functionality.

Altogether these results show that the 3D-porous hydroscaffold contributes to improve the differentiation of hiPSCs into a functional liver organoid.

Characterization of LOs Derived from hiPSCs by Transcriptional Analysis in 3'SRP In order to characterize the cell differentiation, a transcriptional analysis in 3'SRP was performed at different times during differentiation (days 0, 2, 5, 7, 10, 13, 16, 19, 22, 25, 28 and 49).

This analysis allowed observing genes differentially expressed during LOs differentiation. The PCA (Principal component analysis) performed on the 3'SRP transcriptional data shows that the different steps of the differentiation process have been clearly separated at the different times except for days 7 and 10. In addition, it was observed a maintenance of differentially expressed genes two weeks after the end of differentiation (Days 28-49). Further, it has been observed a high expression of NANOG (induced pluripotent stem cells) for days 0 to 2; CER1 (hepatocytes) and NODAL (endoderm) for days 2 to 10; SOX17 (definitive endoderm) for days 5 to 19; TBX3 (hepatoblasts) for days 13 to 22; LIPC (hepatocytes) for days 19 to 49; UGT2B7 (hepatocytes) for days 28 to 49 and PLG (hepatocytes) for days 22 to 49.

Therefore, NANOG expression from day 0 to 2 confirms a loss of pluripotency and thus an engagement in differentiation; SOX17 expression on day 5 showed the establishment of the definitive endoderm and TBX3 expression from day 13 to 22 revealed hepatoblast differentiation.

The data shown here indicates that throughout the differentiation process disclosed here the hiPSC differentiates into definitive endoderm, through the differentiation into mesendoderm cells, which then differentiates in hepatic endoderm cells, and then in hepatic progenitor cells, and then in a liver organoid containing lineages from definitive endoderm (i.e., hepatocytes and cholangiocytes) and mesoderm (i.e., stellate cells and sinusoidal endothelial cells).

RNAseq Comparison of Undifferentiated and Differentiated hiPSCs in Hepatocyte Cells (2D) and Liver Organoids (3D)

RNAseq was then performed on the liver organoids (LOs) and hepatocyte cells (HLC) model at the beginning (day 0) and end of differentiation (HLC/day 20 and LO/day 28). It has been observed a small difference at the beginning (DO) of differentiation for the 2D and 3D hiPSCs but many differences in terms of gene expression at the end of differentiation between HLC (D20) and LO (D28). Indeed, it was observed that 7 448 out of 57 905 genes were differentially expressed between the HLC and LO model. Further, it was observed that groups of genes associated with the liver and liver functions (metabolism of bile, fatty acids, cholesterol, lipoproteins, glucose, insulin, cytochromes and xenobiotics) were more expressed in the LO model than in the HLC model.

Characterization of Liver Organoids by Immunofluorescence

During the analysis of the RNAseq data, it was observed that LHX2, a marker of stellate cells, was more expressed in the LO model. Further, the presence of different cell population types within liver organoids was observed. Indeed, it has been observed from immunofluorescence data a polarization of LOs with the presence of intercellular junction proteins such as Zonulas-Occludens 1 (ZO-1), E-cadherin and xenobiotic efflux transport proteins (OATP1B1). The presence of hepatocytes was observed with albumin labelling; the presence of stellate cells with LHX2 and desmin labelling; the presence of cholangiocytes with CFTR and SOX9 labelling and the presence of sinusoidal endothelial cells with CD31 and LYVE1 labelling compared to negative control without antibodies.

Functional Characterization of the Lipid Metabolism of Liver Organoid

In order to check the functionality of the lipid metabolism of the LOs the capacity of the LO model to accumulate lipids or internalize LDL (Low Density Lipoprotein) was observed.

Figure 1B:
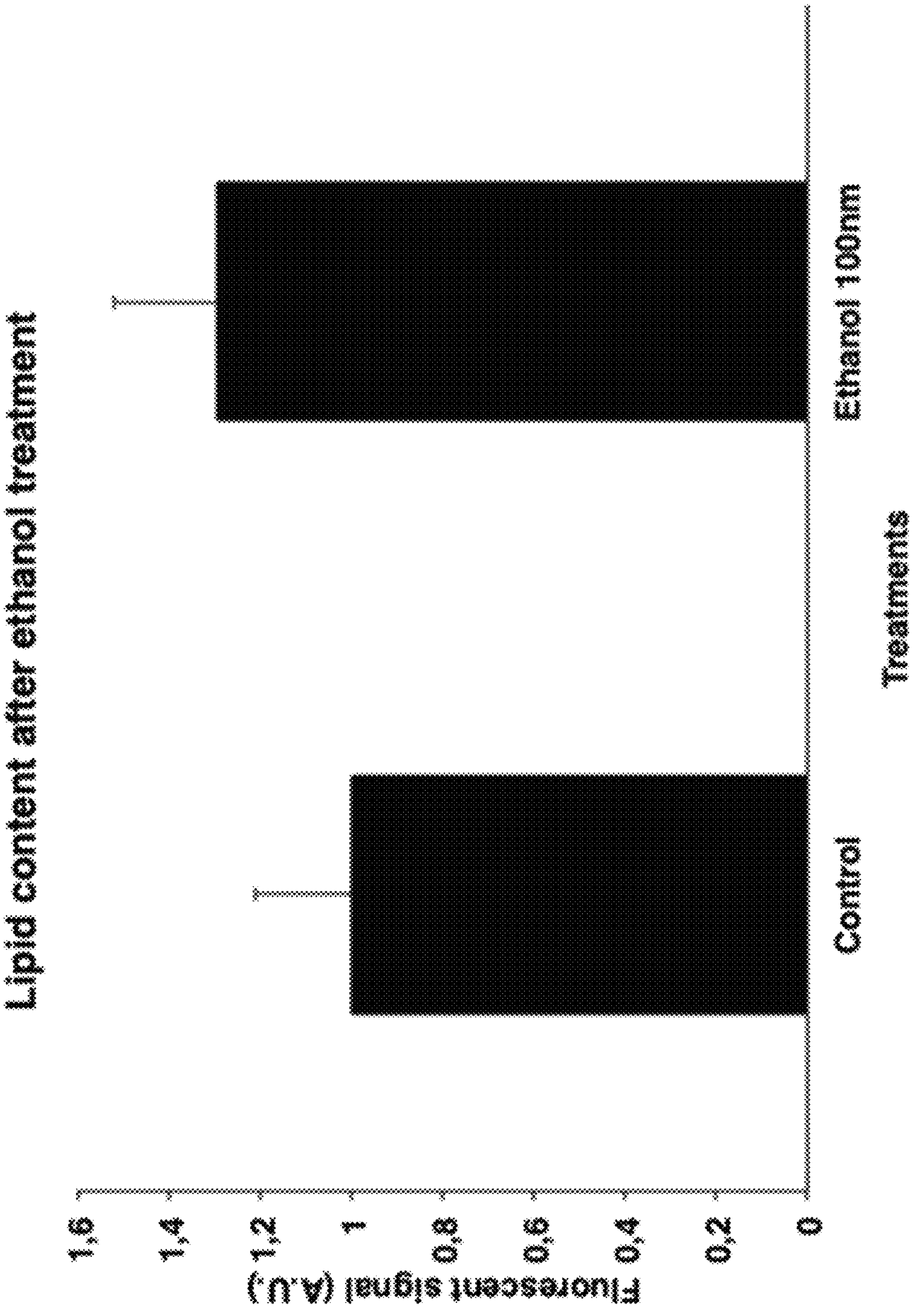
FIG. 1 shows the capacity of liver organoid (LO) to internalize lipids. Data represent the quantification of the lipid content in LO after 2 days of treatment with DMSO (control) or amiodarone (FIG. 1A) or ethanol (FIG. 1B).

The ability to internalize lipids was observed by treatment with amiodarone (40 μM) inducing stress in the endoplasmic reticulum or by treatment with ethanol (100 nM) inducing lipid biosynthesis. Data shown a significative LO response to these two molecules with an increase in lipid accumulation of 60% for amiodarone treatment (FIG. 1A) and 29% for ethanol treatment (FIG. 1B), compared to 0.1% DMSO controls.

Figure 2:
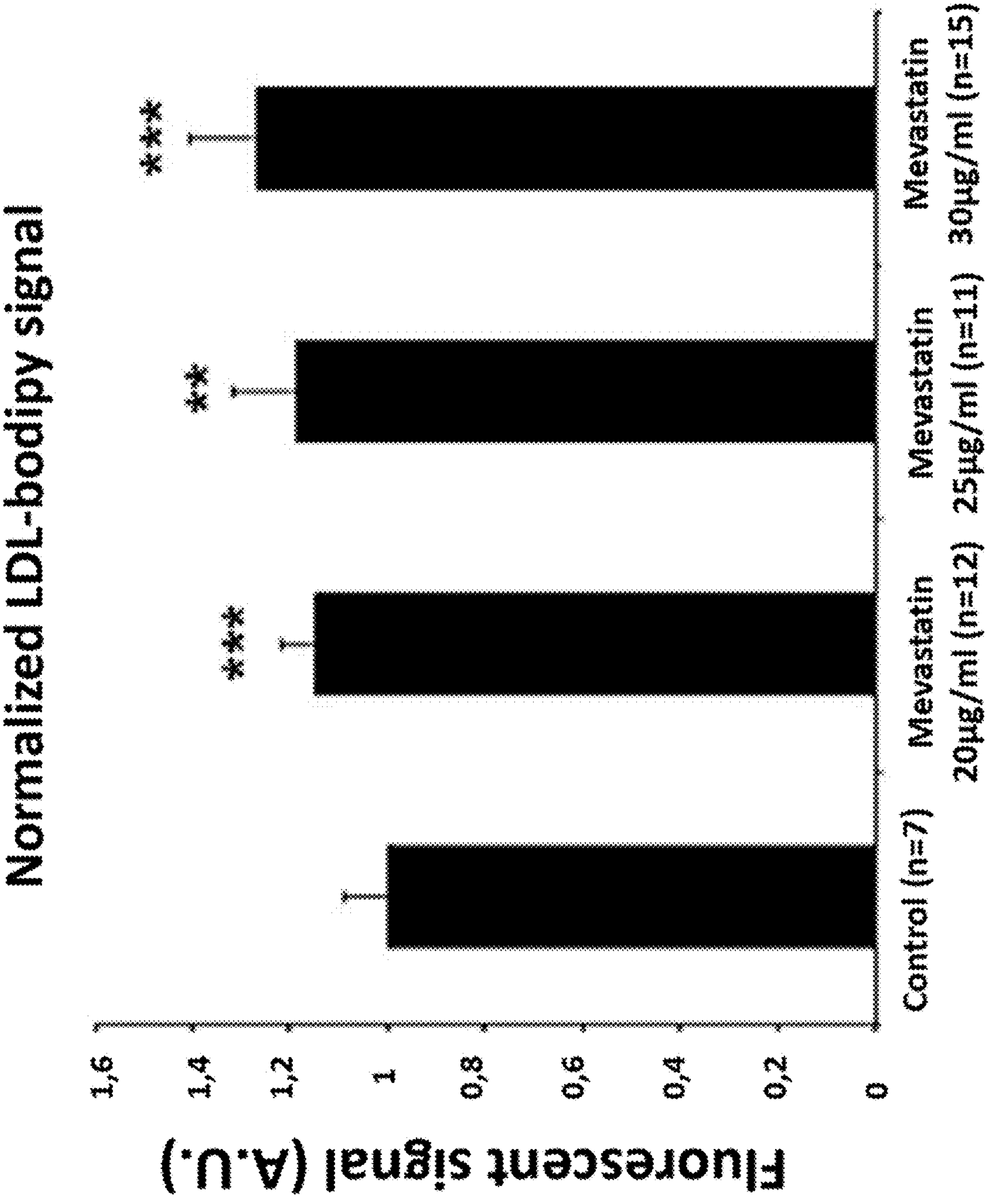
FIG. 2 shows the capacity of LO to internalize low-density lipoprotein (LDL). LO were treated 20 hours with DMSO (control) or with 20, 25 or 30 μg/ml of mevastatin. After treatment, LO were incubated 3 hours with LDL-bodipy. Ordinate: Fluorescence signal (A.U.) of LDL-bodipy. Abscissa (from left to right): (i) Control (DMSO 0.1%); (ii) Mevastatin 20 μg/ml (n=12); (iii) Mevastatin 25 μg/ml (n=11); (iv) Mevastatin 30 μg/ml (n=15). * p-value <0.05;  p-value <0.01; * p-value <0.001.
Figure 3:
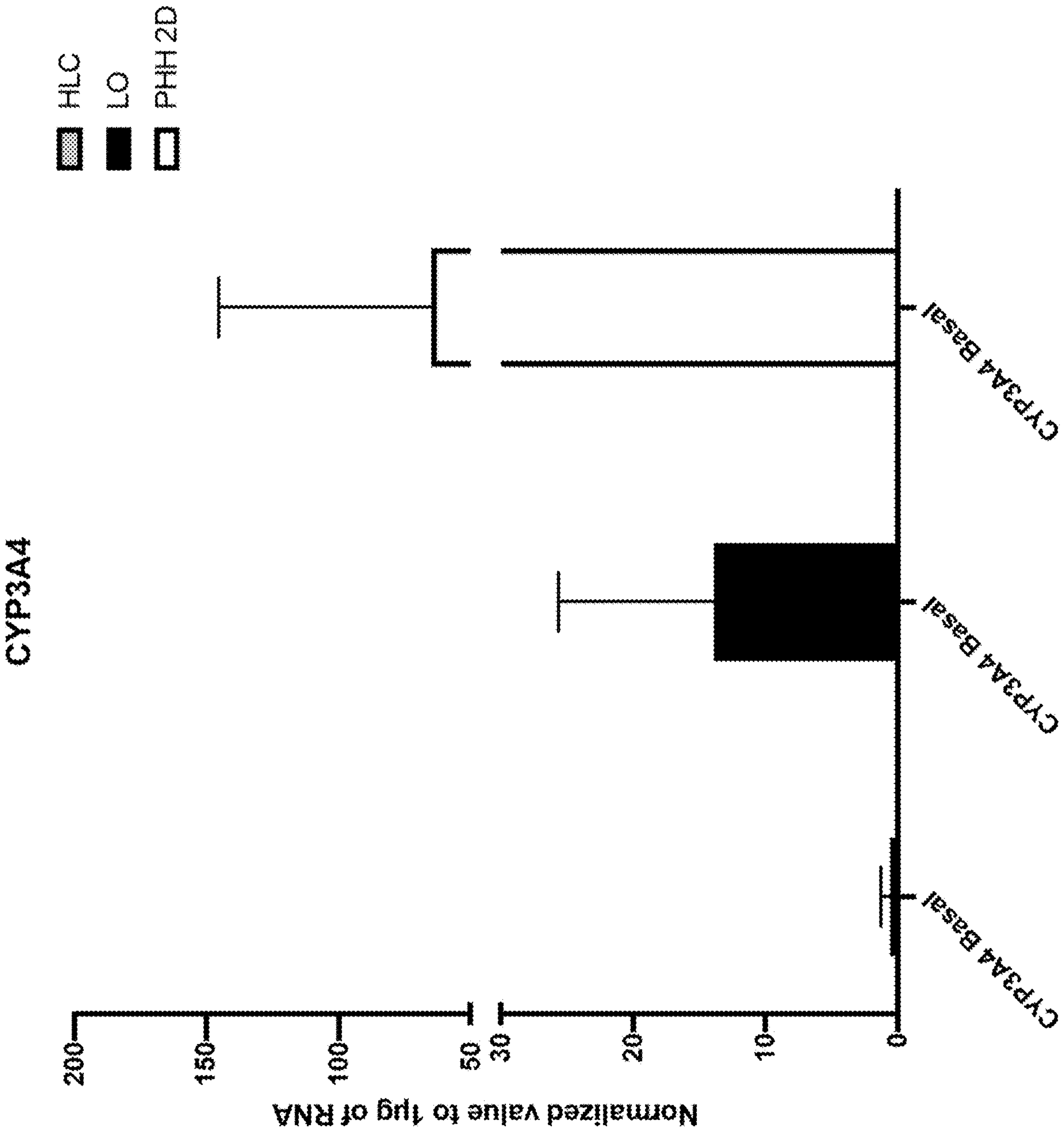
FIGS. 3 to 7 show the expression of CYP3A4 (FIG. 3), CYP1A2 (FIG. 4), CYP2C9 (FIG. 5), CYP2D6 (FIG. 6) and CYP2B6 (FIG. 7) activities by mass spectrometry on liver organoids (LO—black bar), hepatocyte cells in 2D model (PHH—white bar) and primary human hepatocytes (HLC—grey bar) without induction (DMSO 0.1%) after short-term (3 days) cell maintenance. Data represent mean±SD (n=3-4 per condition); * p-value <0.05,  p-value <0.01. Ordinate (FIGS. 3-7): Activity of CYPs. Normalized value to 1 μg of RNA.
Figure 4:
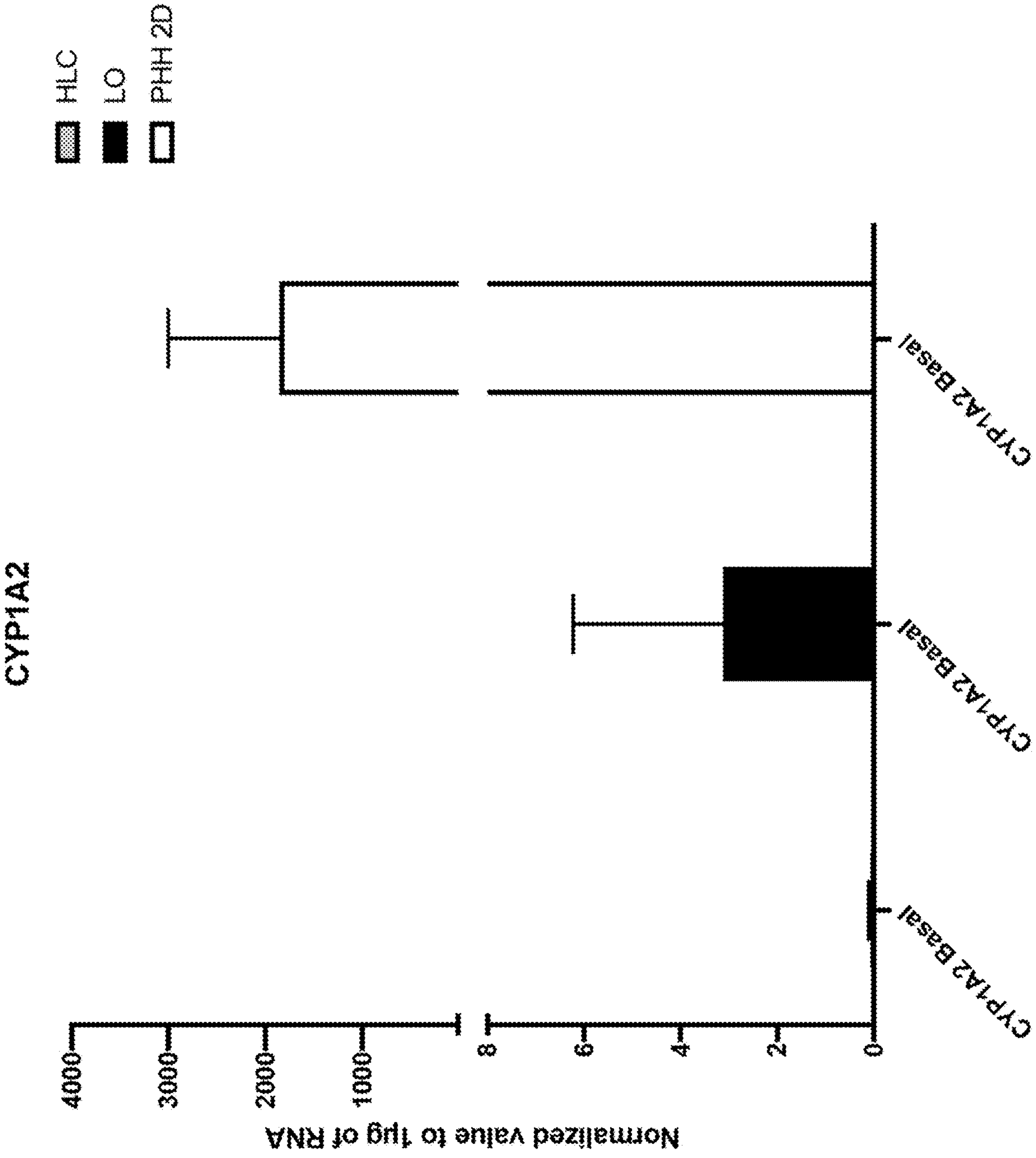
Figure 5:
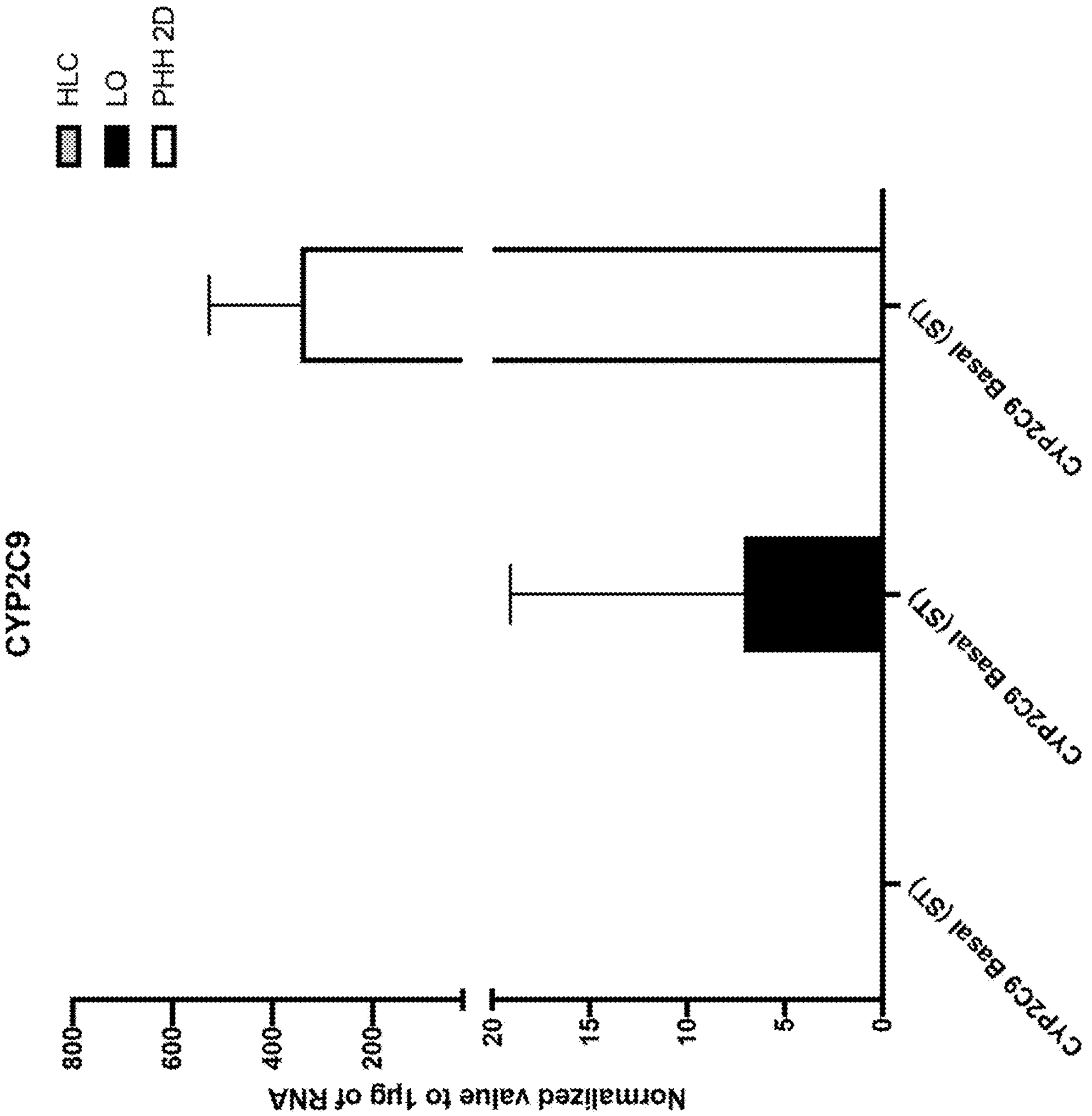
Figure 6:
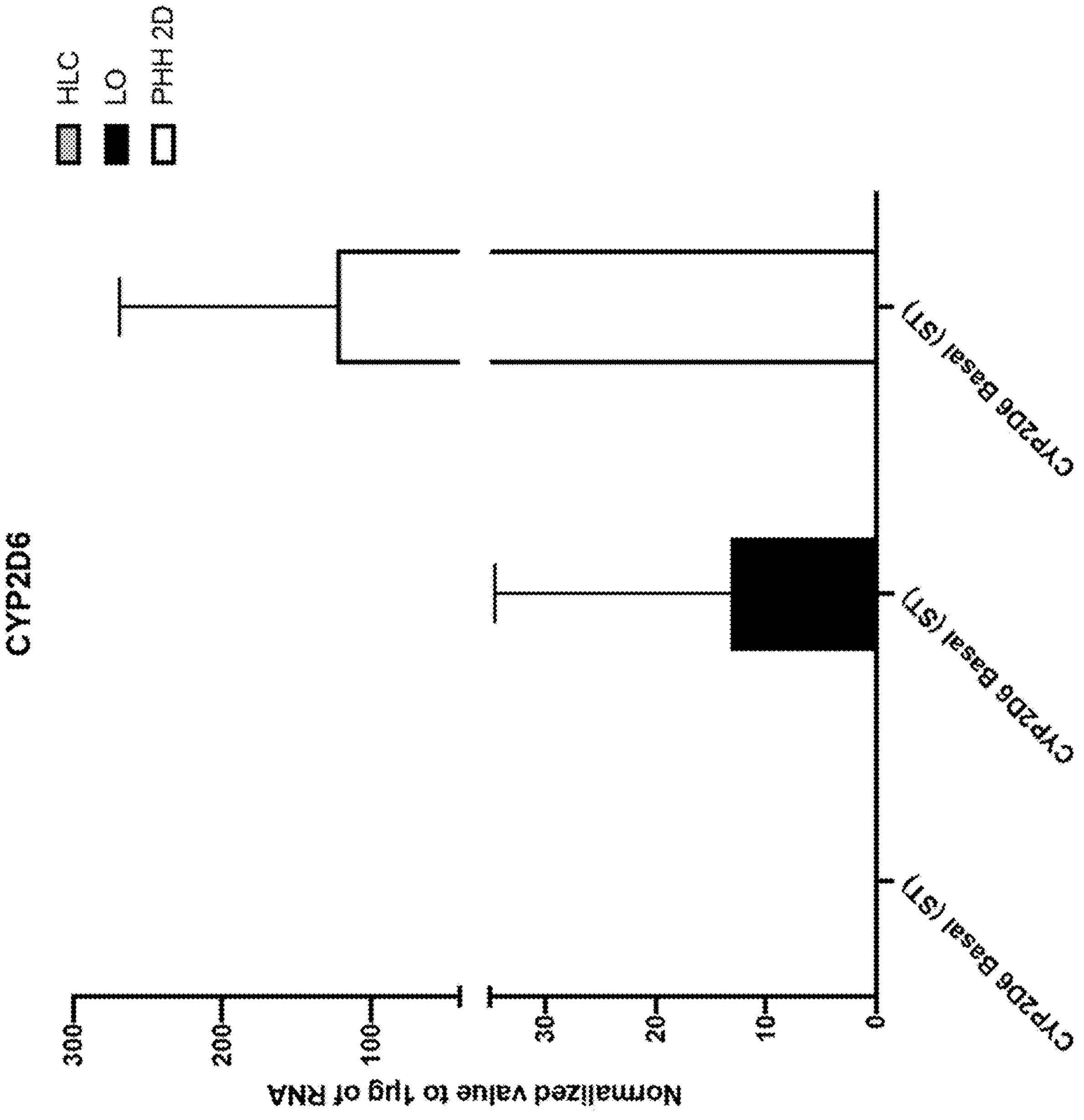
Figure 7:
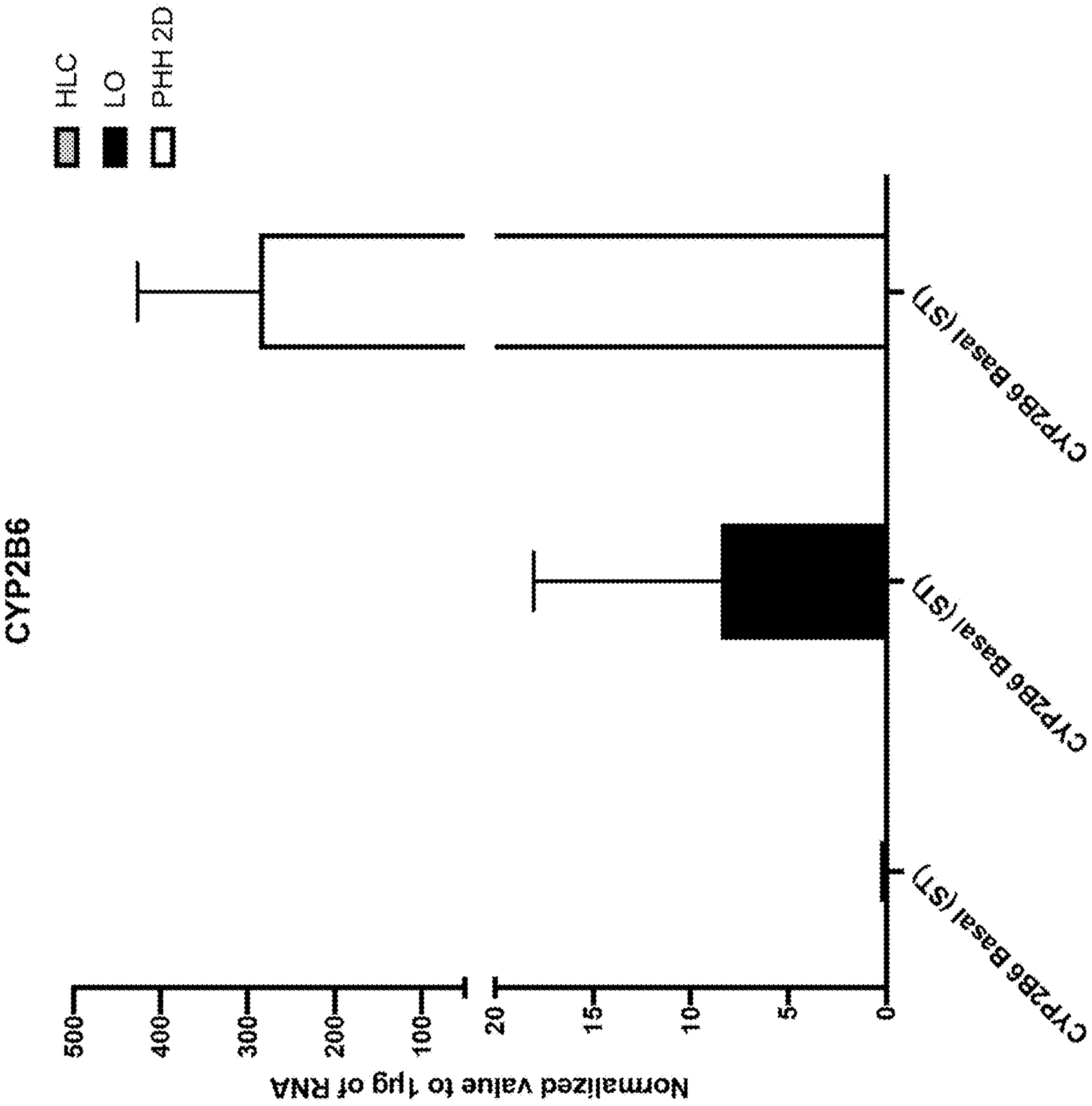
Figure 8A:
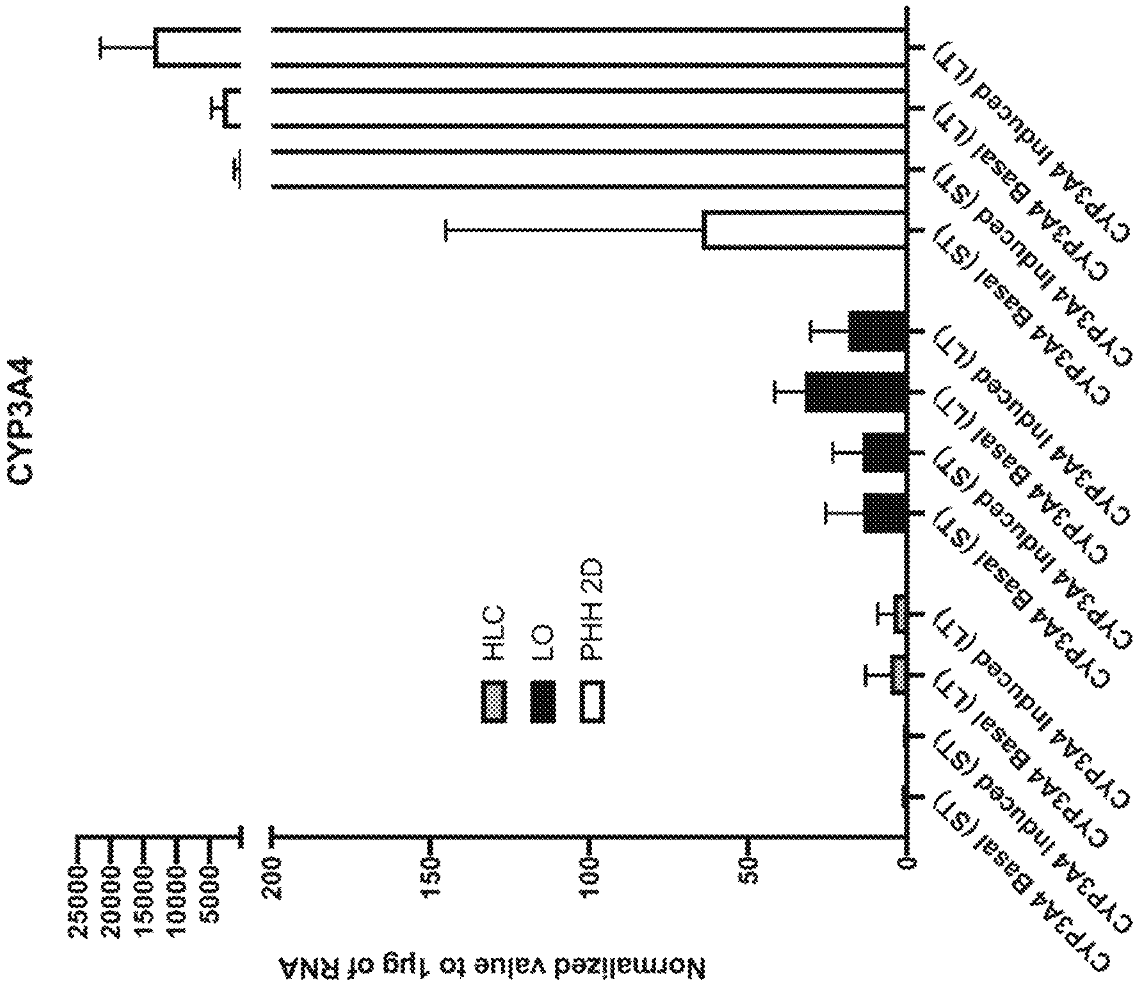
FIG. 8A shows a comparison of the basal and induced activities of the CYP3A4 on HLC, LO and PHH. Ordinate: Activity of CYP3A4 induced by Rifampicin (Induced condition—10 μM) or DMSO 0.1% (basal conditions). Normalized value to 1 μg of RNA. Abscissa (from left to right): (i) Basal condition performed on HLC short-term cell maintenance; (ii) Induced condition performed on HLC short-term cell maintenance; (iii) Basal condition performed on HLC long-term cell maintenance; (iv) Induced condition performed on HLC long-term cell maintenance; (v) Basal condition performed on LO short-term cell maintenance; (vi) Induced condition performed on LO short-term cell maintenance; (vii) Basal condition performed on LO long-term cell maintenance; (viii) Induced condition performed on LO long-term cell maintenance; (ix) Basal condition performed on PHH short-term cell maintenance; (x) Induced condition performed on PHH short-term cell maintenance; (xi) Basal condition performed on PHH long-term cell maintenance; (xii) Induced condition performed on PHH long-term cell maintenance.
Figure 8B:
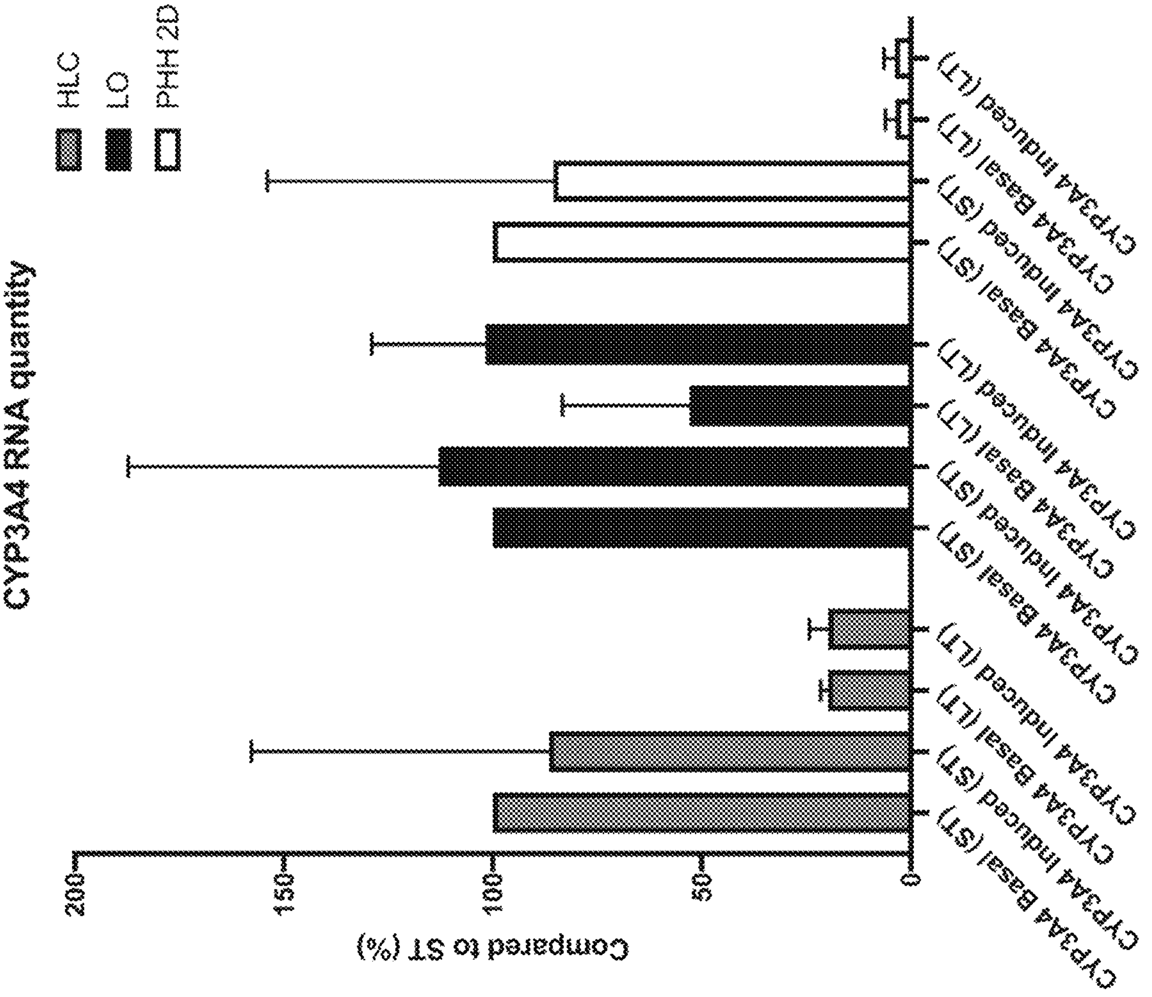
FIG. 8B shows the quantity of CYP3A4 RNA on HLC, LO and PHH in presence of Rifampicin. Ordinate: Percentage of RNA extracted compared to the basal condition in the short-term cell maintenance (100%). Abscissa (from left to right): (i) Basal condition performed on HLC short-term cell maintenance; (ii) Induced condition performed on HLC short-term cell maintenance; (iii) Basal condition performed on HLC long-term cell maintenance; (iv) Induced condition performed on HLC long-term cell maintenance; (v) Basal condition performed on LO short-term cell maintenance; (vi) Induced condition performed on LO short-term cell maintenance; (vii) Basal condition performed on LO long-term cell maintenance; (viii) Induced condition performed on LO long-term cell maintenance; (ix) Basal condition performed on PHH short-term cell maintenance; (x) Induced condition performed on PHH short-term cell maintenance; (xi) Basal condition performed on PHH long-term cell maintenance; (xii) Induced condition performed on PHH long-term cell maintenance.
Figure 9A:
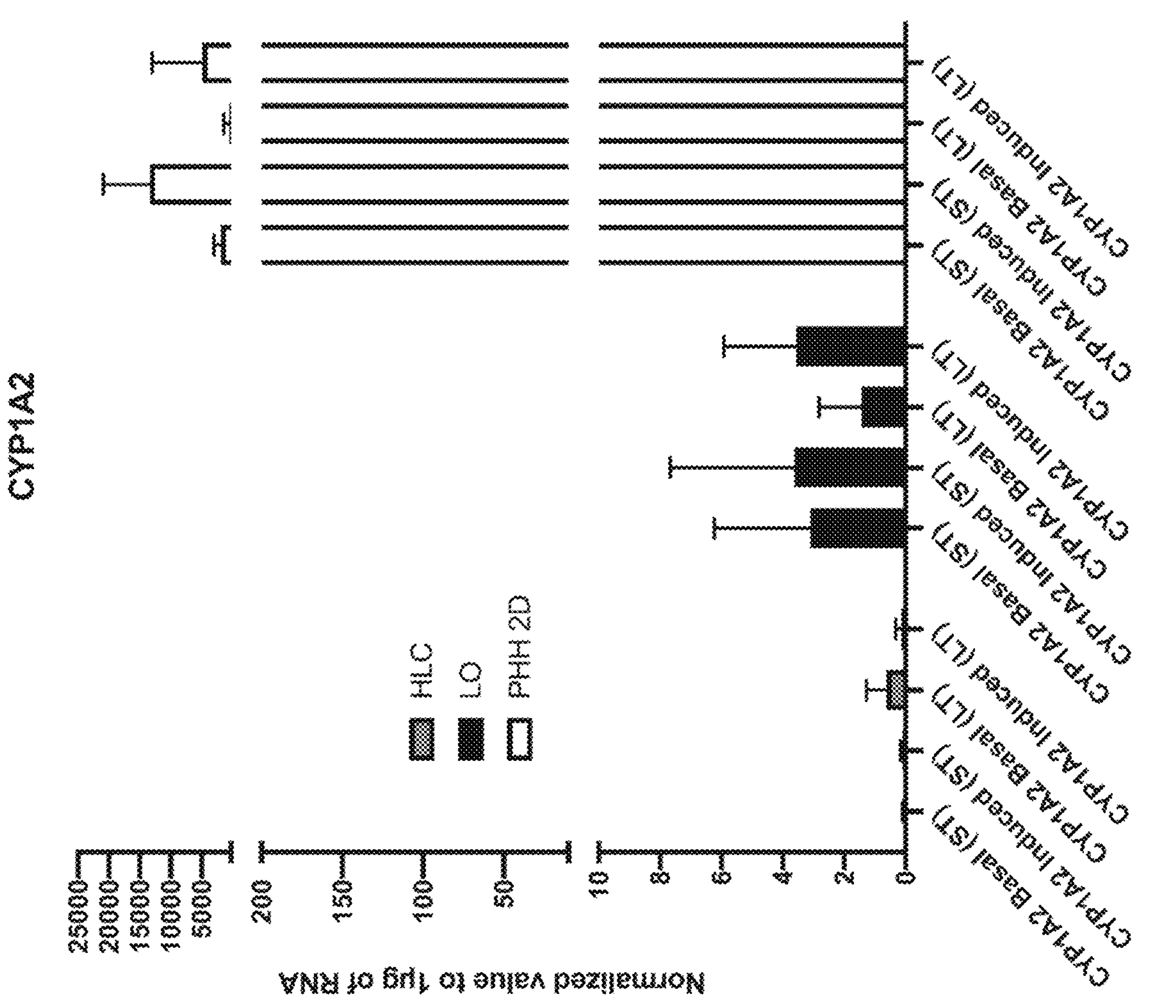
FIG. 9A shows a comparison of the basal and induced activities of the CYP1A2 on HLC, LO and PHH. Ordinate: Activity of CYP1A2 induced by Omeprazole (Induced conditions—50 μM) or DMSO 0.1% (basal conditions). Normalized value to 1 μg of RNA. Abscissa (from left to right): (i) Basal condition performed on HLC short-term cell maintenance; (ii) Induced condition performed on HLC short-term cell maintenance; (iii) Basal condition performed on HLC long-term cell maintenance; (iv) Induced condition performed on HLC long-term cell maintenance; (v) Basal condition performed on LO short-term cell maintenance; (vi) Induced condition performed on LO short-term cell maintenance; (vii) Basal condition performed on LO long-term cell maintenance; (viii) Induced condition performed on LO long-term cell maintenance; (ix) Basal condition performed on PHH short-term cell maintenance; (x) Induced condition performed on PHH short-term cell maintenance; (xi) Basal condition performed on PHH long-term cell maintenance; (xii) Induced condition performed on PHH long-term cell maintenance.
Figure 9B:
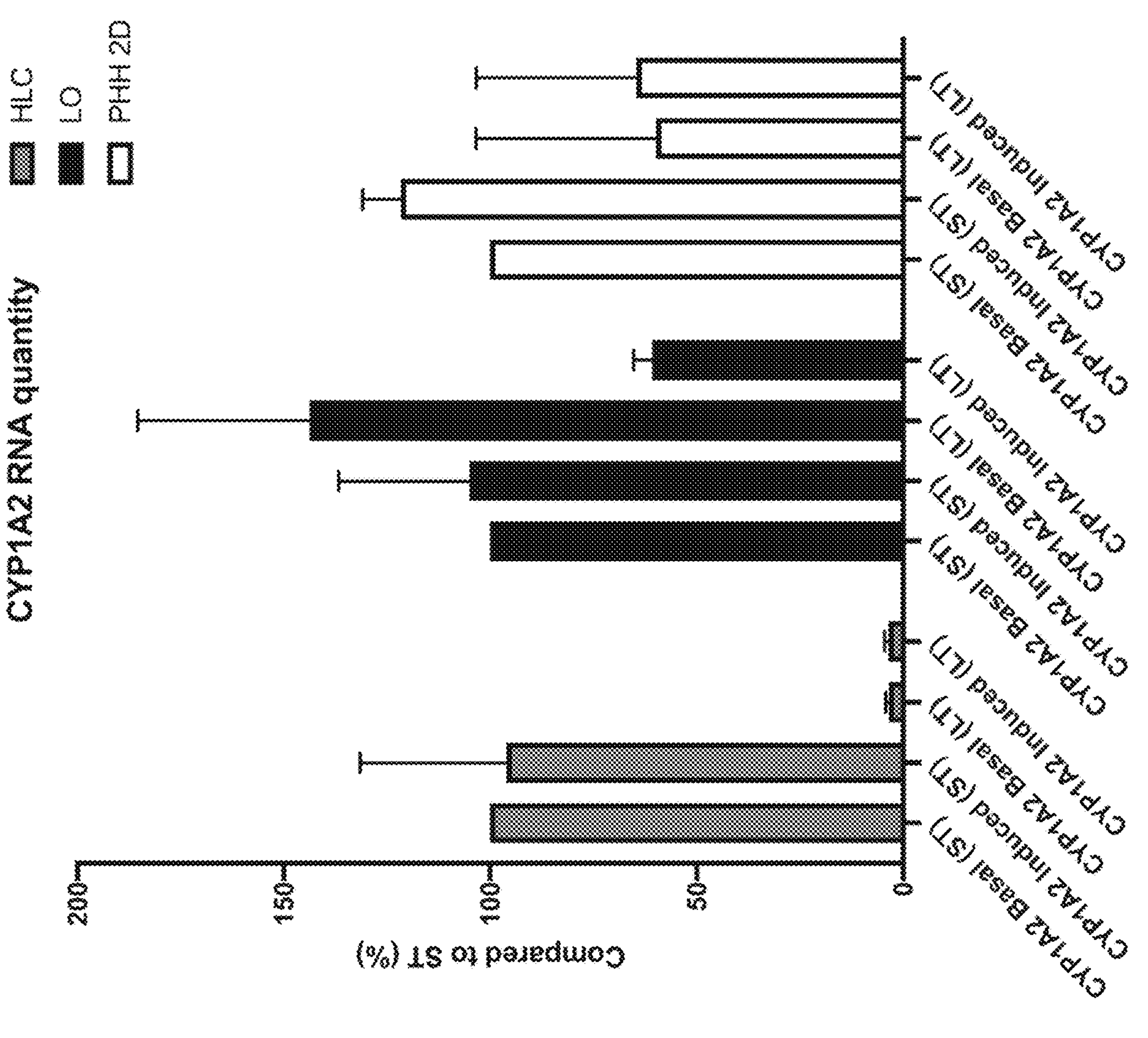
FIG. 9B shows the quantity of CYP1A2 RNA on HLC, LO and PHH in presence of Omeprazole. Ordinate: Percentage of RNA extracted compared to the basal condition in the short-term cell maintenance (100%). Abscissa (from left to right): (i) Basal condition performed on HLC short-term cell maintenance; (ii) Induced condition performed on HLC short-term cell maintenance; (iii) Basal condition performed on HLC long-term cell maintenance; (iv) Induced condition performed on HLC long-term cell maintenance; (v) Basal condition performed on LO short-term cell maintenance; (vi) Induced condition performed on LO short-term cell maintenance; (vii) Basal condition performed on LO long-term cell maintenance; (viii) Induced condition performed on LO long-term cell maintenance; (ix) Basal condition performed on PHH short-term cell maintenance; (x) Induced condition performed on PHH short-term cell maintenance; (xi) Basal condition performed on PHH long-term cell maintenance; (xii) Induced condition performed on PHH long-term cell maintenance.
Figure 10A:
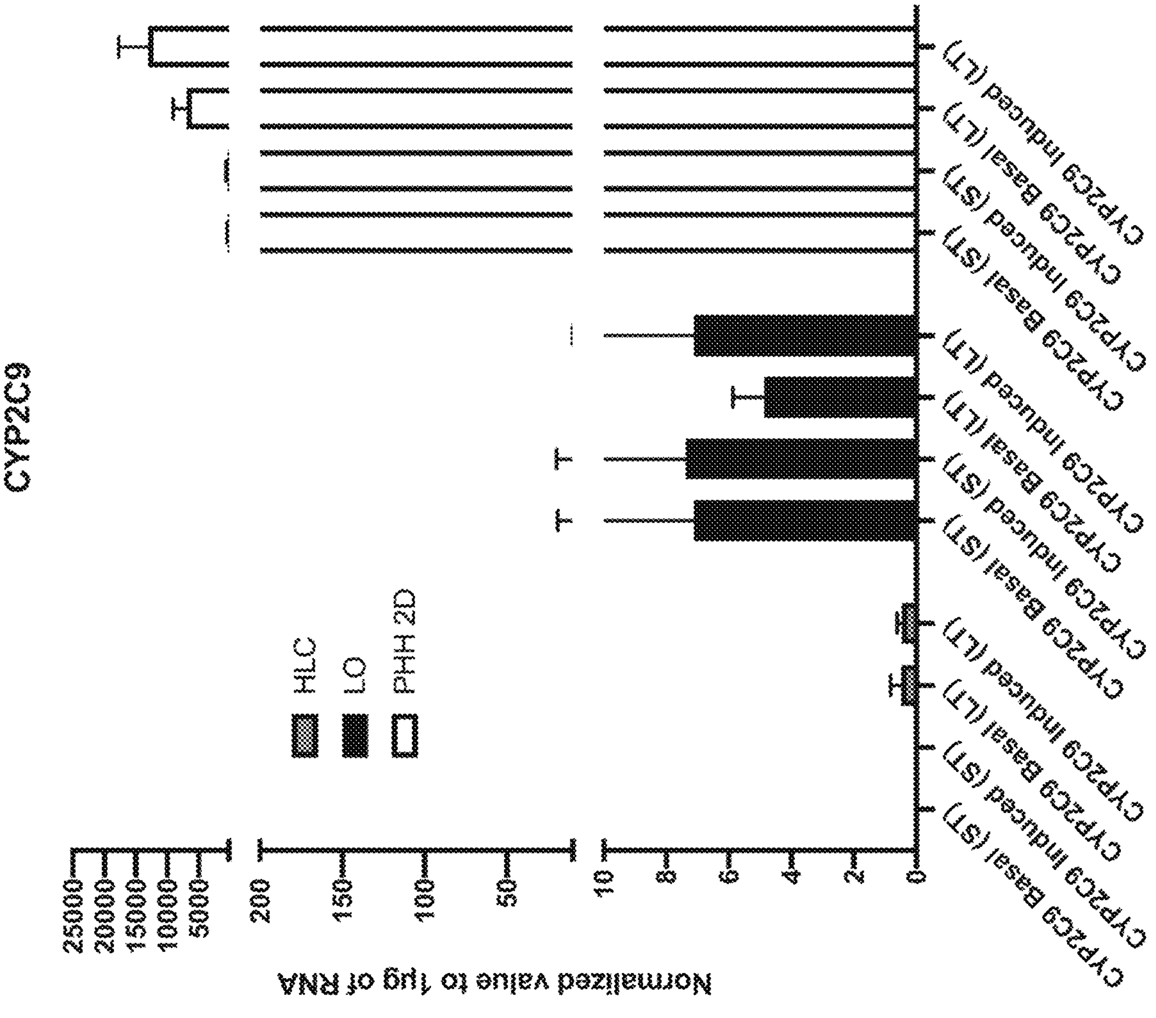
FIG. 10A shows a comparison of the basal and induced activities of the CYP2C9 on HLC, LO and PHH. Ordinate: Activity of CYP2C9 induced by Rifampicin (Induced condition—10 μM) or DMSO 0.1% (basal conditions). Normalized value to 1 μg of RNA. Abscissa (from left to right): (i) Basal condition performed on HLC short-term cell maintenance; (ii) Induced condition performed on HLC short-term cell maintenance; (iii) Basal condition performed on HLC long-term cell maintenance; (iv) Induced condition performed on HLC long-term cell maintenance; (v) Basal condition performed on LO short-term cell maintenance; (vi) Induced condition performed on LO short-term cell maintenance; (vii) Basal condition performed on LO long-term cell maintenance; (viii) Induced condition performed on LO long-term cell maintenance; (ix) Basal condition performed on PHH short-term cell maintenance; (x) Induced condition performed on PHH short-term cell maintenance; (xi) Basal condition performed on PHH long-term cell maintenance; (xii) Induced condition performed on PHH long-term cell maintenance.
Figure 10B:
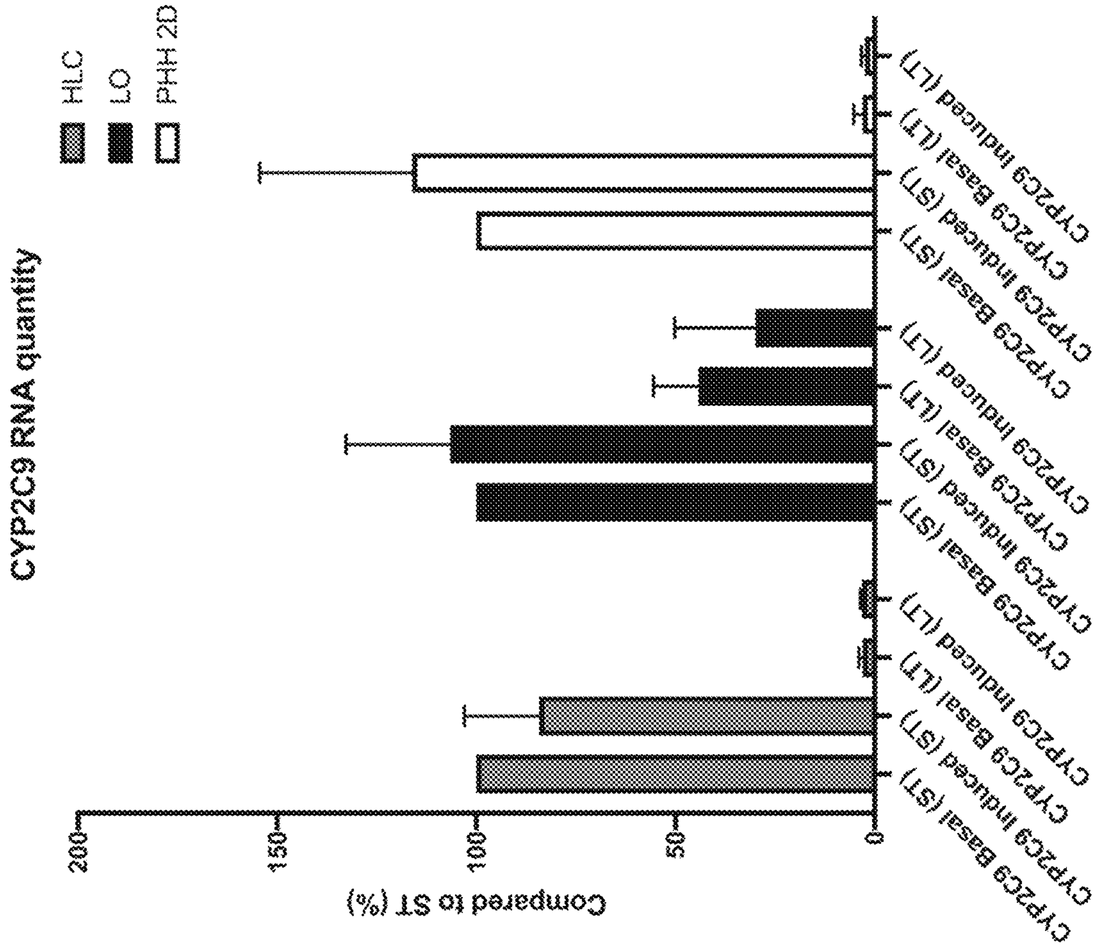
FIG. 10B shows the quantity of CYP2C9 RNA on HLC, LO and PHH in presence of Rifampicin. Ordinate: Percentage of RNA extracted compared to the basal condition in the short-term cell maintenance (100%). Abscissa (from left to right): (i) Basal condition performed on HLC short-term cell maintenance; (ii) Induced condition performed on HLC short-term cell maintenance; (iii) Basal condition performed on HLC long-term cell maintenance; (iv) Induced condition performed on HLC long-term cell maintenance; (v) Basal condition performed on LO short-term cell maintenance; (vi) Induced condition performed on LO short-term cell maintenance; (vii) Basal condition performed on LO long-term cell maintenance; (viii) Induced condition performed on LO long-term cell maintenance; (ix) Basal condition performed on PHH short-term cell maintenance; (x) Induced condition performed on PHH short-term cell maintenance; (xi) Basal condition performed on PHH long-term cell maintenance; (xii) Induced condition performed on PHH long-term cell maintenance.
Figure 11A:
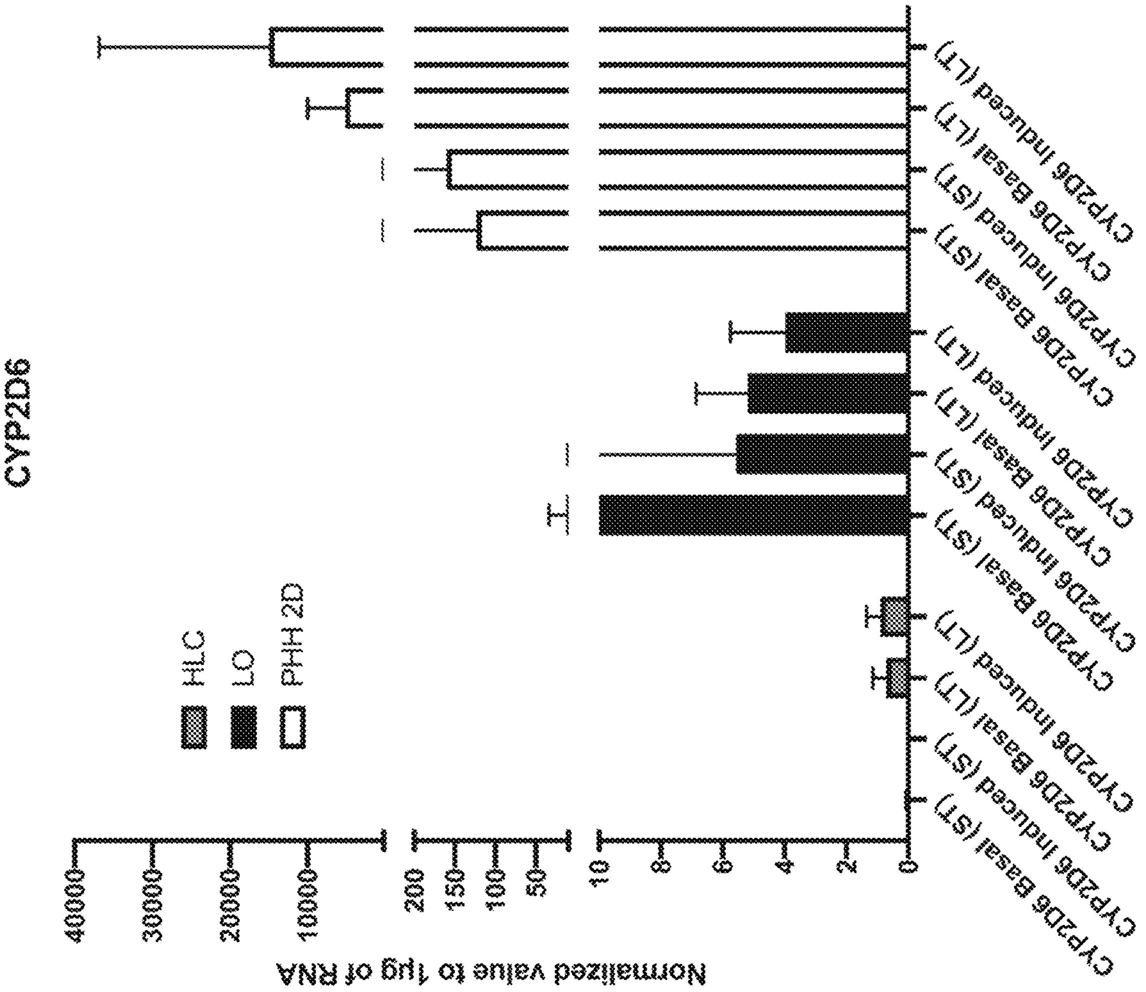
FIG. 11A shows a comparison of the basal and induced activities of the CYP2D6 on HLC, LO and PHH. Ordinate: Activity of CYP2D6 induced by a mix of Omeprazole (Induced condition—50 μM), Rifampicin (Induced condition—10 PM) and Imidazole (Induced condition—500 μM) or DMSO 0.1% (basal conditions). Normalized value to 1 μg of RNA. Abscissa (from left to right): (i) Basal condition performed on HLC short-term cell maintenance; (ii) Induced condition performed on HLC short-term cell maintenance; (iii) Basal condition performed on HLC long-term cell maintenance; (iv) Induced condition performed on HLC long-term cell maintenance; (v) Basal condition performed on LO short-term cell maintenance; (vi) Induced condition performed on LO short-term cell maintenance; (vii) Basal condition performed on LO long-term cell maintenance; (viii) Induced condition performed on LO long-term cell maintenance; (ix) Basal condition performed on PHH short-term cell maintenance; (x) Induced condition performed on PHH short-term cell maintenance; (xi) Basal condition performed on PHH long-term cell maintenance; (xii) Induced condition performed on PHH long-term cell maintenance.
Figure 11B:
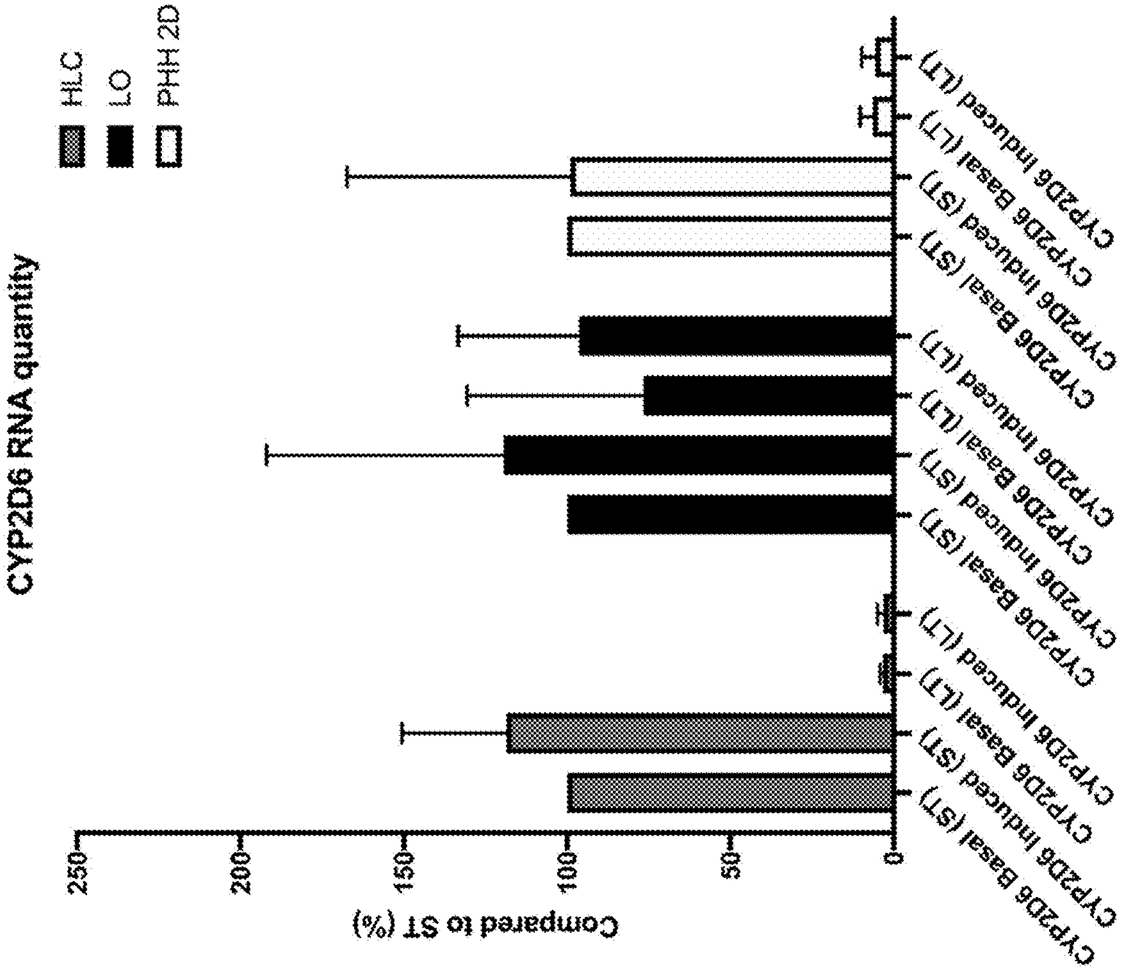
FIG. 11B shows the quantity of CYP2D6 RNA on HLC, LO and PHH in presence of Omeprazole, Rifampicin or Imidazole. Ordinate: Percentage of RNA extracted compared to the basal condition in the short-term cell maintenance (100%). Abscissa (from left to right): (i) Basal condition performed on HLC short-term cell maintenance; (ii) Induced condition performed on HLC short-term cell maintenance; (iii) Basal condition performed on HLC long-term cell maintenance; (iv) Induced condition performed on HLC long-term cell maintenance; (v) Basal condition performed on LO short-term cell maintenance; (vi) Induced condition performed on LO short-term cell maintenance; (vii) Basal condition performed on LO long-term cell maintenance; (viii) Induced condition performed on LO long-term cell maintenance; (ix) Basal condition performed on PHH short-term cell maintenance; (x) Induced condition performed on PHH short-term cell maintenance; (xi) Basal condition performed on PHH long-term cell maintenance; (xii) Induced condition performed on PHH long-term cell maintenance.
Figure 12A:
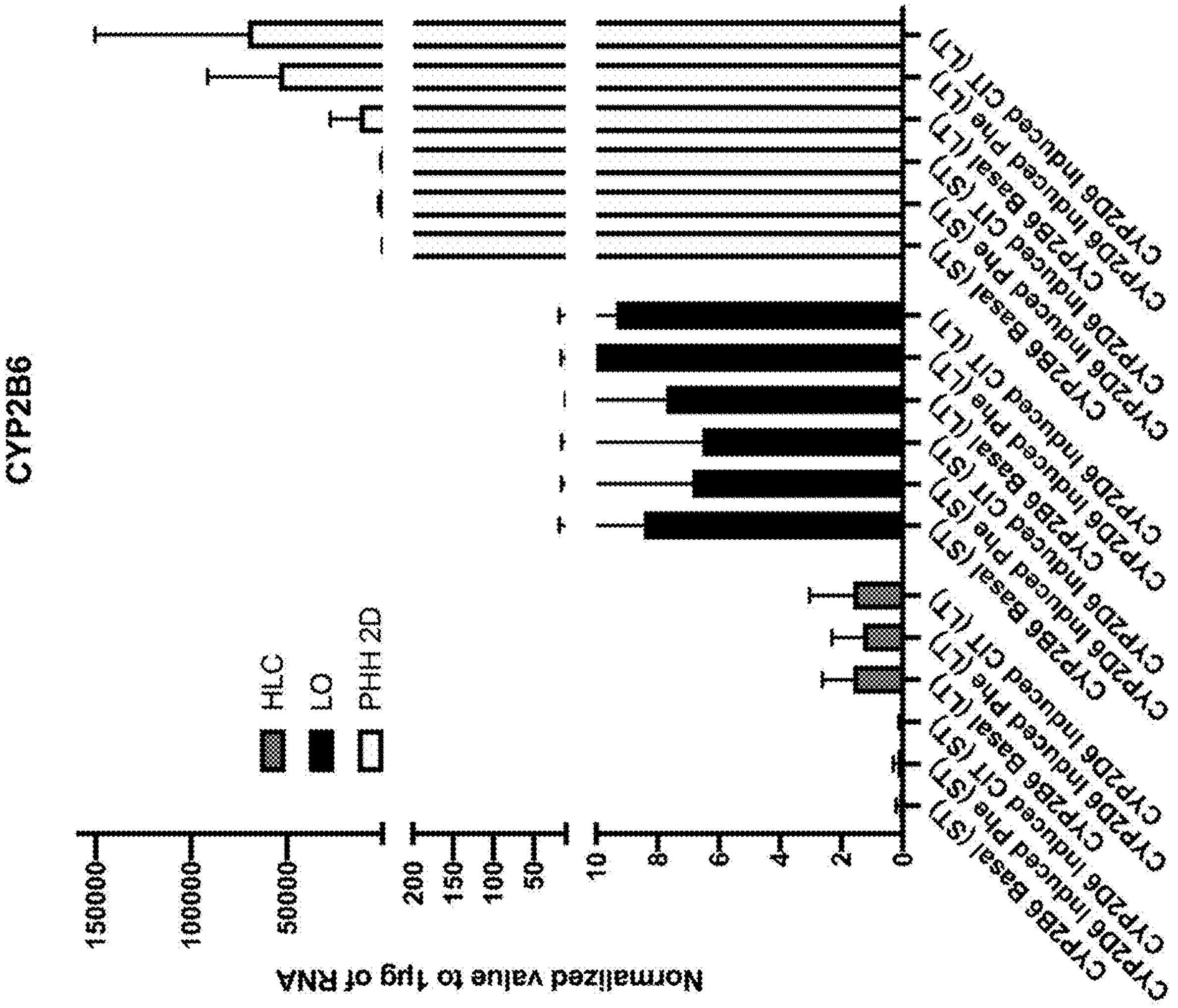
FIG. 12A shows a comparison of the basal and induced activities of the CYP2B6 on HLC, LO and PHH. Ordinate: Activity of CYP2B6 induced by Phenobarbital (Induced condition—500 μM) or CITCO (Induced condition—1 μM) or DMSO 0.1% (basal conditions). Normalized value to 1 μg of RNA. Abscissa (from left to right): (i) Basal condition performed on HLC short-term cell maintenance; (ii) Induced condition with Phenobarbital performed on HLC short-term cell maintenance; (iii) Induced condition with CITCO performed on HLC short-term cell maintenance; (iv) Basal condition performed on HLC long-term cell maintenance; (v) Induced condition with Phenobarbital performed on HLC long-term cell maintenance; (vi) Induced condition with CITCO performed on HLC long-term cell maintenance; (vii) Basal condition performed on LO short-term cell maintenance; (viii) Induced condition with Phenobarbital performed on LO short-term cell maintenance; (ix) Induced condition with CITCO performed on LO short-term cell maintenance; (x) Basal condition performed on LO long-term cell maintenance; (xi) Induced condition with Phenobarbital performed on LO long-term cell maintenance; (xii) Induced condition with CITCO performed on LO long-term cell maintenance. (xiii) Basal condition performed on PHH short-term cell maintenance; (xiv) Induced condition with Phenobarbital performed on PHH short-term cell maintenance; (xv) Induced condition with CITCO performed on PHH short-term cell maintenance; (xvi) Basal condition performed on PHH long-term cell maintenance; (xvii) Induced condition with Phenobarbital performed on PHH long-term cell maintenance; (xviii) Induced condition with CITCO performed on PHH long-term cell maintenance.
Figure 12B:
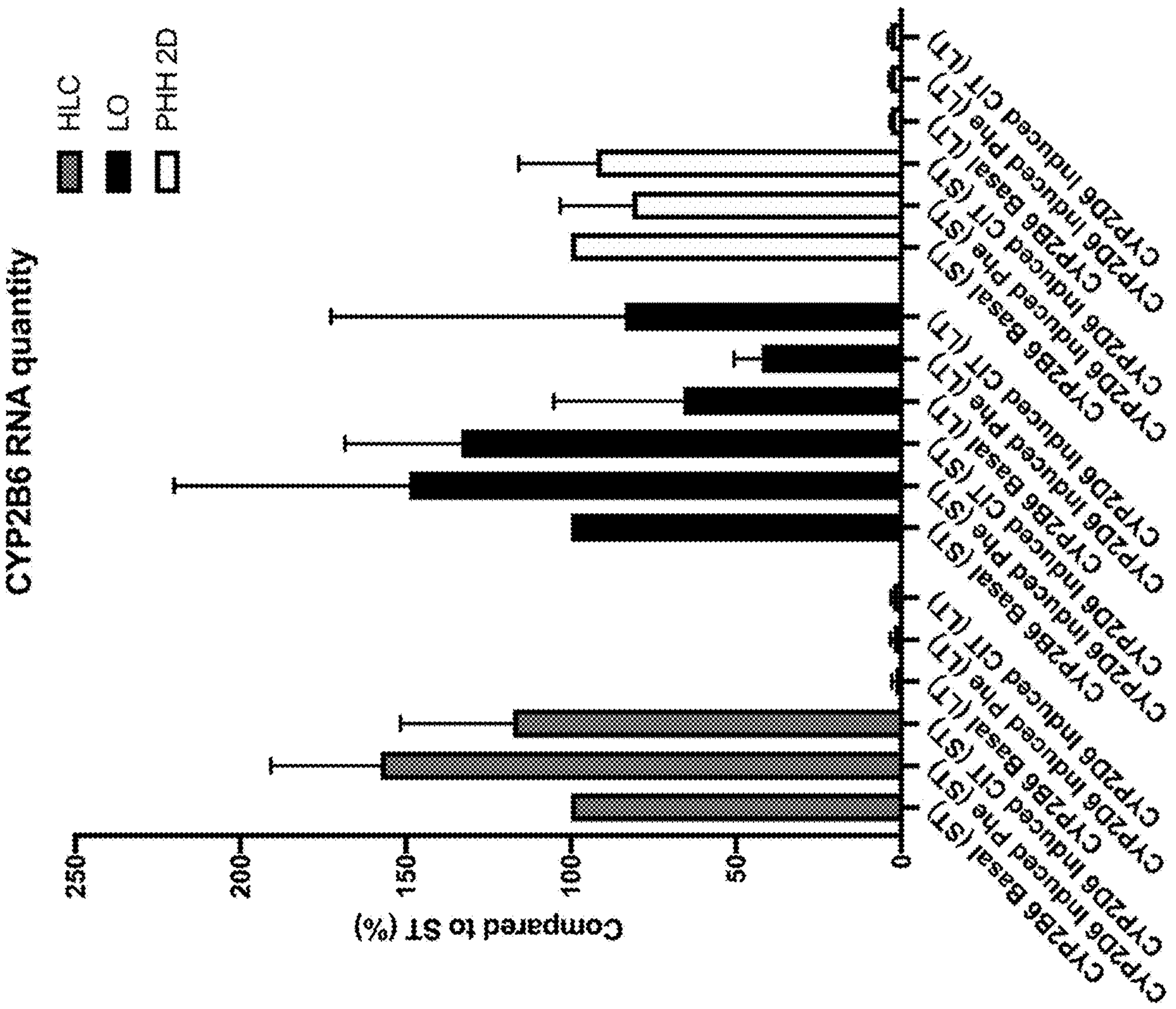
FIG. 12B shows the quantity of CYP2B6 RNA on HLC, LO and PHH in presence of Phenobarbital. Ordinate: Percentage of RNA extracted compared to the basal condition in the short-term cell maintenance (100%). Abscissa (from left to right): (i) Basal condition performed on HLC short-term cell maintenance; (ii) Induced condition with Phenobarbital performed on HLC short-term cell maintenance; (iii) Induced condition with CITCO performed on HLC short-term cell maintenance; (iv) Basal condition performed on HLC long-term cell maintenance; (v) Induced condition with Phenobarbital performed on HLC long-term cell maintenance; (vi) Induced condition with CITCO performed on HLC long-term cell maintenance; (vii) Basal condition performed on LO short-term cell maintenance; (viii) Induced condition with Phenobarbital performed on LO short-term cell maintenance; (ix) Induced condition with CITCO performed on LO short-term cell maintenance; (x) Basal condition performed on LO long-term cell maintenance; (xi) Induced condition with Phenobarbital performed on LO long-term cell maintenance; (xii) Induced condition with CITCO performed on LO long-term cell maintenance. (xiii) Basal condition performed on PHH short-term cell maintenance; (xiv) Induced condition with Phenobarbital performed on PHH short-term cell maintenance; (xv) Induced condition with CITCO performed on PHH short-term cell maintenance; (xvi) Basal condition performed on PHH long-term cell maintenance; (xvii) Induced condition with Phenobarbital performed on PHH long-term cell maintenance; (xviii) Induced condition with CITCO performed on PHH long-term cell maintenance.
Figure 13:
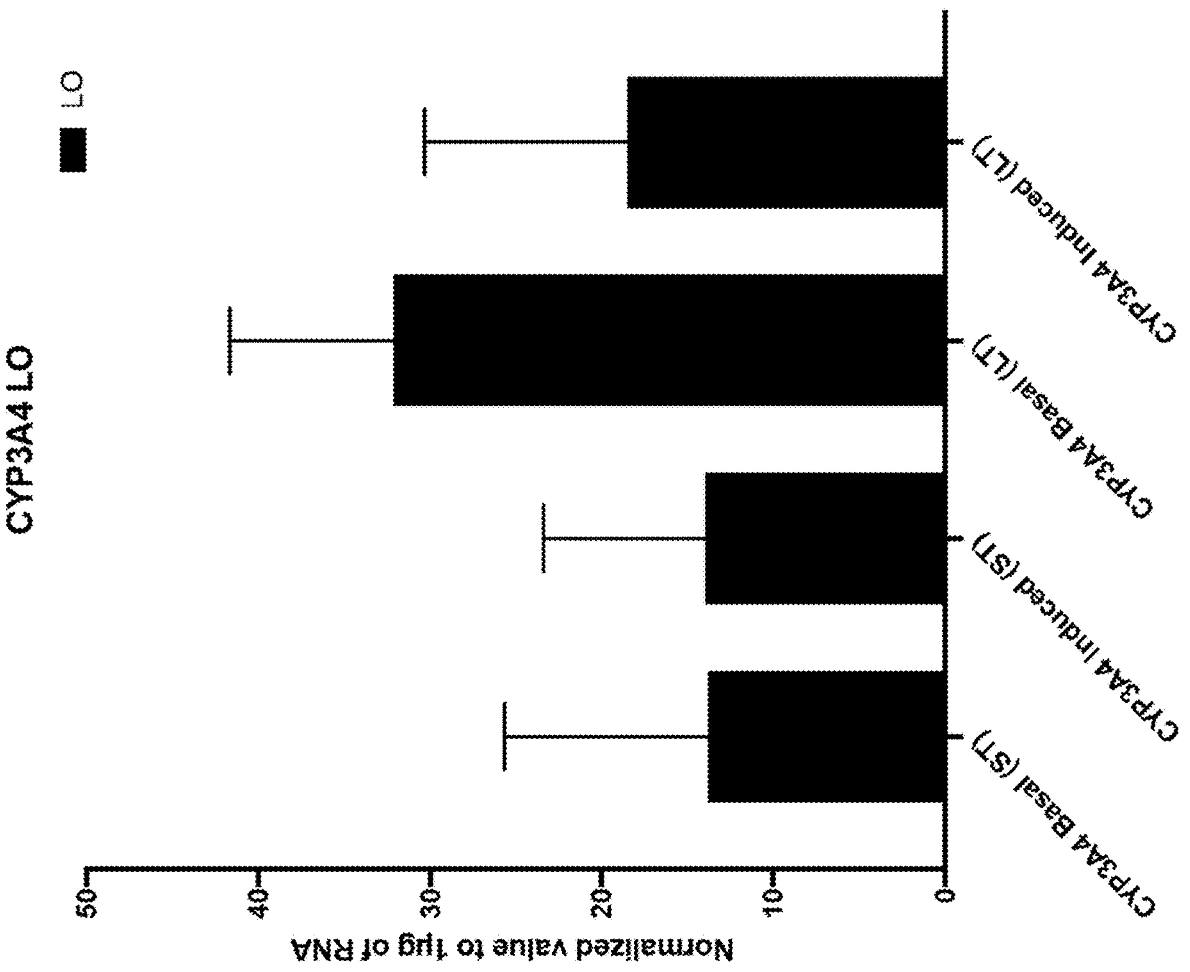
FIGS. 13-17 show the characterization of CYP3A4 (FIG. 13), CYP1A2 (FIG. 14), CYP2C9 (FIG. 15), CYP2D6 (FIG. 16) and CYP2B6 (FIG. 17) activities by mass spectrometry on liver organoids (LO). LO, after short-term (3 days) or long-term (2 weeks) cell maintenance, were incubated with different types of inducers at different concentrations for 3 days: Omeprazole (50 PM), Rifampicin (10 PM), Imidazole (500 μM), Phenobarbital (500 μM), CITCO (1 μM) and DMSO 0.1% (without induction—Basal condition). Data represent mean±SD (n=3-4 per condition); * p-value <0.05, ** p-value <0.01.
Figure 14:
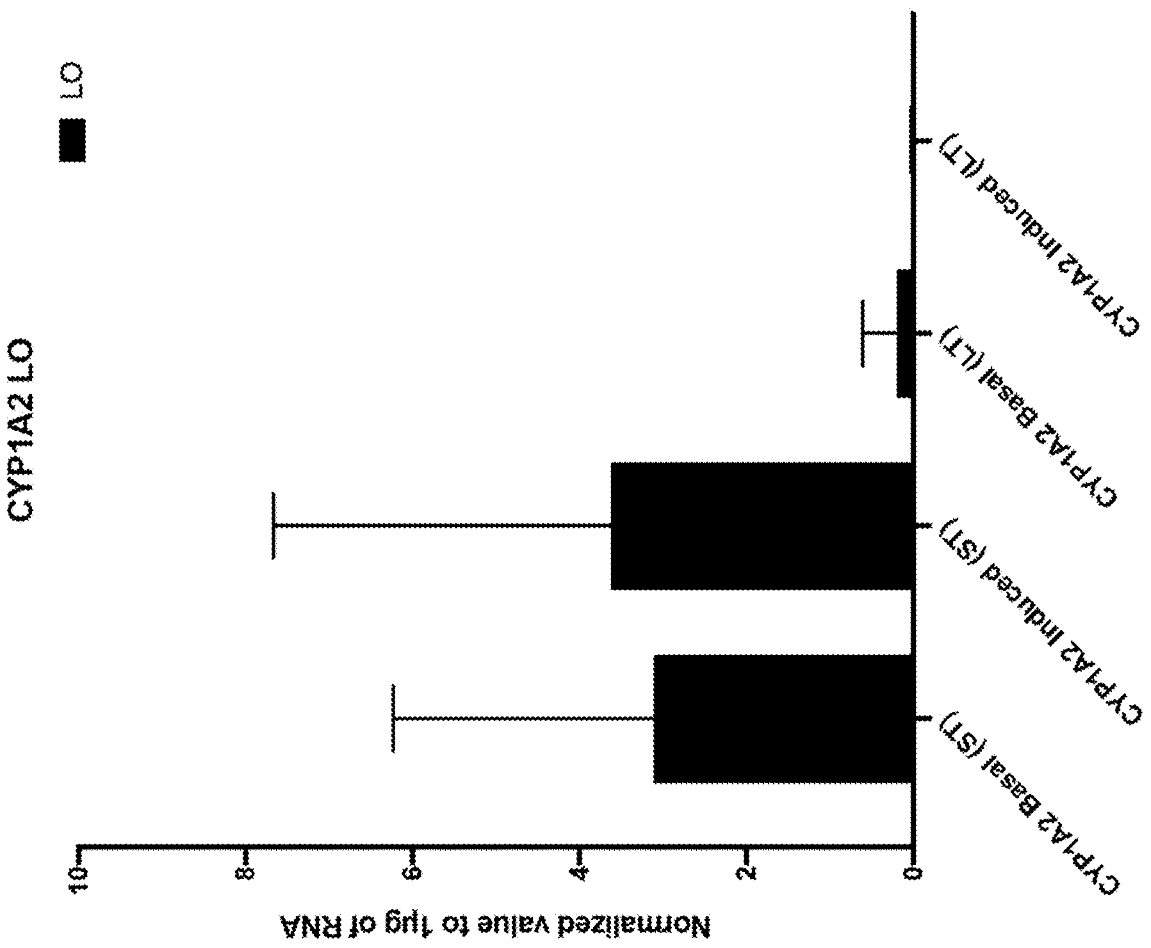
Figure 15:
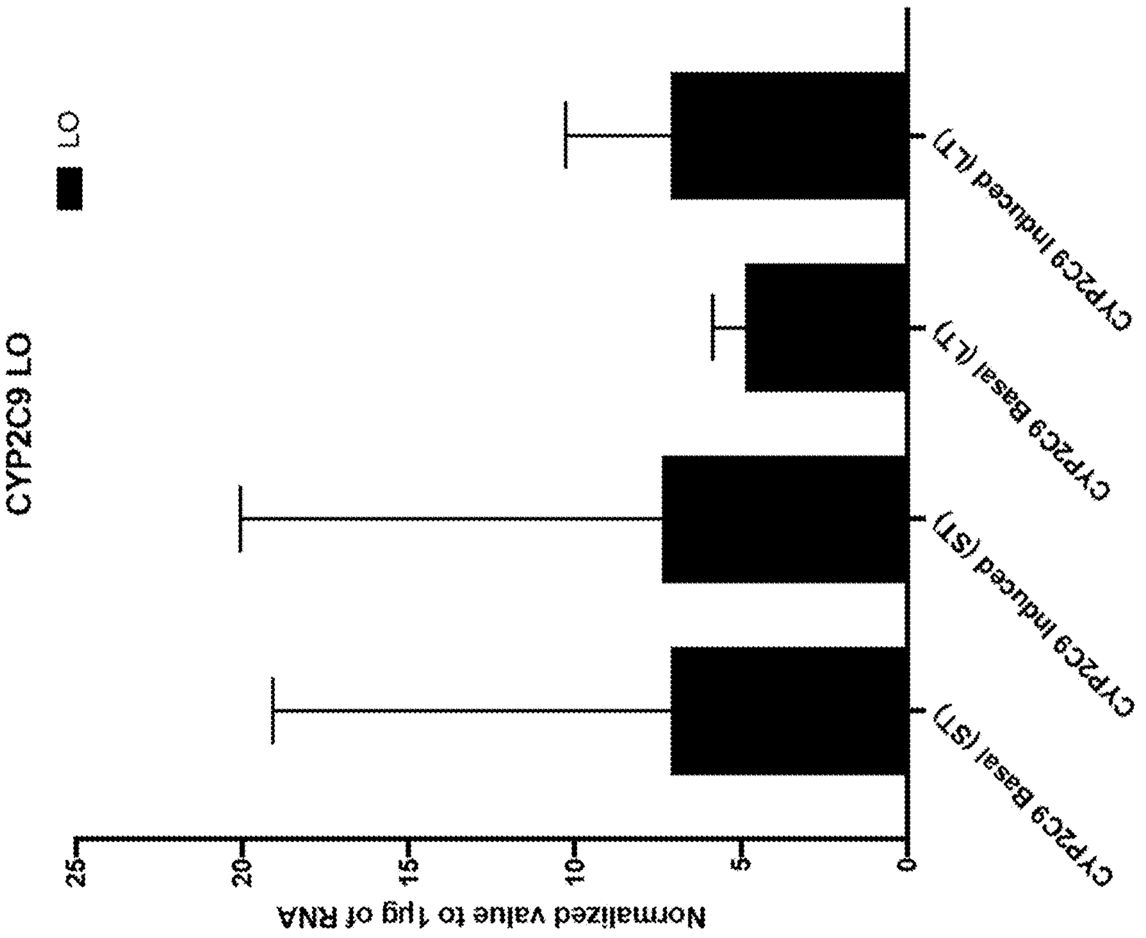
Figure 16:
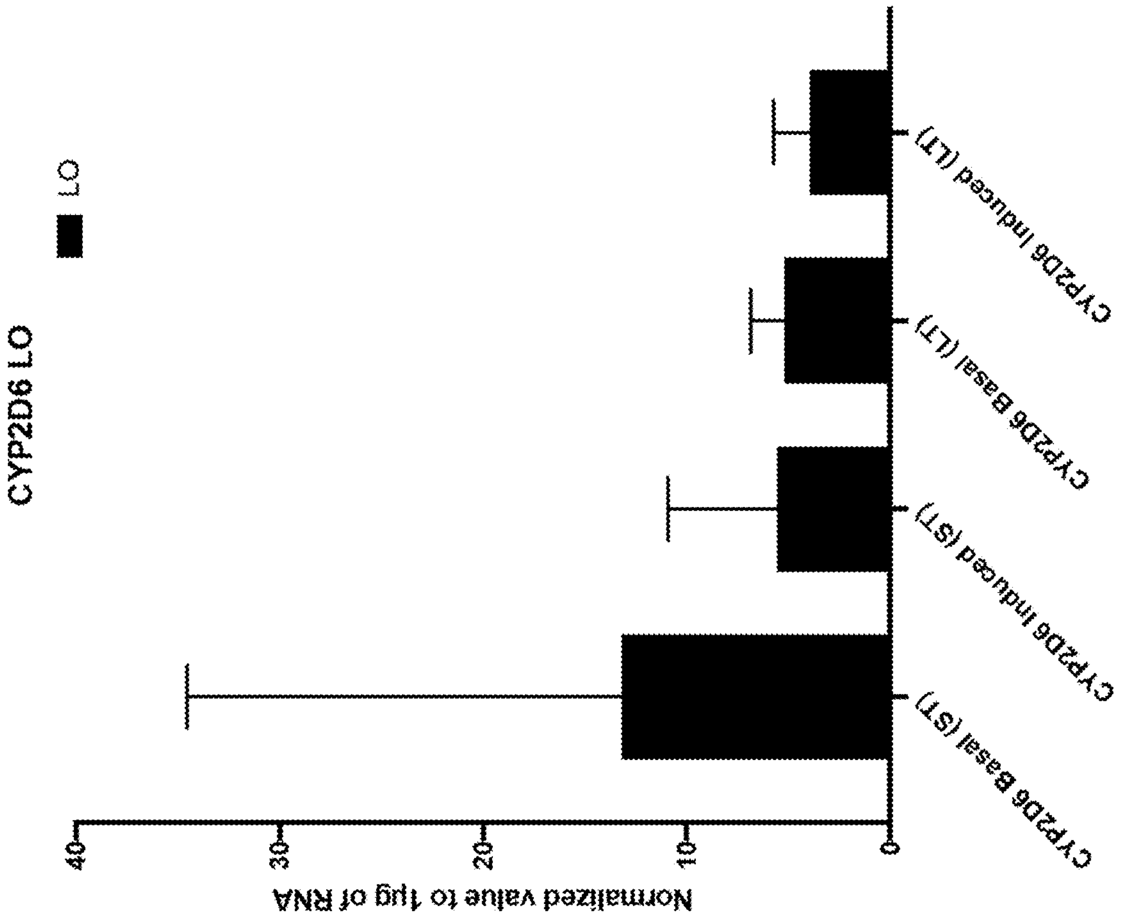
Figure 17:
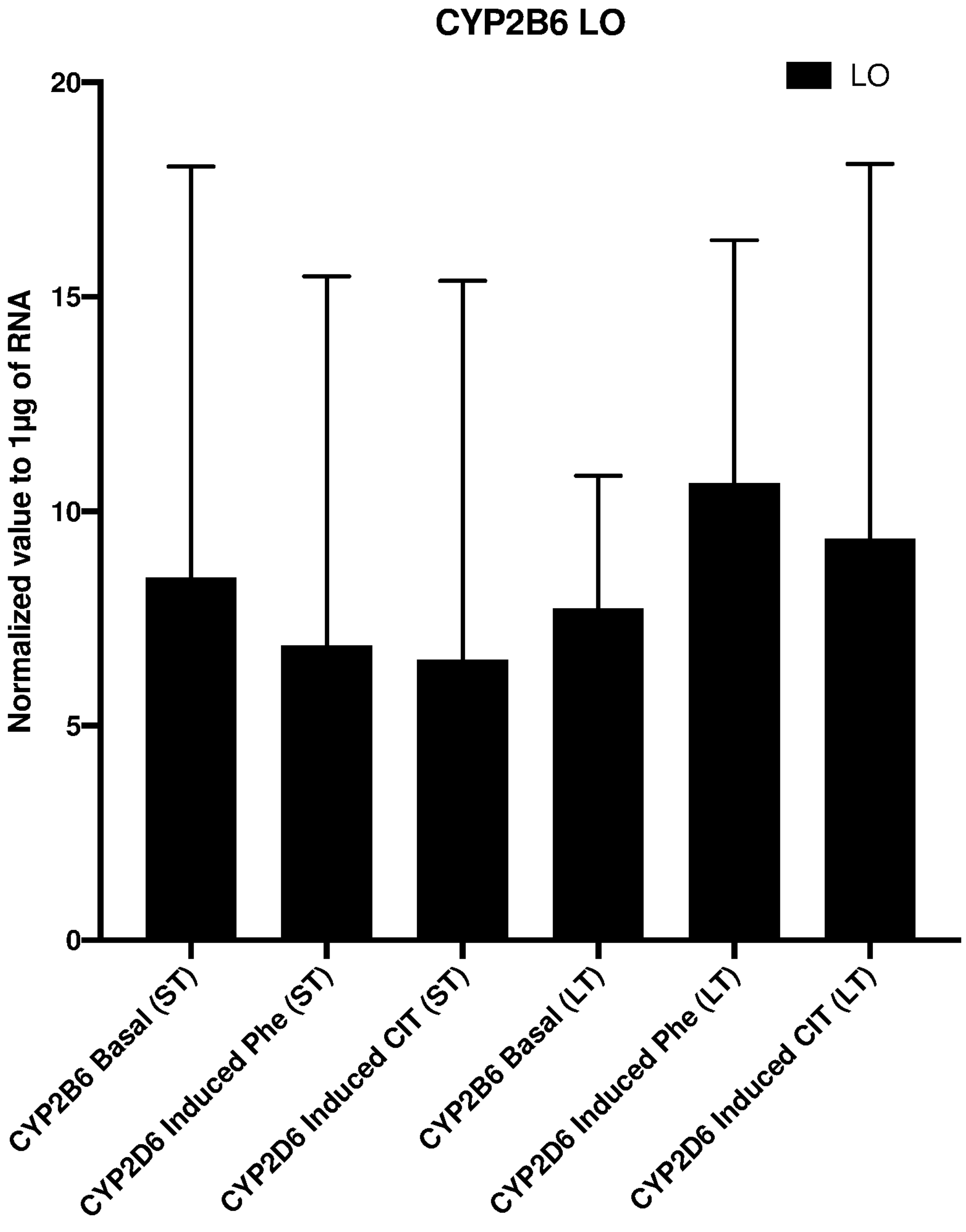
Figure 18:
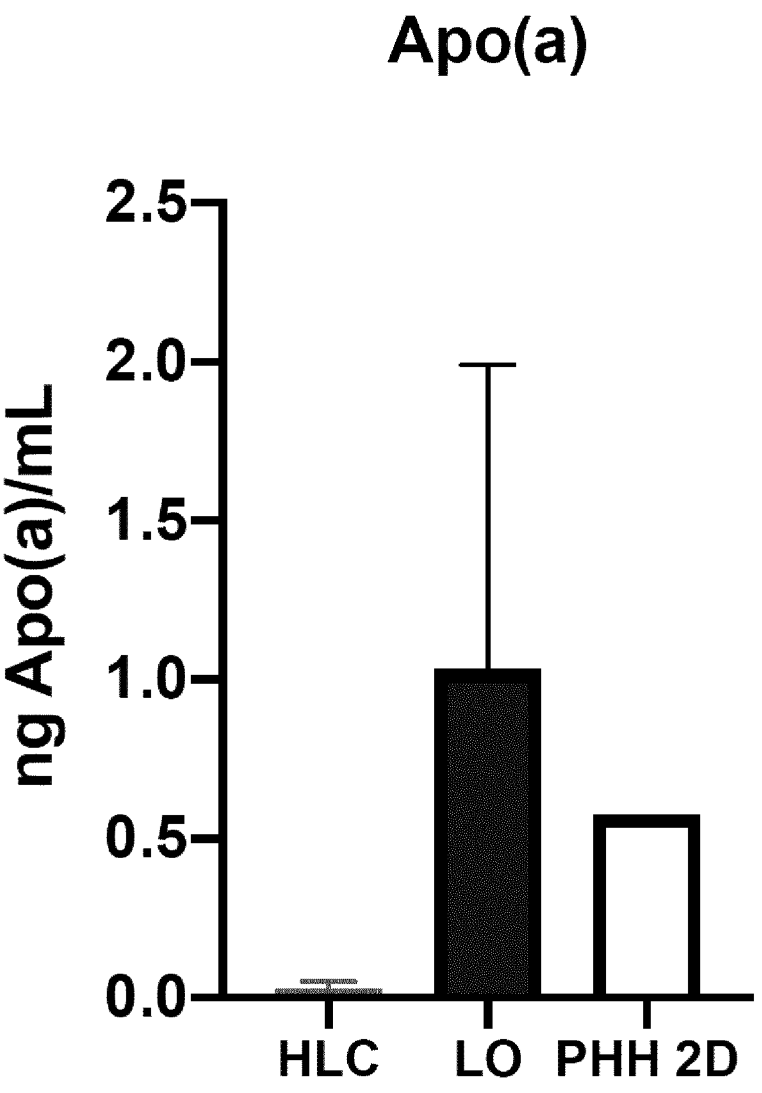
FIG. 18 shows secretion of Apolipoprotein (a) (Apo (a)) by HLC, LO and PHH over 24 h measured by Human Apo (a) ELISA Kit. Ordinate: Quantity of Apolipoprotein (a) in ng/ml. Abscissa (from left to right): Secretion of Apolipoprotein (a) by (i) HCL, (ii) LO, and (iii) PHH.

Concerning LDL internalization, it was noted that the LO model significatively reacted to mevastatin at concentrations of 20, 25 and 30 ug/ml with an increase in LDL-bodipy internalization of 14, 18 and 26% respectively compared to controls (FIG. 2).

Comparison of the Overall Secretion and Metabolites of Testosterone Produced by LO Versus HLC and PHH Subsequently, commonalities and/or differences in the secretome of the different models LO, HLC and PHH were evaluated. The observations by PCA and PLS of the different variables showed a strong variability of the LO and HLC models in contrast to the primary human hepatocytes (PHH) and a better clustering of the LO model with the PHH model.

Due to the importance of the liver in the detoxification of xenobiotics by phase I, II and III biotransformation enzymes; the presence of the different metabolites of testosterone that can be produced by the different models were evaluated. The mass spectrometry analysis was used to calculate the ratios of the different metabolites detected in the different models over short times (after 3 days of culture) and long times (after 2 weeks of culture) with and without induction of CYP3A4. Thus, it has been observed from the result data that the LO model presented a testosterone metabolism profile of closer to PHH than to HLC, in particular owing to the presence of the molecule "Hydroxy-Testosterone 2" in the LO and PHH models, both in basal and induced conditions. Moreover, over long periods of time, an increase in the presence of "Hydroxy-Testosterone 5" in the LO model contrary to the PHH model was observed.

Characterization of CYP Activities Over Short- and Long-Time Periods

The metabolism of the LO model was studied by examining the activities of 5 CYPs (3A4, 1A2, 2C9, 2D6, 2B6) with and without induction over short (after 3 days of culture) and long (after 2 weeks of culture) periods of time.

First, at basal level and over short periods of time, an activity improvement of CYP3A4 by 22.5 times and of CYP1A2 by 40.3 times was observed in the LO model compared to HLC. On the other hand, no significant difference was observed between PHH and LO for CYP3A4 but an important decrease of CYP1A2 activity, by 596 times, was observed in the LO model compared to PHH. Concerning CYP2C9 and 2B6, no difference was observed between the LO model and the HLC model, but a difference between the LO model and the PHH model was observed with a 40.2-fold decrease in activity for CYP2C9 and a 33.9-fold decrease in activity for CYP2B6. In addition, no difference was observed for CYP2D6 between the three models (FIGS. 3 to 7).

On the other hand, very low induction of CYPs was observed for both long and short times (FIGS. 8A, 9A, 10A, 11A, 12A). An induction of CYP1A2 by 7.2 times with omeprazole and of CYP2B6 by 5.8 and 3.3 times with phenobarbital and CITCO respectively was observed in the PHH model.

Moreover, it was observed that RNA quantities have strongly decreased over the long term for both PHH and HLC models in both basal and induced conditions, which showed a poor stability of the PHH and HLC models contrary to the LO model over a long time period (FIGS. 8B, 9B, 10B, 11B, 12B).

For the LO model, a strong variability of the model was observed through the RNA quantities. Firm conclusions on the potential toxic effects of treatments and/or inductions were not observed. Furthermore, the LO model showed a good stability of the CYP activities over long periods of time, in particular with 1.3-fold increase in the basal activity of CYP3A4 (FIGS. 13 to 17).

Comparison of the Secretion of Apolipoprotein (a) Produced by LO, HLC and PHH

It was observed the ability of LOs to secret Apolipoprotein (a) compared to HLC and PHH. The amounts of Apo (a) in the culture medium of each samples were quantified by ELISA. Apo (a) was detected in the culture medium of PHH (0.5 ng/mL) and LO (1.0 ng/mL).

Example 4: Conclusions

The present disclosure thus provides a new method which allow to obtain liver organoids comprising different cell types found in the liver: hepatocytes (albumin+); cholangiocytes (SOX9+ and CFTR+); sinusoidal endothelial cells (CD31+ and LYVE1+) and stellate cells (desmine+ and LHX2+). The LOs also included a structured cellular organization, as seen with phalloidin labelling of the cytoskeleton and a polarization observed with ZO-1 and E-cadherin labeling, proteins known to regulate cellular functions such as cell differentiation and proliferation (Nagaoka et al., 2002).

During differentiation, NANOG expression from day 0 to 2 confirms a loss of pluripotency and therefore of commitment of hiPSC into differentiation; SOX17 expression on day 5 showed the establishment of the definitive endoderm and TBX3 expression from day 13 to 22 showed a differentiation into hepatoblasts. Also, a better differentiation was noticed from the expression of genes related to hepatic functionalities (metabolism of bile, fatty acids, cholesterol, lipoproteins, glucose, insulin, cytochromes and xenobiotics) compared to HLC and a good stability of differentiation up to 49 days as was seen with the PCA of 3'SRP and with the stability of genes such as LIPC from days 19 up to 49; UGT2B7 from days 28 up to 49, and PLG from days 22 up to 49.

The LOs also presented a metabolism capacity. Indeed, in addition to better expression of liver-specific genes, the LO model responded favorably to LDL internalization, this response was increased with statin treatment, and showed strong lipid accumulation with amiodarone and ethanol treatments. For detoxification metabolism by CYPs, the LO presented a stronger activity of CYP enzymes (3A4 and 1A2) compared to HLC, even if the LOs remained below PHH with respect to CYPs 1A2, 2C9 and 2B6 activities. Moreover, it is observed a stability of CYP activity over long periods of time. Contrary to other models, the LOs seem to present a stability on long term as observed from the RNA quantities reflecting viability. Further, a similar profile of testosterone metabolism between LO and PHH was found, showing possible common metabolism pathways between the two models.

Finally, a variability of the LO model was observed, for short times, from the secretome data with PCA and PLS as opposed to PHH. On the other hand, no induction was observed in all models except the PHH model for CYPs 1A2 and 2B6. This type of observation could be explained by the variability of the LO and the inter-individual variability within the population for PHH with respect to the induction of CYPs.

All these experiments were performed on a single hiPSC clone. However, the process of the present disclosure also works on different hiPSC lines.

In conclusion, together, these results showed that a process of the present disclosure allowed to obtain a valid Liver Organoid. This LO is composed of different cell lines further to hepatocytes (stellate cells, cholangiocytes, sinusoidal endothelial cells) and presented an LDL-internalization capacity which was increased upon exposure to statins, and an improvement in CYPS activity compared to HLCs.

REFERENCES

Bharadwaj, S., Liu, G., Shi, Y., Wu, R., Yang, B., He, T., Fan, Y., Lu, X., Zhou, X., Liu, H. et al. (2013). Multi-potential differentiation of human urine-derived stem cells: potential for therapeutic applications in urology. Stem Cells 31, 1840-1856.

Bottenstein, J. E. (1985) Cell Culture in the Neurosciences, Bottenstein, J. E. and Harvey, A. L., editors, p. 3, Plenum Press: New York and London Brewer G J, Torricelli J R, Evege E K, Price P J. Optimized survival of hippocampal neurons in B27-supplemented Neurobasal, a new serum-free medium combination. *J Neurosci Res.* 1993 Aug. 1; 35(5):567-76. doi: 10.1002/jnr.490350513. PMID: 8377226.

Chung Y, Klimanskaya I, Becker S, Li T, Maserati M, Lu S J, Zdravkovic T, Ilic D, Genbacev O, Fisher S, Krtolica A, Lanza R. Human embryonic stem cell lines generated without embryo destruction. *Cell Stem Cell.* 2008 Feb. 7; 2(2):113-7. doi: 10.1016/j.stem.2007.12.013. Epub 2008 Jan. 10. PMID: 18371431.

Gerbal-Chaloin S, Funakoshi N, Caillaud A, Gondeau C, Champon B, Si-Tayeb K. Human inducedd pluripotent stem cells in hepatology: beyond the proof of concept. *Am J Pathol.* 2014 February; 184(2):332-47. doi: 10.1016/j.ajpath.2013.09.026. Epub 2013 Nov. 21. PMID: 24269594.

Gijbels E., Vanhaecke T., Vinken M. (2019) Establishment of Sandwich Cultures of Primary Human Hepatocytes. In: Vinken M. (eds) Experimental Cholestasis Research. Methods in Molecular Biology, vol 1981. Humana, New York, NY. https://doi.org/10.1007/978-1-4939-9420-5_21

Harrison S P, Siller R, Tanaka Y, Xiang Y, Patterson B, Kempf H, Melum E, Asrud K S, Chollet M E, Andersen E, Sandset P M, Baumgarten S, Bonanini F, Kurek D, Mathapati S, Almaas R, Sharma K, Wilson S R, Skottvoll F S, Boger I C, Bogen I L, Nyman T A, Wu J J, Bezrouk A, Cizkova D, Mokry J, Zweigerdt R, Park I H, Sullivan G J, Scalable production of tissue-like vascularised liver organoids from human PSCs, bioRxiv 2020.12.02.406835; doi: https://doi.org/10.1101/2020.12.02.406835

Kaneko H, Subchapter 33B—Activin, Editor(s): Yoshio Takei, Hironori Ando, Kazuyoshi Tsutsui, Handbook of Hormones, Academic Press, 2016, Pages 295-e33B-2, ISBN 9780128010280, https://doi.org/10.1016/B978-0-12-801028-0.00188-4.

Kumar Manoj, Burak Toprakhisar, Matthias Van Haele, Asier Antoranz, Ruben Boon, Francois Chesnais, Jonathan De Smedt, Teresa Izuel Idoype, Marco Canella, Pierre Tilliole, Jolan De Boeck, Tine Tricot, Manmohan Bajaj, Adrian Ranga, Francesca Maria Bosisio, Tania Roskams, Leo A van Grunsven, Catherine M Verfaillie. *A fully defined pluripotent stem cell derived multi-liver-cell model for steatohepatitis and fibrosis*. bioRxiv. Sep. 4, 2020. doi: https://doi.org/10.1101/2020.09.03.280883.

Lang, R., Liu, G., Shi, Y., Bharadwaj, S., Leng, X., Zhou, X., Liu, H., Atala, A. and Zhang, Y. (2013). Self-renewal and differentiation capacity of urine-derived stem cells after urine preservation for 24 hours. PLoS ONE 8, e53980.

Louis, F., Pannetier, P., Souguir, Z., Le Cerf, D., Valet, P., Vannier, J.-P., Vidal, G. and Demange, E. (2017), A biomimetic hydrogel functionalized with adipose ECM components as a microenvironment for the 3D culture of human and murine adipocytes. *Biotechnol. Bioeng.,* 114: 1813-1824. https://doi.org/10.1002/bit.26306

Love M I, Huber W, Anders S (2014). "Moderated estimation of fold change and dispersion for RNA-seq data with DESeq2." *Genome Biology,* 15, 550. doi: 10.1186/s13059-014-0550-8

Madri J A, B M Pratt, A M Tucker; Phenotypic modulation of endothelial cells by transforming growth factor-beta depends upon the composition and organization of the extracellular matrix. *J Cell Biol* 1 Apr. 1988; 106 (4): 1375-1384. doi: https://doi.org/10.1083/jcb.106.4.1375

Massagué J, Xi Q. TGF-β control of stem cell differentiation genes. *FEBS Lett.* 2012; 586(14):1953-1958. doi: 10.1016/j.febslet.2012.03.023

Nagaoka, M., Ise, H. and Akaike, T. (2002) 'Immobilized E-cadherin model can enhance cell attachment and differentiation of primary hepatocytes but not proliferation', *Biotechnology Letters. Springer,* 24(22), pp. 1857-1862. doi: 10.1023/A:1020905532227.

Ouchi R, Togo S, Kimura M, Shinozawa T, Koido M, Koike H, Thompson W, Karns R A, Mayhew C N, McGrath P S, McCauley H A, Zhang R R, Lewis K, Hakozaki S, Ferguson A, Saiki N, Yoneyama Y, Takeuchi I, Mabuchi Y, Akazawa C, Yoshikawa H Y, Wells J M, Takebe T. Modeling Steatohepatitis in Humans with Pluripotent Stem Cell-Derived Organoids. *Cell Metab.* 2019 Aug. 6; 30(2):374-384.e6. doi: 10.1016/j.cmet.2019.05.007. Epub 2019 May 30. PMID: 31155493; PMCID: PMC6687537

Si-Tayeb K, Idriss S, Champon B, Caillaud A, Pichelin M, Arnaud L, Lemarchand P, Le May C, Zibara K, Cariou B. Urine-sample-derived human inducedd pluripotent stem cells as a model to study PCSK9-mediated autosomal dominant hypercholesterolemia. *Dis Model Mech.* 2016 January; 9(1):81-90. doi: 10.1242/dmm.022277. Epub 2015 Nov. 19. PMID: 26586530; PMCID: PMC4728336.

Si-Tayeb K, Noto F K, Nagaoka M, Li J, Battle M A, Duris C, North P E, Dalton S, Duncan S A. Highly efficient generation of human hepatocyte-like cells from inducedd pluripotent stem cells. *Hepatology.* 2010 January; 51(1): 297-305. doi: 10.1002/hep.23354. Erratum in: Hepatology. 2010 March; 51(3):1094. PMID: 19998274; PMCID: PMC2946078.

Soumillon M., Davide Cacchiarelli, Stefan Semrau, Alexander van Oudenaarden, Tarjei S. Mikkelsen. Characterization of directed differentiation by high-throughput single-cell RNA-Seq. *bioRxiv* posted. 2014. doi: http://dx.doi.org/10.1101/003236

Shen M M. Nodal signaling: developmental roles and regulation. *Development.* 2007 March; 134(6):1023-34. doi: 10.1242/dev.000166. Epub 2007 Feb. 7. PMID: 17287255.

Sporn M B, Roberts A B. Peptide growth factors are multifunctional. *Nature.* 1988 Mar. 17; 332(6161):217-9. doi: 10.1038/332217a0. PMID: 2831460.

Takebe, T., Sekine, K., Enomura, M. et al. Vascularized and functional human liver from an iPSC-derived organ bud transplant. *Nature* 499, 481-484 (2013). https://doi.org/10.1038/nature12271.

Takebe T, Zhang R R, Koike H, Kimura M, Yoshizawa E, Enomura M, Koike N, Sekine K, Taniguchi H. Generation of a vascularized and functional human liver from an iPSC-derived organ bud transplant. *Nat Protoc.* 2014 February; 9(2):396-409. doi: 10.1038/nprot.2014.020. Epub 2014 Jan. 23. PMID: 24457331.

Takebe T, Sekine K, Kimura M, Yoshizawa E, Ayano S, Koido M, Funayama S, Nakanishi N, Hisai T, Kobayashi T, Kasai T, Kitada R, Mori A, Ayabe H, Ejiri Y, Amimoto N, Yamazaki Y, Ogawa S, Ishikawa M, Kiyota Y, Sato Y, Nozawa K, Okamoto S, Ueno Y, Taniguchi H. Massive and Reproducible Production of Liver Buds Entirely from Human Pluripotent Stem Cells. *Cell Rep.* 2017 Dec. 5; 21(10):2661-2670. doi: 10.1016/j.celrep.2017.11.005. PMID: 29212014.

U.S. Pat. No. 5,166,065—In vitro propagation of embryonic stem cells

U.S. Pat. No. 5,453,357—Pluripotential embryonic stem cells and methods of making same U.S. Pat. No. 5,690,926—Pluripotential embryonic cells and methods of making same U.S. Pat. No. 5,843,780—Primate embryonic stem cells U.S. Pat. No. 5,914,268—Embryonic cell populations and methods to isolate such populations U.S. Pat. No. 6,090,622—Human embryonic pluripotent germ cells U.S. Pat. No. 6,200,806—Primate embryonic stem cells U.S. Pat. No. 6,562,619—Differentiation of human embryonic germ cells U.S. Pat. No. 6,642,048—Conditioned media for propagating human pluripotent stem cells U.S. Pat. No. 6,800,480—Methods and materials for the growth of primate-derived primordial stem cells in feeder-free culture U.S. Pat. No. 6,921,632—Human embryonic stem cells derived from frozen-thawed embryo U.S. Pat. No. 7,029,913—Primate embryonic stem cells U.S. Pat. No. 8,058,065—Oct3/4, Klf4, c-Myc and Sox2 produce induced pluripotent stem cells U.S. Pat. No. 8,129,187—Somatic cell reprogramming by retroviral vectors encoding Oct3/4. Klf4, c-Myc and Sox2

U.S. Pat. No. 8,158,766—Genes with ES cell-specific expression

U.S. Pat. No. 8,278,104—Induced pluripotent stem cells produced with Oct3/4, Klf4 and Sox2

U.S. Pat. No. 9,499,797—Method of making induced pluripotent stem cells

U.S. Pat. No. 9,637,732—Method of efficiently establishing induced pluripotent stem cells US 2005/0176707—Compositions and methods for inducing cell dedifferentiation Villard E F, Thedrez A, Blankenstein J, Croyal M, Tran T T, Poirier B, Le Bail J C, Illiano S, Nobécourt E, Krempf M, Blom D J, Marais A D, Janiak P, Muslin A J, Guillot E, Lambert G. PCSK9 Modulates the Secretion But Not the Cellular Uptake of Lipoprotein(a) Ex Vivo: An Effect Blunted by Alirocumab. *JACC Basic Transl Sci.* 2016 October; 1(6):419-427. doi: 10.1016/j.jacbts.2016.06.006. PMID: 29308438; PMCID: PMC5753417.

WO 2007/069666—Nuclear reprogramming factor

WO 2012/060473—Method of efficiently establishing induced pluripotent stem cells WO 2016/166479—Method for producing hydrogel from modified hyaluronic acid and type 1 collagen Zeitouni N E, Fandrey J, Naim H Y, von Köckritz-Blickwede M. Measuring oxygen levels in Caco-2 cultures. *Hypoxia* (*Auckl*). 2015; 3:53-66. Published 2015 Oct. 9. doi:10.2147/HP.S85625

Zhang Y, McNeill E, Tian H, Soker S, Andersson K E, Yoo J J, Atala A. Urine derived cells are a potential source for urological tissue reconstruction. *J Urol.* 2008 November; 180(5):2226-33. doi: 10.1016/j.juro.2008.07.023. Epub 2008 Sep. 20. PMID: 18804817

Zhou, T., Benda, C., Dunzinger, S., Huang, Y., Ho, J. C., Yang, J., Wang, Y., Zhang, Y., Zhuang, Q., Li, Y. et al. (2012). Generation of human inducedd pluripotent stem cells from urine samples. Nat. Protoc. 7, 2080-2089.

The invention claimed is:

1. A method for preparing a liver organoid, the method using at least:

i) a three-dimensional porous scaffold seeded with isolated stem cells, ii) a set of cell-culture media for mammal cells suitable for growing and differentiating the isolated stem cells into a liver organoid, the method comprising at least a step of:

a) contacting the seeded stem cells with a first set of cell culture media, under normoxic condition, to differentiate the stem cells in definitive endoderm cells;

b) contacting the definitive endoderm cells obtained at step a) with a second set of cell culture media, under hypoxic condition, to differentiate the definitive endoderm cells in hepatic endoderm cells;

c) contacting the hepatic endoderm cells obtained at step b) with a third set of cell culture media, under hypoxic condition, to differentiate the hepatic endoderm cells in hepatic progenitor cells; and d) contacting the hepatic progenitor cells obtained at step c) with a fourth set of cell culture media, under normoxic condition, to differentiate the hepatic progenitor cells in a liver organoid.

2. The method according to claim 1, the method comprising, a) within the step of differentiating the seeded stem cells in definitive endoderm cells:

a1) a first phase of contacting the cells with a first cell-culture medium supplemented with a SMAD2/3 pathway activator, a fibroblast growth factor, and a bone morphogenetic protein, and a2) a second phase of contacting the cells with a second cell-culture medium supplemented with a SMAD2/3 pathway activator, thereby obtaining the definitive endoderm cells;

b) within the step of differentiating the definitive endoderm cells obtained at step a) in hepatic endoderm cells, contacting the cells with a third cell-culture medium supplemented with a fibroblast growth factor, a vascular endothelial growth factor, and a bone morphogenetic protein, thereby obtaining the hepatic endoderm cells;

c) within the step of differentiating the hepatic endoderm cells obtained at step b) in hepatic progenitor cells:

c1) a first phase of contacting the cells with a fourth cell-culture medium supplemented with a hepatocyte growth factor, and an inhibitor of the TGF-β/Activin/NODAL pathway, c2) a second phase of contacting the cells with a fifth cell-culture medium supplemented with a hepatocyte growth factor, and c3) a third phase of contacting the cells with a sixth cell-culture medium supplemented with a hepatocyte growth factor and an interleukin (IL)-6 cytokine family activator, thereby obtaining the hepatic progenitor cells; and d) within the step of differentiating the hepatic progenitor cells obtained at step c) in the liver organoid:

d1) a first phase of contacting the cells with a seventh cell-culture medium, said cell-culture medium being a hepatocyte-culture medium supplemented with a hepatocyte growth factor, an interleukin (IL)-6 cytokine family activator, and a steroid, d2) a second phase of contacting the cells with an eighth cell-culture medium, said cell-culture medium being a hepatocyte-culture medium supplemented with an interleukin (IL)-6 cytokine family activator, and a steroid, and d3) a third phase of contacting the cells with a ninth cell-culture medium, said cell-culture medium being a hepatocyte-culture medium, and thereby obtaining the liver organoid in the three-dimensional porous cell culture scaffold.

3. The method according to claim 1, comprising a first step before step a), said first step comprising contacting the stem cells seeded in the scaffold in a tenth cell-culture medium supplemented with a ROCK family pathway inhibitor, said step being under hypoxic condition.

4. The method according to claim 1, wherein the scaffold is a cross-linked hydrogel.

5. The method according to claim 1, wherein the scaffold has pores having an average pore size ranging from about 50 to about 500 μm.

6. The method according to claim 1, wherein the SMAD2/3 pathway activator is Activin A, NODAL, TGFβ1, TGFβ2 or TGFβ3, and/or the fibroblast growth factor is FGF2, and/or the bone morphogenetic protein is BMP4, and/or the TGF-β/Activin/NODAL pathway inhibitor is SB431542, and/or the interleukin (IL)-6 cytokine family activator is Oncostatin M, and/or the steroid is dexamethasone.

7. The method according to claim 1, wherein the cell culture media of steps a) to c) is RPMI 1640 or DMEM/Ham's F12, the cell culture media being supplemented with B27 or N-2 supplement, and/or the cell culture media of step d) is a hepatocyte cell culture medium without endothelial growth factor.

8. A kit-of-parts for preparing a liver organoid, the kit-of-parts comprising:

i) isolated stem cells, ii) a three-dimensional porous scaffold comprised of cross-linked hyaluronic acid and of collagen, iii) a set of cell-culture media for mammal cells suitable for differentiating the stem cells into a liver organoid, iv) a set of additives comprising a SMAD2/3 pathway activator, a fibroblast growth factor, a bone morphogenetic protein, a vascular endothelial growth factor, a hepatocyte growth factor, an inhibitor of the TGF-β/Activin/NODAL pathway, an interleukin (IL)-6 cytokine family activator, a steroid, and a steroid, and v) a set of instructions for preparing said liver organoid according to a method of claim 1.

9. The method according to claim 4, wherein the scaffold is a cross-linked hydrogel comprised of cross-linked glycosaminoglycan, and at least one of collagen, fibronectin or laminin.

10. The method according to claim 9, wherein the cross-linked glycosaminoglycan, is a cross-linked hyaluronic acid.

11. The method according to claim 4, wherein the scaffold is a cross-linked hydrogel comprised of cross-linked anionic biopolymers acid and at least one of collagen, fibronectin or laminin.

12. The method according to claim 5, wherein the scaffold has pores having an average pore size ranging from about 100 μm to about 350 μm.

13. The method according to claim 12, wherein the scaffold has pores having an average pore size ranging from about 100 μm to about 200 μm.

14. The method according to claim 7, wherein the cell culture media of steps a) to c) is RPMI 1640.

15. The kit-of-parts for preparing a liver organoid according to claim 8, wherein the set of additives further comprises B27.

16. A method of treating an individual having a liver disorder, comprising at least a step of implanting a liver organoid comprising at least hepatocytes, cholangiocytes, stellate cells, and sinusoidal endothelial cells, and being obtained according to claim 1.

17. A method for drug discovery screens comprising at least the steps of:
- (i) contacting a liver organoid with a library of potential drug candidates,
- (ii) identifying of at least one drug candidate able to bind with a biological target involved in the outcome of a given disease, and
- (iii) selecting the at least one drug candidate for a drug development;

wherein the liver organoid comprises at least hepatocytes, cholangiocytes, stellate cells, and sinusoidal endothelial cells, and being obtained according to claim 1.

18. A method for drug development comprising at least the steps of
- (i) contacting a liver organoid with a drug candidate,
- (ii) measuring of at least one biomarker from the liver organoid, and
- (iii) comparing the measured biomarker with a reference;

wherein the liver organoid comprises at least hepatocytes, cholangiocytes, stellate cells, and sinusoidal endothelial cells, and being obtained according to claim 1.

19. A method for evaluating toxicity of a substance, an environmental pollutant or a food supplement comprising at least the steps of:
- (i) contacting a liver organoid with the substance, the environmental pollutant or the food supplement,
- (ii) measuring at least one biomarker of the liver organoid before and after contacting the liver organoid with the substance, the environmental pollutant or the food supplement,
- (iii) comparing the measured biomarker obtained before and after contacting the liver organoid with the substance, the environmental pollutant or the food supplement to evaluate the liver toxicity of the substance, the environmental pollutant or the food supplement;

wherein the liver organoid comprises at least hepatocytes, cholangiocytes, stellate cells, and sinusoidal endothelial cells, and being obtained according to claim 1.

20. A method of screening for a serious adverse event (SAE) comprising at least the steps of:
- (i) contacting a drug of interest, of which toxicity is of interest, with a liver organoid, and
- (ii) measuring at least one biomarker of the liver organoid before and after contacting the liver organoid with the drug, and
- (iii) comparing the measured biomarker;

wherein the liver organoid comprises at least hepatocytes, cholangiocytes, stellate cells, and sinusoidal endothelial cells, and being obtained according to claim 1.

21. A method of treating an individual having a liver disorder, comprising at least a step of implanting a liver organoid comprising at least hepatocytes, cholangiocytes, stellate cells, and sinusoidal endothelial cells, and the three-dimensional porous scaffold is comprised of cross-linked hyaluronic acid and of collagen.

22. A method for drug discovery screens comprising at least the steps of:
- (i) contacting a liver organoid with a library of potential drug candidates,
- (ii) identifying of at least one drug candidate able to bind with a biological target involved in the outcome of a given disease, and
- (iii) selecting the at least one drug candidate for a drug development;

wherein the liver organoid comprises at least hepatocytes, cholangiocytes, stellate cells, and sinusoidal endothelial cells, and the three-dimensional porous scaffold is comprised of cross-linked hyaluronic acid and of collagen.

23. A method for drug development comprising at least the steps of
- (i) contacting a liver organoid obtained according to claim 1 with a drug candidate,
- (ii) measuring of at least one biomarker from the liver organoid, and
- (iii) comparing the measured biomarker with a reference;

wherein the liver organoid comprises at least hepatocytes, cholangiocytes, stellate cells, and sinusoidal endothelial cells, and the three-dimensional porous scaffold is comprised of cross-linked hyaluronic acid and of collagen.

24. A method for evaluating toxicity of a substance, an environmental pollutant or a food supplement comprising at least the steps of:
- (i) contacting a liver organoid obtained according to claim 1 with the substance, the environmental pollutant or the food supplement,
- (ii) measuring at least one biomarker of the liver organoid before and after contacting the liver organoid with the substance, the environmental pollutant or the food supplement,
- (iii) comparing the measured biomarker obtained before and after contacting the liver organoid with the substance, the environmental pollutant or the food supplement to evaluate the liver toxicity of the substance, the environmental pollutant or the food supplement;

wherein the liver organoid comprises at least hepatocytes, cholangiocytes, stellate cells, and sinusoidal endothelial cells, and the three-dimensional porous scaffold is comprised of cross-linked hyaluronic acid and of collagen.

25. A method of screening for a serious adverse event (SAE) comprising at least the steps of:
- (i) contacting a drug of interest, of which toxicity is of interest, with a liver organoid obtained according to claim 1, and
- (ii) measuring at least one biomarker of the liver organoid before and after contacting the liver organoid with the drug, and
- (iii) comparing the measured biomarker;

wherein the liver organoid comprises at least hepatocytes, cholangiocytes, stellate cells, and sinusoidal endothelial cells, and the three-dimensional porous scaffold is comprised of cross-linked hyaluronic acid and of collagen.

* * * * *